US008940504B2

(12) United States Patent
Steenstrup et al.

(10) Patent No.: US 8,940,504 B2

(45) Date of Patent: Jan. 27, 2015

(54) HOST CELL PROTEIN KNOCK-OUT CELLS FOR PRODUCTION OF THERAPEUTIC PROTEINS

(75) Inventors: Thomas Dock Steenstrup, Gentofte (DK); Peder Lisby Norby, Copenhagen O (DK)

(73) Assignee: Novo Nordisk Healthcare AG, Zurich (CH)

(*) Notice: Subject to any disclaimer, the term of this patent is extended or adjusted under 35 U.S.C. 154(b) by 57 days.

(21) Appl. No.: 13/418,844

(22) Filed: Mar. 13, 2012

(65) Prior Publication Data

US 2012/0171721 A1 Jul. 5, 2012

Related U.S. Application Data

(60) Continuation of application No. 12/700,324, filed on Feb. 4, 2010, now Pat. No. 8,158,771, which is a division of application No. 11/995,109, filed as application No. PCT/EP2006/064220 on Jul. 13, 2006, now Pat. No. 7,696,318.

(60) Provisional application No. 60/706,369, filed on Aug. 8, 2005.

(30) Foreign Application Priority Data

Jul. 13, 2005 (EP) .................................... 05106401

(51) Int. Cl.

*C07K 14/745* (2006.01)
*C12N 15/113* (2010.01)
*C07H 21/04* (2006.01)

(52) U.S. Cl.

USPC ...... 435/69.1; 435/91.1; 435/91.31; 435/358; 435/455; 530/350; 530/380; 536/23.1; 536/24.31

(58) Field of Classification Search

USPC ............. 435/6.1, 91.1, 91.31, 69.1, 455, 358; 530/350, 380; 536/23.1, 24.31

See application file for complete search history.

(56) References Cited

FOREIGN PATENT DOCUMENTS

| | | |
|---|---|---|
| EP | 0658168 | 11/2000 |
| JP | H08-500833 A | 1/1996 |
| JP | 2001-500381 A | 1/2001 |
| WO | WO 98/12300 | 3/1998 |
| WO | WO 00/38517 | 7/2000 |
| WO | WO 2004/092735 | 10/2004 |
| WO | WO 2005/028630 | 3/2005 |
| WO | WO 2005/040187 | 5/2005 |
| WO | WO 2006/067230 | 6/2006 |

OTHER PUBLICATIONS

Jurlander, B. et al., "Recombinant Activated Factor VII (rFVIIa): Characterization, Manufacturing, and Clinical Development", Seminars in Thrombosis and Hemostasis, 2001, vol. 27, No. 4, pp. 373-383.

Mori, K. et al., "Engineering Chinese Hamster Ovary Cells to Maximize Effector Function of Produced Antibodies Using FUT8 siRNA", Biotechnology and Bioengineering, 2004, vol. 88, No. 7, pp. 901-908.

Yamane-Ohnuki, N. et al., "Establishment of FUT8 Knockout Chinese Hamster Ovary Cells : An Ideal Host Cell Line for Producing Completely Defucosylated Antibodies with Enhanced Antibody-Dependent Cellular Cytotoxicity", Biotechnology and Bioengineering, 2004, vol. 87, No. 5, pp. 614-622.

Sooy, K. et al., "Transcriptional Repression of the Rat Osteocalcin Gene by δEF1", Endocrinology, 2002, vol. 143, No. 9, pp. 3370-3375.

Hall, M. O. et al., "Both protein S and Gas6 stimulate outer segment phagocytosis by cultured rat retinal pigment epithelial cells", Experimental Eye Research, 2005, vol. 81, No. 5, pp. 581-591.

Chu, M.D. et al., XP-002361937, EMBL Data Library, 1993.

Josic, D. et al., "Preparation of vitamin K-dependent proteins, such as clotting factors II, VII, IX and X and clotting inhibitor Protein C", Journal of Chromatography, 2003, vol. 790, vol. 1-2, pp. 183-197.

Angelillo-Scherrer, A. et al., "Deficiency or inhibition of Gas6 causes platelet dysfunction and protects mice against thrombosis", Nature Medicine, 2001, vol. 7, No. 2, pp. 215-221.

Nelsestuen, G.L. et al., "Role of γ-Carboxyglutamic Acid", Journal of Biological Chemistry, 1976, vol. 251, No. 22, pp. 6886-6893.

Yan, S.C.B et al., "Characterization and Novel Purification of Recombinant Human Protein C from Three Mammalian Cell Lines", Biotechnology, 1990, vol. 8, pp. 655-661.

Brown, M.A. et al., "Identification and Purification of Vitamin K-dependent Proteins and Peptides with Monoclonal Antibodies Specific for γ-Carboxyglutamyl (GIa) Residues", Journal of Biological Chemistry, 2000, vol. 275, No. 26, pp. 19795-19802.

Furie, B. et al., "Conformation-specific Antibodies as Probes of the γ-Carboxyglutamic Acid-rich Region of Bovine Prothrombin", Journal of Biological Chemistry, 1979, vol. 254, No. 19, pp. 9766-9771.

Church, W.R. et al., "A Conserved Epitope on Several Human Vitamin K-dependent Proteins", Journal of Biological Chemistry, 1988, vol. 263, No. 13, pp. 6259-6267.

Bjoern and Thim et al., Activation of Coagulation Factor VII to VIIa, Research Disclosure, 1986, vol. 29, No. 60.

Yan, S.B.,"Review of Conformation-specific Affinity Purification Methods for Plasma Vitamin K-dependent Proteins", Journal of Molecular Recognition, 1996, vol. 9, pp. 211-218.

Furie, B. et al., "Antibodies Directed Against a γ-Carboxyglutamic Acid-rich Region of Bovine Prothrombin", The Journal of Biological Chemistry, 1978, vol. 253, No. 24, pp. 8980-8987.

Brummelkamp et al., "A System for Stable Expression of Short Interfering RNAs in Mammalian Cells", Science, 2002, vol. 296, pp. 550-553.

(Continued)

*Primary Examiner* — Jane Zara

(74) *Attorney, Agent, or Firm* — Nonna G. Akopyan; Reza Green; Richard W. Bork

(57) ABSTRACT

The present invention relates to methods and means for making Vitamin K-dependent protein compositions which are devoid or substantially devoid of protein contaminants. In particular, methods and means useful for the reduction or elimination of protein contaminants also being Vitamin K-dependent proteins are described.

1 Claim, 6 Drawing Sheets

(56) References Cited

OTHER PUBLICATIONS

Furie et al., "The Molecular Basis of Blood Coagulation", Cell, 1988, vol. 53, pp. 505-518.

Miyagishi et al., "U6 Promoter-Driven sIRNAs With Four Uridine 3' Overhangs Efficiently Suppress Targeted Gene Expression in Mammalian Cells", Nature Biotechnology, 2002, vol. 19, pp. 497-500.

Database Genbank, Oct. 28, 1995, Accession No. S78744.

Database Genbank, Apr. 18, 2005, Accession No. Z25469.

Database Genbank, May 18, 1994, Accession No. L27439.

RansiRNA vector

A)

B)

HOST CELL PROTEIN KNOCK-OUT CELLS FOR PRODUCTION OF THERAPEUTIC PROTEINS

CROSS-REFERENCE TO RELATED APPLICATIONS

This application is a continuation of U.S. application Ser. No. 12/700,324, filed Feb. 4, 2010, which is a divisional of U.S. application Ser. No. 11/995,109, filed Jan. 9, 2008 which is a 35 U.S.C. §371 national stage application of International Patent Application PCT/EP2006/064220 (published as WO 2007/006808 A1), filed Jul. 13, 2006, which claimed priority of European Patent Application 05106401.2, filed Jul. 13, 2005; this application further claims priority under 35 U.S.C. §119 of U.S. Provisional Application 60/706,369, filed Aug. 8, 2005.

FIELD OF THE INVENTION

The present invention relates to methods for producing compositions comprising Vitamin K-dependent protein having a very low or negligible content of protein contaminants and to compositions derived from such methods. Such methods may either be used alone or in combination with other methods for the purpose of reducing the relative content of protein contaminants. The present invention is particularly relevant in the preparation of compositions of coagulation factors selected from Thrombin polypeptides (FII/FIIa), Factor X polypeptides (FX/FXa), Factor IX polypeptides FIX/FIXa), Factor VII polypeptides (FVII/FVIIa), and the anticoagulant Protein C, in particular Factor VII polypeptides.

BACKGROUND OF THE INVENTION

In the production of recombinant proteins from cultures of microorganisms or cell lines, the final production step is the recovery and optionally the concentration of the product of interest. Culture media in which the cells have been grown and which contain secreted proteins, and, in particular, cell lysates containing intracellular proteins of interest also contain, to a greater or lesser extent, other proteins produced by the cells, apart from other contaminants, such as media components, nucleic acids and the like. In order to obtain a purified protein product, it is therefore necessary to separate the protein of interest from other proteins and polypeptides and other impurities in the crude material containing the protein of interest. It is however, often difficult to remove protein contaminants comprising domains of the same nature as the polypeptide of interest.

Vitamin K-dependent proteins are distinguished from other proteins by sharing a common structural feature in their amino terminal part of the molecule. The N-terminal of these proteins, also referred to as the Gla-domain, is rich in the unusual amino acid γ-carboxy glutamic acid which is synthesized from glutamate in a Vitamin K dependent reaction catalysed by the enzyme γ-glutamyl carboxylase. Because of the presence of about 9 to 12 Gla residues, the Gla-domain is characterised by being capable of binding divalent cations such as $Ca^{2+}$. Upon binding of metal ions, these proteins undergo conformational changes which can be measured by several techniques such as circular dichroism and fluorescence emission.

The discovery of metal induced conformational changes of Gla-containing proteins (Nelsestuen et. al., J. Biol. Chem. 1976; 251, 6886-6893) together with identification of conformation specific polyclonal antibodies (Furie al., J. Biol. Chem. 1978; 253, 8980-8987) opened the way for the introduction of conformation specific immunoaffinity chromatography. These antibodies could recognise and bind the Gla-domain in the presence of $Ca^{2+}$ ions but released the protein upon removal of $Ca^{2+}$ ions using a $Ca^{2+}$ chelator such as EDTA or citrate.

In 1980's conformation specific pseudoaffinity chromatography was developed making use of the unique property of Gla containing proteins to undergo metal induced changes in conformation. Pseudoaffinity chromatography differs from the conventional affinity chromatography in that there is no immobilized affinity ligand involved and it is performed on a conventional chromatographic matrix (Yan S. B., J. Mol. Recog, 1996; 9, 211-218). The Gla protein can be adsorbed to an anion exchange material by eliminating divalent metal ions. Subsequently, elution is performed by adding $Ca^{2+}$ to the elution buffer.

In 1986, Bjørn and Thim reported purification of rFVII on an anion exchange material taking advantage of $Ca^{2+}$-binding property of Gla-domain of FVII (Bjørn S, and Thim L., Research Dislosure, 1986, 26960-26962). Adsorption was achieved in a buffer without $Ca^{2+}$ and elution of FVII was possible using a $Ca^{2+}$ containing buffer with low ionic strength and under mild conditions. Yan et al. have used the same principle for the purification of recombinant human Protein C (Yan S. B. et al., Bio/technology. 1990; 8, 655-661).

Brown et al. (Brown et al., J. Biol. Chem. 2000; 275, 19795-19802.) have reported monoclonal antibodies specific for Gla residues. These antibodies could recognize all of the Gla proteins tested: Factor VII, Factor IX, Factor II, Protein C, Protein S, GAS-6, bone matrix Gla protein, conantokin G. Several conformational specific antibodies raised against one Gla protein show cross reactivity with other Gla proteins (Furie B. and Furie B., J. Biol. Chem. 1979; 254, 9766-9771; Church et al., J. Biol. Chem. 1988; 263, 6259-6267).

While the presence of the Gla-domain provides an advantage for separation of Gla containing proteins from other proteins, the inventors of present invention observed that similar properties and behaviour of the Gla containing proteins makes it difficult to separate them from each other.

Proteins with a Gla-domain comprise the following proteins: GAS-6, Protein S, Factor II (Prothrombin), Factor X, Factor IX, Protein C, Factor VII, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Bone Gla protein, Matrix Gla protein, and Osteocalcin.

The need for efficiently separating a Vitamin K-dependent protein of interest, such as a Gla-domain containing polypeptide of interest, from protein contaminants is a particularly relevant issue when dealing with the purification of such polypeptides produced in cell cultures, because the host cell may produce significant amounts of protein contaminants that may cause undesirable immunogenic reactions upon use of the polypeptide.

SUMMARY OF THE INVENTION

The present invention relates in a broad aspect to the generation of compositions comprising a Vitamin K-dependent protein of interest which is devoid or substantially devoid of at least one protein contaminant expressed by the host cell.

Thus in a first aspect the present invention relates to a host cell expressing a Vitamin K-dependent protein of interest, the host cell being modified to express a substantially lower amount of at least one protein contaminant expressed endogenous by the host cell in the absence of the modification. In one embodiment the host cell is transfected with a polynucleotide construct to encode the Vitamin K-dependent protein of interest.

The term "modified" as used herein refers to a cell that has been engineered by any man-made molecular or cell biology techniques or process useful in the industry.

In a second aspect the present invention relates to a method for producing a host cell according to the invention, the method comprising the following steps in any order:

a) optionally transfecting the host cell with a polynucleotide construct encoding a Vitamin K-dependent protein of interest; and
b) modifying the host cell to express a substantially lower amount of at least one protein contaminant expressed endogenous by the host cell in the absence of the modification.

In a further aspect the present invention relates to a method for producing a composition comprising a Vitamin K-dependent protein of interest with a substantially lower amount of at least one protein contaminant expressed endogenous by the host cell in the absence of modification, the method comprising the steps of growing a host cell expressing a Vitamin K-dependent protein of interest, the host cell being modified to express a substantially lower amount of at least one protein contaminant expressed endogenous by the host cell in the absence of the modification, in a growth medium and harvesting the growth medium comprising the Vitamin K-dependent protein of interest.

In a further aspect the present invention relates to a method for producing a composition comprising a Vitamin K-dependent protein of interest with a substantially lower amount of at least one protein contaminant expressed endogenous by the host cell in the absence of modification, the method comprising the steps of:

a) producing a host cell according to the invention; and
b) growing the host cell in a growth medium and harvesting the growth medium comprising the Vitamin K-dependent protein of interest.

In a further aspect the present invention relates to a composition produced by a method for producing a composition comprising a Vitamin K-dependent protein of interest with a substantially lower amount of at least one protein contaminant expressed endogenous by the host cell in the absence of modification, the method comprising the steps of growing a host cell expressing a Vitamin K-dependent protein of interest, the host cell being modified to express a substantially lower amount of at least one protein contaminant expressed endogenous by the host cell in the absence of the modification, in a growth medium and harvesting the growth medium comprising the Vitamin K-dependent protein of interest.

In a further aspect the invention relates to modified cells expressing a Vitamin K-dependent protein of interest useful for generating compositions comprising a Vitamin K-dependent protein of interest, devoid or substantially devoid of protein contaminants expressed by the host cell.

In a further aspect the invention relates to methods for reducing or eliminating the content of at least one protein contaminant in a composition comprising a Vitamin K-dependent protein of interest wherein at least one protein contaminant expressed by the host cell is inhibited.

In a further aspect the invention relates to new nucleic acid sequences encoding protein S in CHO cell.

In a further aspect the invention relates to a new amino acid sequence of protein S in CHO cell.

The vector is composed of two polymerase III promoters transcribing the siRNA template in each direction. The two RNA transcripts are complementary and anneal to form the final siRNA molecule. The vector contains a hygromycin resistance gene which makes it possible to select for stable cell clones.

Figure 1:
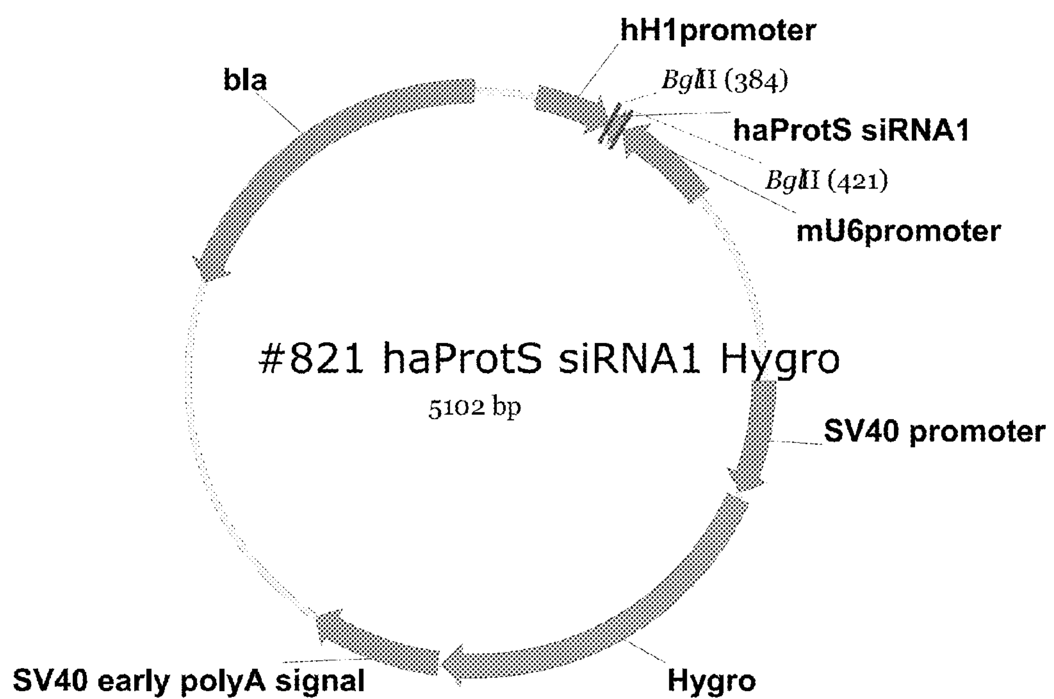
FIG. 1 illustrates the RansiRNA vector.
Figure 2:
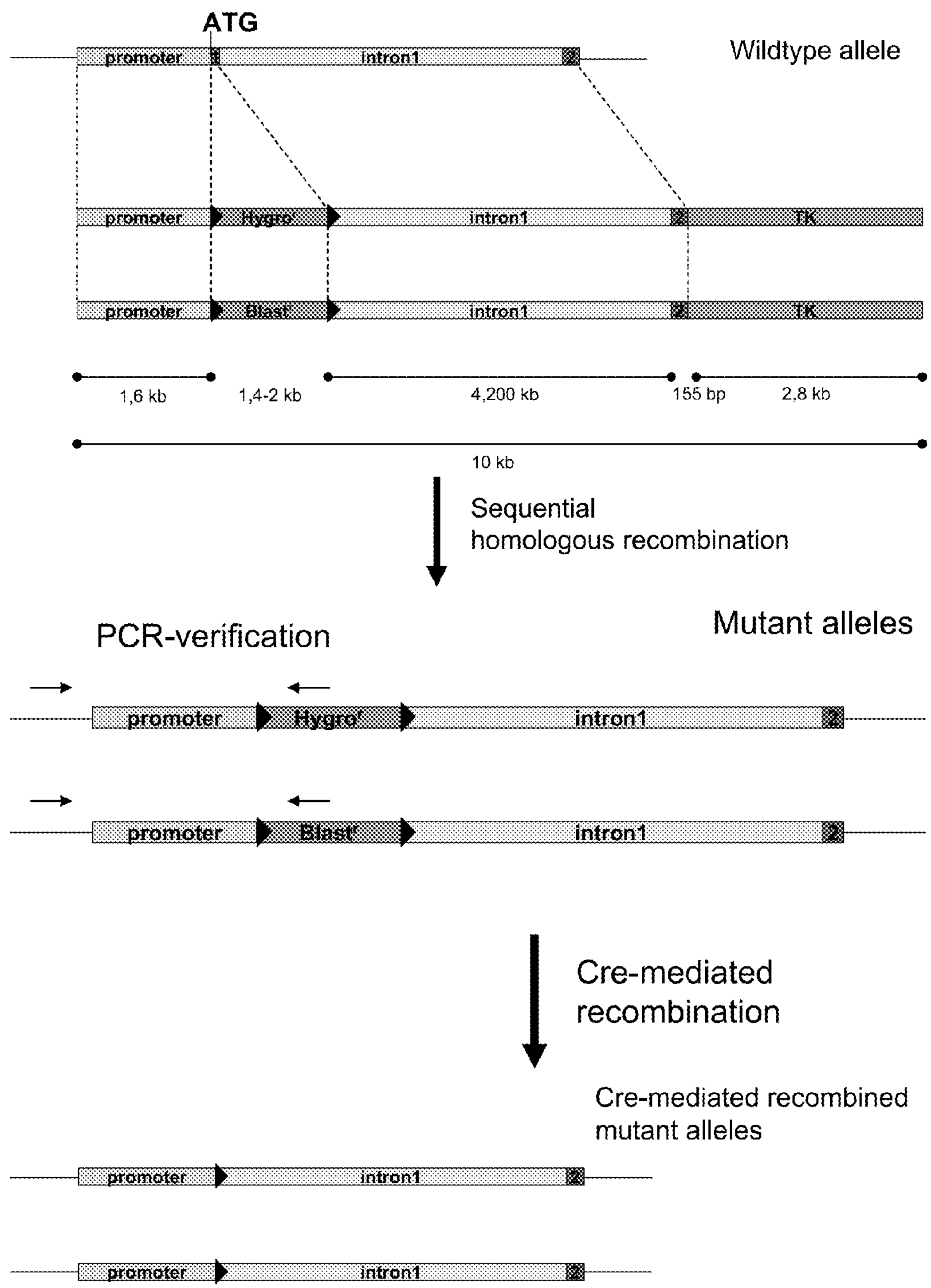

FIG. 2 illustrates steps in the Gene targeting method.

In the CHO Protein S gene targeting construct the coding part of exon 1 has been exchanged by a hygromycin or a blasticidin resistance gene for positive selection. Furthermore, the TK gene is inserted next to exon 2 for negative selection. Two cre/lox sites are flanking the resistance gene. Following homologous recombination the cell population can be screened using primers specific to promoter region outside the construct and to the resistance gene in the construct. Once the alleles have been knocked-out for wildtype Protein S, the cells may be transfected by an expression plasmids containing Cre recombinase. The Cre recombinase will recombinate at the cre/lox sites and resistance genes are deleted from the cell genome.

Figure 3:
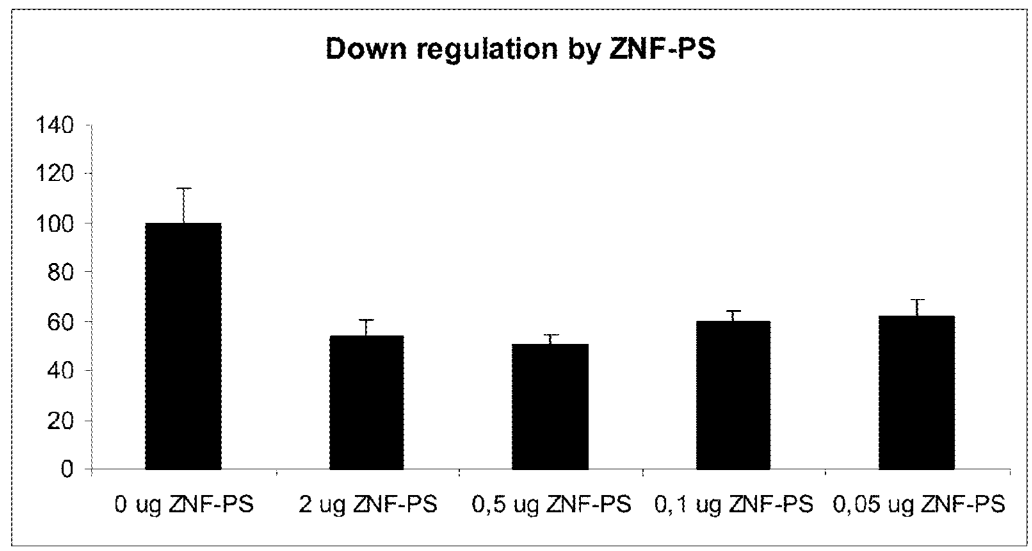
Figure 3:
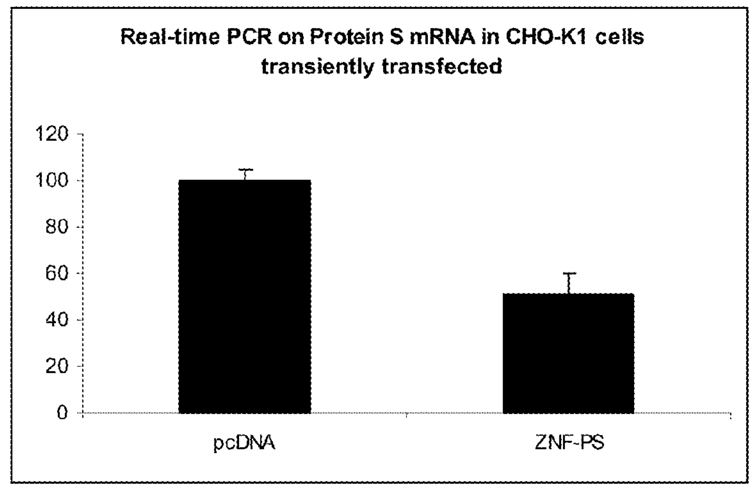

FIG. 3 illustrates down regulation of the Protein S gene in CHO-K1 cells using the synthetic made gene ZNF-PS.

FIG. 3*a*: The synthetic gene ZNF-PS downregulates Protein S transcription in CHO-K1 cells, determined by luciferase reporter assay. The figure shows luciferase readout from a reporter containing the Protein S promoter. The pRL-CMV (Promega, Madison) vector was used as control for transfection efficiency. ZNF-PS down regulates Protein S promoter activity by 50% in a transient transfection.

FIG. 3*b*: The synthetic gene ZNF-PS downregulates Protein S transcription in CHO-K1 cells, determined by real-time PCR on Protein S mRNA. The figure illustrates a realtime PCR quantitation of the Protein S mRNA in CHO-K1 transiently trans-fected with ZNF-PS. The pEGFP (Clontech, Mountain View) vector was used as control for transfection efficiency. In this experiment ZNF-PS also down regulates Protein S 50%.

Figure 4:
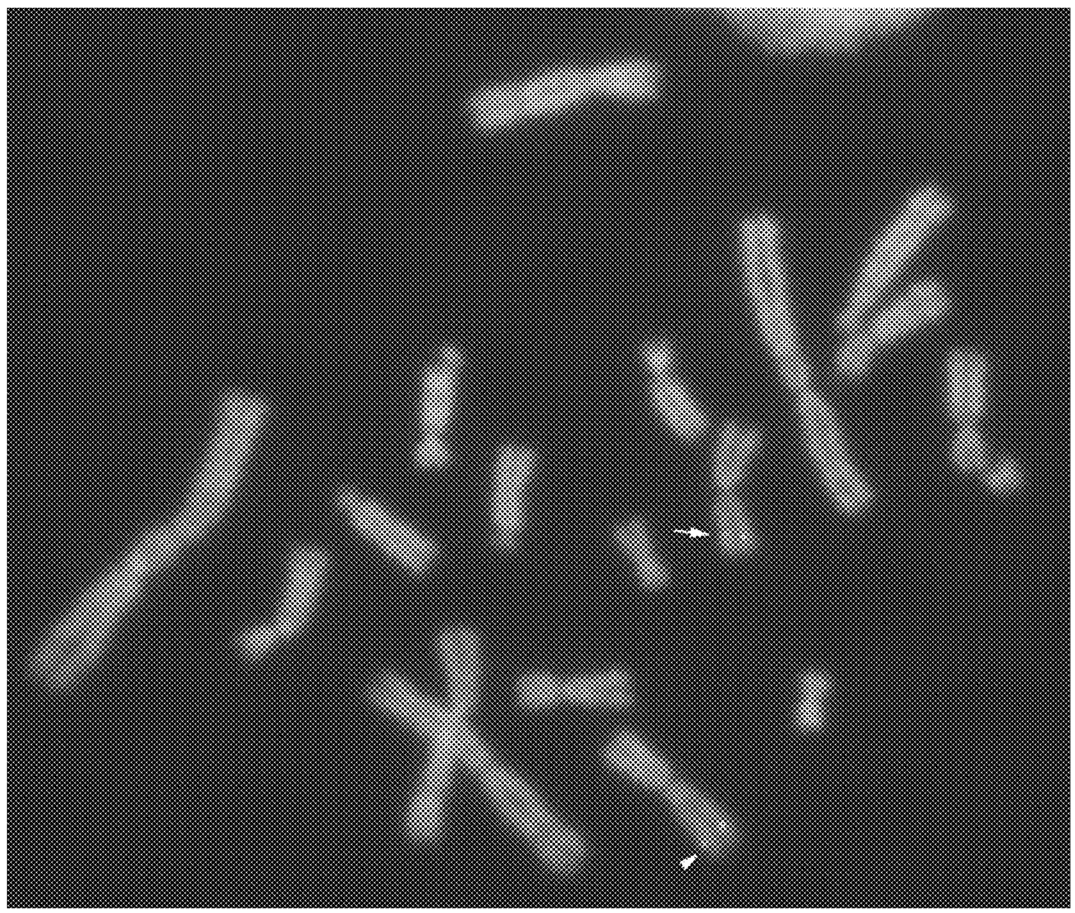

FIG. 4: The Protein S gene is localized onto two different chromosomes in the same metaphase of CHO-K1 cells. The figure illustrates Protein S gene localization in the CHO-K1 genome. FISH was performed on CHO-K1 chromosomes using Protein intron 1 as probe.

Figure 5:
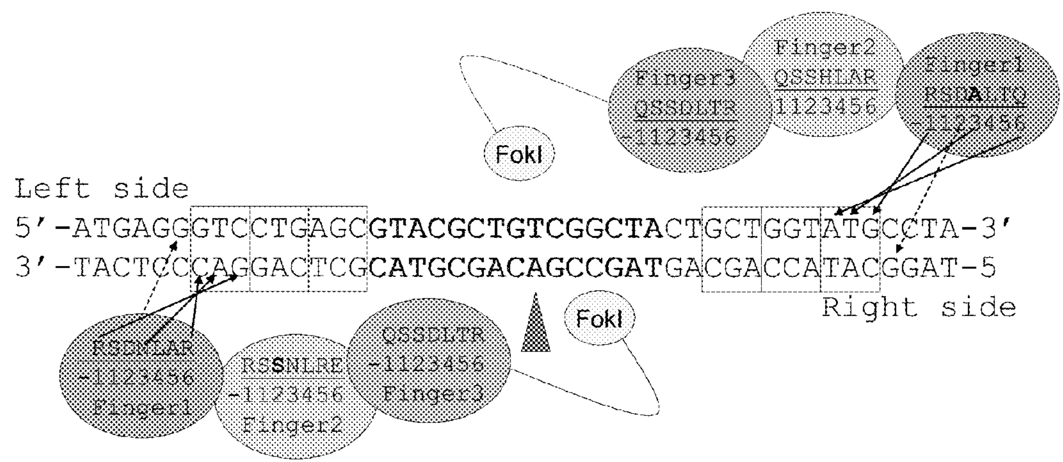

FIG. 5: Two zinc finger proteins fused to nucleases bind inside exon1 of the CHO Protein S gene. The figure illustrates DNA binding specificity of two zinc finger proteins fused to Fok I nuclease.

The left zinc finger protein is expected to bind to 5'-GTC-CTGAGC-3' (upper strand) and the right zinc finger will bind to 5'-GCTGGTATG-3' (upper strand) both sequence element is harbored by Protein S exon 1. The two zinc finger are either fused to Fok I og Sts I nucleases, the nucleases will homodimerize and perform the cleavage of the DNA strands.

Figure 6:
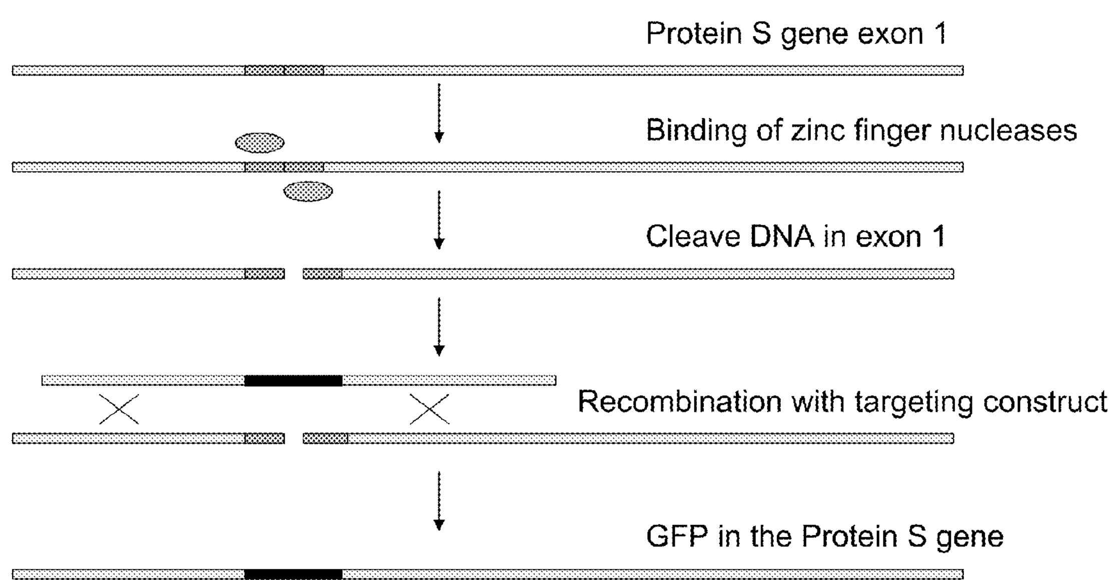

FIG. 6: Gene targeting by homologous recombination enhanced by zinc finger nuclease cleavage. The figure illustrates the step in homologous recombination enhanced by zinc finger nucleases.

The zinc finger nucleases will bind their specific binding sites within Protein S exon 1 and cleave the DNA strands. The gene targeting vector transfected along with the nucleases contains a large fragment identical to the Protein S gene, on each side of the EGFP gene. Recombination occurs between the Protein S gene and targeting vector. Recombinant cells can be sorted due to EGFP expression.

DETAILED DESCRIPTION OF THE INVENTION

The present invention relates to a host cell for the production of recombinant proteins, wherein this host cell is modified to express a substantially lower amount of at least one protein contaminant expressed endogenous by the host cell in the absence of the modification.

It will be understood that any method or technique for reducing expression of the contaminating protein may be used. The examples of such methods including siRNA targeting, targeted gene knock-out, transfection with a transcriptional factor, and site-specific cleavage of the DNA strands encoding protein contaminants are not to be construed limiting in any way. In principle, any molecular biology, cell biology, or selection method may be used to reduce the expression level of a particular protein contaminant. The present invention is particular useful in the situation, where the Vitamin K-dependent protein of interest is very closely related with one or more protein contaminants, such as when the protein contaminant is a second vitamin K-dependent protein. Due to the close relationship between a vitamin K-dependent protein of interest and a protein contaminant, which is a second vitamin K-dependent protein, such protein contaminant may be very difficult remove by purification methods.

The present invention further relates to compositions comprising Vitamin K-dependent proteins of interest devoid or substantially devoid of at least one protein contaminant expressed by a host cell.

In one embodiment of the invention, the Vitamin K-dependent protein of interest is selected from the group consisting of GAS-6, Protein S, Factor II (Prothrombin), Factor X, Factor IX, Protein C, Factor VII, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Bone Gla protein, Matrix Gla protein, and Osteocalcin. The Vitamin K-dependent proteins may be in either an activated or a non-activated form, such as Factor II and Factor IIa, and Factor X and Factor Xa.

In one embodiment of the invention the Vitamin K-dependent protein of interest is a coagulation factor, such as e.g. FVII or FVIIa polypeptides. In one embodiment the Vitamin K-dependent protein of interest is wild type human FVIIa.

In one embodiment of the invention, the protein contaminants is a second different Vitamin K-dependent protein. Thus, the protein of interest and the protein contaminant may both be a Vitamin K-dependent protein.

In one embodiment of the invention the protein contaminants is Protein S. In one embodiment, the protein contaminants is hamster Protein S.

In one embodiment of the invention the host cell is selected from the group consisting of CHO cells, 293 (HEK293) cells, BKH cells, HKB11 cells, SP2/0 cells, and NS0 cells.

The present invention furthermore relates to a host cell expressing a Vitamin K-dependent protein of interest, which host cell comprises a siRNA construct targeting at least one protein contaminant expressed by the host cell.

The term “siRNA” as used herein refers to small interfering RNA, sometimes known as short interfering RNA or silencing RNA known in the art of molecular biology.

In one embodiment the host cell has been modified by transfection with at least one siRNA polynucleotide construct targeting a mRNA encoding a protein contaminant expressed endogenous by the host cell.

In one embodiment the host cell expressing a Vitamin K-dependent protein of interest comprises a siRNA construct targeting at least one protein contaminant expressed by the host cell, wherein the protein contaminant is a second vitamin K-dependent protein.

In one embodiment the host cell expressing a Vitamin K-dependent protein of interest comprises a siRNA construct targeting at least one protein contaminant expressed by the host cell, wherein the protein contaminant is Protein S.

The present invention also relates to a cell expressing a Vitamin K-dependent protein of interest comprising a disrupted gene for at least one protein contaminant expressed by the host cell.

In one embodiment the host cell has been modified by disruption by gene knock-out of at least one endogenous gene encoding a protein contaminant expressed endogenous by the host cell. In one embodiment the endogenous gene encoding Protein S has been disrupted by gene knock-out of exon 1.

In one embodiment the host cell expressing a Vitamin K-dependent protein of interest comprises a disrupted gene for at least one protein contaminant expressed by the host cell, wherein the protein contaminant is a second vitamin K-dependent protein.

In one embodiment the host cell expressing a Vitamin K-dependent protein of interest comprises a disrupted gene for at least one protein contaminant expressed by the host cell, wherein the protein contaminant is Protein S.

In one embodiment the host cell expressing a Vitamin K-dependent protein of interest comprises a disrupted gene for Protein S, wherein the Protein S gene is disrupted by omission of exon 1.

In one embodiment the host cell expressing a Vitamin K-dependent protein of interest has been modified by transfection with at least one transcription factor binding to a DNA element of the gene encoding the protein contaminant expressed endogenous by the host cell.

In one embodiment the host cell expressing a Vitamin K-dependent protein of interest has been modified by transfection with at least one nuclease fusion protein for site-specific cleavage of the DNA strands encoding the protein contaminant expressed endogenous by the host cell.

The present invention furthermore relates to a cell expressing a Vitamin K-dependent protein of interest comprising a transcription factor binding to at least one protein contaminant expressed by the host cell.

In one embodiment the host cell expressing a Vitamin K-dependent protein of interest comprising a transcription factor binding to the DNA sequence encoding at least one protein contaminant, the protein contaminant is a second vitamin K-dependent protein.

In one embodiment the host cell expressing a Vitamin K-dependent protein of interest comprises a transcription factor binding to the DNA sequence encoding at least one protein contaminant, the protein contaminant is Protein S.

In one embodiment of the invention the transcription factor is a Zinc finger protein. In one embodiment of the invention the Zinc finger protein binds a DNA element comprising the sequence of SEQ ID NO 35.

In one embodiment of the invention the Zinc finger protein binds the GGAGAGGAGGOGGGG DNA element.

In one embodiment the host cell expressing a Vitamin K-dependent protein of interest is modified by random mutagenesis for disruption of at least one endogenous gene encoding a protein contaminant expressed endogenous by the host cell.

The present invention also relates to a method for reducing the content of at least one protein contaminant in a composition comprising a Vitamin K-dependent protein of interest, wherein at least one protein contaminant expressed by the host cell is inhibited.

In one embodiment the method for reducing the content of at least one protein contaminant in a composition comprising a Vitamin K-dependent protein of interest, wherein at least one protein contaminant expressed by the host cell is inhibited is a method comprising the use of siRNA.

In one embodiment the method for reducing the content of at least one protein contaminant in a composition comprising a Vitamin K-dependent protein of interest, wherein at least one protein contaminant expressed by the host cell is inhibited is a method comprising the use of Random mutagenesis.

In one embodiment the method for reducing the content of at least one protein contaminant in a composition comprising a Vitamin K-dependent protein of interest, wherein at least one protein contaminant expressed by the host cell is inhibited is a method comprising the use of Targeted knock-out.

The present invention furthermore relates to a nucleic acid sequence comprising the CHO Protein S cDNA sequence having the sequence of SEQ ID NO 3 or any functional fragments thereof.

The present invention also relates to a nucleic acid sequence comprising the CHO Protein S coding sequence having the sequence of SEQ ID NO 4 or any functional fragments thereof.

The present invention relates to an amino acid sequence comprising CHO Protein S sequence having the sequence of SEQ ID NO 5 or any functional fragments thereof.

The methods and means described herein may in principle be applied for generating compositions comprising any Vitamin K-dependent protein of interest which is devoid or substantially devoid of protein contaminants.

"Polypeptides" means any protein comprising the amino acid sequence of the wild-type protein, as well as their respective "variants", "related polypeptides" "derivatives" and "conjugates" thereof.

In particular, as used herein, the terms "Factor VII polypeptide" or "FVII polypeptide" means any protein comprising the amino acid sequence 1-406 of wild-type human Factor VIIa (i.e., a polypeptide having the amino acid sequence disclosed in U.S. Pat. No. 4,784,950), variants thereof as well as Factor VII-related polypeptides, Factor VII derivatives and Factor VII conjugates. This includes FVII variants, Factor VII-related polypeptides, Factor VII derivatives and Factor VII conjugates exhibiting substantially the same or improved biological activity relative to wild-type human Factor VIIa.

The term "Factor VII" is intended to encompass Factor VII polypeptides in their uncleaved (zymogen) form, as well as those that have been proteolytically processed to yield their respective bioactive forms, which may be designated Factor Vita. Typically, Factor VII is cleaved between residues 152 and 153 to yield Factor VIIa.

Variants of Factor VII may exhibit different properties relative to human Factor VII, including stability, phospholipid binding, altered specific activity, and the like.

"Factor VII" or "Factor VIIa" within the above definition also includes natural allelic variations that may exist and occur from one individual to another. Also, degree and location of glycosylation or other post-translation modifications may vary depending on the chosen host cells and the nature of the host cellular environment.

As used herein, "wild type human FVIIa" is a polypeptide having the amino acid sequence disclosed in U.S. Pat. No. 4,784,950.

The term "Factor VII derivative" as used herein, is intended to designate a FVII polypeptide exhibiting substantially the same or improved biological activity relative to wild-type Factor VII, in which one or more of the amino acids of the parent peptide have been genetically and/or chemically and/or enzymatically modified, e.g. by alkylation, glycosylation, PEGylation, acylation, ester formation or amide formation or the like. This includes but is not limited to PEGylated human Factor VIIa, cysteine-PEGylated human Factor VIIa and variants thereof. Non-limiting examples of Factor VII derivatives includes GlycoPegylated FVII derivatives as disclosed in WO 03/31464 and US Patent applications US 20040043446, US 20040063911, US 20040142856, US 20040137557, and US 20040132640 (Neose Technologies, Inc.); FVII conjugates as disclosed in WO 01/04287, US patent application 20030165996, WO 01/58935, WO 03/93465 (Maxygen ApS) and WO 02/02764, US patent application 20030211094 (University of Minnesota).

The term "improved biological activity" refers to FVII polypeptides with i) substantially the same or increased proteolytic activity compared to recombinant wild type human Factor VIIa or ii) to FVII polypeptides with substantially the same or increased TF binding activity compared to recombinant wild type human Factor VIIa or iii) to FVII polypeptides with substantially the same or increased half life in blood plasma compared to recombinant wild type human Factor VIIa. The term "PEGylated human Factor VIIa" means human Factor Vila, having a PEG molecule conjugated to a human Factor VIIa polypeptide. It is to be understood, that the PEG molecule may be attached to any part of the Factor VIIa polypeptide including any amino acid residue or carbohydrate moiety of the Factor VIIa polypeptide. The term "cysteine-PEGylated human Factor VIIa" means Factor VIIa having a PEG molecule conjugated to a sulfhydryl group of a cysteine introduced in human Factor VIIa.

Non-limiting examples of Factor VII variants having substantially the same or increased proteolytic activity compared to recombinant wild type human Factor VIIa include S52A-FVIIa, S60A-FVIIa (Lino et al., Arch. Biochem. Biophys. 352: 182-192, 1998); FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); FVII variants as disclosed in PCT/DK02/00189 (corresponding to \NO 02/077218); and FVII variants exhibiting increased proteolytic stability as disclosed in WO 02/38162 (Scripps Research Institute); FVII variants having a modified Gla-domain and exhibiting an enhanced membrane binding as disclosed in WO 99/20767, U.S. Pat. No. 6,017,882 and U.S. Pat. No. 6,747,003, US patent application 20030100506 (University of Minnesota) and WO 00/66753, US patent applications US 20010018414, US 2004220106, and US 200131005, U.S. Pat. No. 6,762,286 and U.S. Pat. No. 6,693,075 (University of Minnesota); and FVII variants as disclosed in WO 01/58935, U.S. Pat. No. 6,806,063, US patent application 20030096338 (Maxygen ApS), WO 03/93465 (Maxygen ApS), WO 04/029091 (Maxygen ApS), WO 04/083361 (Maxygen ApS), and WO 04/111242 (Maxygen ApS), as well as in WO 04/108763 (Canadian Blood Services).

Non-limiting examples of FVII variants having increased biological activity compared to wild-type FVIIa include FVII variants as disclosed in WO 01/83725, WO 02/22776, WO 02/077218, WO 03/027147, WO 04/029090, WO 05/075635, and European patent application with application number 05108713.8 (Novo Nordisk A/S), WO 02/38162 (Scripps Research Institute); and FVIIa variants with enhanced activity as disclosed in JP 2001061479 (Chemo-Sero-Therapeutic Res Inst.).

Examples of variants of factor VII include, without limitation, P10Q-FVII, K32E-FVII, P10Q/K32E-FVII, L305V-FVII, L305V/M306D/D309S-FVII, L305I-FVII, L305T-FVII, F374P-FVII, V158T/M298Q-FVII, V158D/E296V/M298Q-FVII, K337A-FVII, V158D/M298Q-FVII, L305V/K337A-FVII, V158D/E296V/M298Q/L305V-FVII, V158D/E296V/M298Q/K337A-FVII, V158D/E296V/M128Q/L305V/K337A-FVII, K157A-FVII, E296V-FVII, E296V/M298Q-FVII, V158D/E296V-FVII, V158D/N1298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K3161-K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M2980/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/L158T/E296V/M298Q-FVII, K316H/1305V/V158T/K337A/M1298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/N1298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V15817E296V-FVII, F374Y/E296V/S314E-FVII, F374Y/S314E/M298Q/FVII, F374Y/E296V/M298Q-FVII, F374Y/L305V/K337A/V158D-FVII, F374Y/L305V/K337A/E296V-FVII, F374Y/L305V/K337A/M298Q-FVII, F374Y/L305V/K337A/V158T-FVII, F374Y/L305V/K337A/S314E-FVII, F374Y/L305V/V158D/E296V-FVII, F374Y/L305V/V158D/M298Q-FVII, F374Y/L305V/V158D/S314E-FVII, F374Y/L305V/E296V/M298Q-FVII, F374Y/L305V/E296V/V158T-FVII, F374Y/L305V/E296V/S314E-FVII, F374Y/L305V/M298Q/V158T-FVII, F374Y/L305V/M298Q/S314E-FVII, F374Y/L305V/V158T/S314E-FVII, F374Y/K337A/S314E/V158T-FVII, F374Y/K337A/S314E/M298Q-FVII, F374Y/K337A/S314E/E296V-FVII, F374Y/K337A/S314E/V158D-FVII, F374Y/K337A/V158T/M298Q-FVII, F374Y/K337A/V158T/E296V-FVII, F374Y/K337A/M298Q/E296V-FVII, F374Y/K337A/M298Q/V158D-FVII, F374Y/K337A/E296V/V158D-FVII, F374Y/V158D/S314E/M298Q-FVII, F374Y/V158D/S314E/E296V-FVII, F374Y/V158D/M298Q/E296V-FVII, F374Y/V158T/S314E/E296V-FVII, F374Y/V158T/S314E/M298Q-FVII, F374Y/V15817M298Q/E296V-FVII, F374Y/E296V/S314E/M298Q-FVII, F374Y/L305V/M298Q/K337A/S314E-FVII, F374Y/L305V/E296V/K337A/S314E-FVII, F374Y/E296V/M298Q/K337A/S314E-FVII, F374Y/L305V/E296V/M298Q/K337A-FVII, F374Y/L305V/E296V/M298Q/S314E-FVII, F374Y/V158D/E296V/M298Q/K337A-FVII, F374Y/V158D/E296V/M298Q/S314E-FVII, F374Y/L305V/V158D/K337A/S314E-FVII, F374Y/V158D/N1298Q/K337A/S314E-FVII, F374Y/V158D/E296V/K337A/S314E-FVII, F374Y/L305V/V158D/E296V/V1298Q-FVII, F374Y/L305V/V158D/M298Q/K337A-FVII, F374Y/L305V/V158D/E296V/K337A-FVII, F374Y/L305V/V158D/M298Q/S314E-FVII, F374Y/L305V/V158D/E296V/S314E-FVII, F374Y/V158T/E296V/M298Q/K337A-FVII, F374Y/V158T/E296V/M298Q/S314E-FVII, F374Y/L305V/V158T/K337A/S314E-FVII, F374Y/V158T/M298Q/K337A/S314E-FVII, F374Y/V158T/E296V/K337A/S314E-FVII, F374Y/L305V/V158T/E296V/M298Q-FVII, F374Y/L305V/V158T/M298Q/K337A-FVII, F374Y/L305V/V158T/

E296V/K337A-FVII, F374Y/L305V/V158T/M298Q/S314E-FVII, F374Y/L305V/V158T/E296V/S314E-FVII, F374Y/E296V/V298Q/K337A/V158T/S314E-FVII, F374Y/V158D/E296V/V298Q/K337A/S314E-FVII, F374Y/L305V/V158D/E296V/M298Q/S314E-FVII, F374Y/L305V/E296V/M298Q/V158T/S314E-FVII, F374Y/L305V/E296V/M298Q/K337A/V158T-FVII, F374Y/L305V/E296V/K337A/V158T/S314E-FVII, F374Y/L305V/M298Q/K337A/V158T/S314E-FVII, F374Y/L305V/V158D/E296V/V1298Q/K337A-FVII, F374Y/L305V/V158D/E296V/K337A/S314E-FVII, F374Y/L305V/V158D/M298Q/K337A/S314E-FVII, F374Y/L305V/E296V/M298Q/K337A/V158T/S314E-FVII, F374Y/L305V/V158D/E296V/M298Q/K337A/S314E-FVII, S52A-Factor VII, S60A-Factor VII; R152E-Factor VII, S344A-Factor VII, T106N-FVII, K143N/N145T-FVII, V253N-FVII, R290N/A292T-FVII, G291N-FVII, R315N/V317T-FVII, K143N/N145T/R315N/V317T-FVII; and FVII having substitutions, additions or deletions in the amino acid sequence from 233Thr to 240Asn; FVII having substitutions, additions or deletions in the amino acid sequence from 304Arg to 329Cys; and FVII haying substitutions, additions or deletions in the amino acid sequence from 153Ile to 223Arg.

Thus, substitution variants in a factor VII polypeptide include, without limitation substitutions in positions P10, K32, L305, M306, D309, L305, L305, F374, V158, M2.98, V158, E296, K337, M298, M298, S336, 5314, K316, K316, F374, S52, S60, R152, S344, T106, K143, N145, V253, R290, A292, G291, R315, V317, and substitutions, additions or deletions in the amino acid sequence from T233 to N240 or from R304 to C329; or from I153 to R223, or combinations thereof, in particular variants such as P10Q, K32E, L305V, M306D, D309S, L3051, L305T, F374P, V158T, M298Q, V158D, E296V, K337A, M298Q, M298K, S336G, S314E, K316H, K316Q, F374Y, S52A, S60A, R152E, S344A, T106N, K143N, N145T, V253N, R290N, A292T, G291N, R315N, V317T, and substitutions, additions or deletions in the amino acid sequence from T233 to N240, or from R304 to C329, or from I153 to R223, or combinations thereof.

"A Vitamin K-dependent protein of interest" as used herein refers to the single Vitamin K-dependent protein product produced by the host cells, which is relevant to obtain in the most pure form. In one embodiment vitamin K-dependent protein of interest is the protein product produced in the highest amount by the host cell. In one embodiment, the Vitamin K-dependent protein of interest in transfected into the host cell.

"Composition" as used herein, means any composition, such as a liquid composition, such as an aqueous liquid composition.

The Vitamin K-dependent protein of interest is most typically one produced under cell culture conditions, i.e. the Vitamin K-dependent protein of interest is either obtained directly as a constituent of a cell culture supernatant, or obtained from a cell culture supernatant after one or more subsequent purification process steps.

Typically, the total content of protein contaminants in the non-purified composition is at least 200 ppm, such as at least 300 ppm, e.g. at least 400 ppm, or at least 500 ppm. Also typically, the total content of Protein S contaminants in the non-purified composition is at least 200 ppm, such as at least 300 ppm, e.g. at least 400 ppm, or at least 500 ppm.

"Protein contaminant" and "protein contaminants" as used herein, means protein or polypeptide constituents produced endogenously by the host cell and constituting an impurity in relation to the Vitamin K-dependent protein of interest. Thus, the Vitamin K-dependent protein of interest is obviously not be counted as a protein contaminant.

"Devoid or substantially devoid" as used herein, refers to a composition wherein the total content of a protein contaminant in the composition is at the most 500 ppm, such as at the most 100 ppm, such as at the most 10 ppm, e.g. at the most 1 ppm, or at the most 0.1 ppm. Also typically, the total content of Protein S contaminants in the composition is at the most 500 ppm, such as at the most 100 ppm, such as at the most 10 ppm, e.g. at the most 1 ppm, or at the most 0.1 ppm.

The phrase "express a substantially lower amount of at least one protein contaminant" as used herein, refers to the expression level of an endogenous protein contaminant, which is reduced by at least 30%, such as by at least 40%, such as by at least 50%, such as by at least 60%, such as by at least 80%, such as by at least 90%, such as by at least 95%, such as by at least 99%.

A particularly relevant class of protein contaminant are proteins very similar to the Vitamin K-dependent protein of interest, such as any other protein containing a Gla-domain including the proteins: GAS-6, Protein S, Factor II (Prothrombin), Factor Xa, Factor IXa, Protein C, Factor VIIa, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Matrix Gla protein, and Osteocalcin.

As a non-limiting example, Protein S is sometimes seen as an impurity in the production of recombinant FVIIa in mammalian cells. Protein S is like FVII a Vitamin K-dependent plasma glycoprotein containing an EGF-like domain and a gamma-carboxy-glutamate (Gla) domain. Due to the structural similarity between FVII(a) and Protein S, it is difficult to recover FVII by means of chromatographic methods supra without contamination with Protein S. It would therefore be desirable to prevent the expression of Protein S by the host cell. This may be obtained by targeting the mRNA or the genome.

Stable expression of small interfering RNA, siRNA, is a new technology that enables reduction of targeted mRNA and thus suppression of targeted gene expression in mammalian cells (T, R. Brummelkamp, R. Bernards, and R. Agami. Science 296(5567): 550-553, 2002 & M. Mivaaishi and K Taira. Nat. Biotechnol 20(5):497-200, 2002.) A number of individual siRNA have been generated in a strategy similar to the ones described in the references. Some of these siRNAs have proven useful (Example 2).

The use of random mutagenesis to introduce genomic changes in the host cells, some of which may prevent the generation of mRNA in the host cell may also be exploited. This may be achieved by treating a population of CHO cells with a mutagen such as e.g. Ethyl Methane Sulfonate, EMS, which induces point mutations in the cells. The surviving cells may exhibit altered phenotypes, because of these mutations. The cells may be seeded in a screening format (e.g. 96-well plates) to allow isolation of clonal cell populations. Following a growth period, medium may be harvested from the wells and assayed for Protein S content. Clones without Protein S expression may be isolated and used for production of Protein S-free Factor VII.

Disruption of the genome may be obtained by gene targeting or the knock-out technique (Example 3). The generation of knock-out cells is a well-described technique for eradicating expression of endogenous proteins, and a CHO knock-out cell was recently described in Yamane-Ohnuki et al. Biotechnol. Bioeng. 87 (5):614-622, 2004.

Genomic Protein S knockout plasmid was generated and transfected into CHO cells. By homologous recombination the Protein S gene in the CHO cells was disrupted. This procedure was repeated until all alleles of the Protein S gene was stably removed (Example 3).

Transcription factor engineering for transcriptional down regulation is an alternative way of modifying the gene expression (Example 4).

These methods may in theory be suitable for removing any unwanted host cell protein contaminants. For all of these methods to be applied it requires the knowledge of the gene sequence of the contaminating protein. The sequence of Protein S for Chinese Ovary Hamster, CHO, is not public available and a cloning of CHO Protein S cDNA was performed as described in Example 1 and disclosed as SEQ ID NO 1. The CHO Protein S coding sequence and the CHO Protein S amino acid sequence are disclosed as SEQ ID NO 2 and 3 respectively.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EMBODIMENTS OF THE INVENTION

1. A composition comprising a Vitamin K-dependent protein of interest devoid or substantially devoid of at least one protein contaminant expressed by a host cell.
2. The composition according to embodiment 1, wherein the Vitamin K-dependent protein of interest is selected from the group consisting of GAS-6, Protein S, Factor II (Prothrombin), Factor X, Factor IX, Protein C, Factor VII, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Bone Gla protein, Matrix Gla protein, and Osteocalcin.
3. The composition according to embodiment 1, wherein at least one of said protein contaminants is a vitamin K-dependent protein.
4. The composition according to embodiment 1, wherein at least one of said protein contaminants is Protein S.
5. The composition according to embodiment 1, wherein the host cell is selected from the group consisting of CHO cells, 293 (HEK293) cells, BKH cells, HKB11 cells, SP2/0 cells, and NS0 cells.
6. A cell expressing a Vitamin K-dependent protein of interest according to any of embodiments 1-5 further comprising a siRNA construct targeting at least one protein contaminant expressed by the host cell.
7. The cell according to embodiment 6, wherein said at least one protein contaminant is a vitamin K-dependent protein.
8. The cell according to any of embodiments 6-7, wherein said at least one protein contaminant is Protein S.
9. A cell expressing a Vitamin K-dependent protein of interest according to any of embodiments 1-5 further comprising a disrupted gene for at least one protein contaminant expressed by the host cell.
10. The cell according to embodiment 9, wherein said at least one protein contaminant is a vitamin K-dependent protein
11. The cell according to any of embodiments 9-10, wherein said at least one protein contaminant is Protein S.
12. The cell according to any of embodiments 9-11, wherein the Protein S gene is disrupted by omission of exon 1
13. A cell expressing a Vitamin K-dependent protein of interest according to any of embodiments 1-5 further comprising a transcription factor binding to at least one protein contaminant expressed by the host cell.
14. The cell according to embodiment 13, wherein said at least one protein contaminant is a vitamin K-dependent protein
15. The cell according to any of embodiments 13-14, wherein said at least one protein contaminant is Protein S.
16. The cell according to any of embodiments 13-15, wherein the transcription factor is a Zinc finger protein.
17. The cell according to any of embodiments 15-16, wherein the Zinc finger protein binds the GGAGAGGAGGGGGGG DNA element.
18. A method for reducing the content of at least one protein contaminant in a composition comprising a Vitamin K-dependent protein of interest wherein at least one protein contaminant expressed by the host cell is inhibited
19. The method according to embodiment 18, wherein the method comprises the use of siRNA.
20. The method according to embodiment 18, wherein the method comprises the use of Random mutagenesis.
21. The method according to embodiment 18, wherein the method comprises the use of Targeted knock-out.
22. A nucleic acid sequence comprising the CHO Protein S cDNA sequence having the sequence of SEQ ID NO 1.
23. A nucleic acid sequence comprising the CHO Protein S coding sequence having the sequence of SEQ ID NO 2.
24. An amino acid sequence comprising CHO Protein S sequence haying the sequence of SEQ ID NO 3.

Further Embodiments of the Invention

1a. A host cell expressing a Vitamin K-dependent protein of interest, said host cell being modified to express a substantially lower amount of at least one protein contaminant expressed endogenous by said host cell in the absence of said modification.
2a. The host cell according to embodiment 1a, wherein said Vitamin K-dependent protein of interest is selected from the group consisting of GAS-6, Protein S, Factor II (Prothrombin), Factor X, Factor IX, Protein C, Factor VII, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Bone Gla protein, Matrix Gla protein, and Osteocalcin.
3a. The host cell according to any one of embodiments 1a-2a, wherein said protein contaminants is a second vitamin K-dependent protein.
4a. The host cell according to any one of embodiments 1a-3a, wherein said protein contaminant is Protein S.
5a. The host cell according to any one of embodiments 1a-4a, wherein the host cell is selected from the group consisting of CHO cells, 293 (HEK293) cells, BKH cells, HKB11 cells, SP2/0 cells, and NS0 cells.
6a. The host cell according to any one of embodiments 1a-5a, wherein said cell has been modified by transfection with at least one siRNA polynucleotide construct targeting a mRNA encoding a protein contaminant expressed endogenous by said host cell.
7a. The host cell according to any one of embodiments 1a-6a, wherein said cell has been modified by disruption by gene knock-out of at least one endogenous gene encoding a protein contaminant expressed endogenous by said host cell.

8a. The host cell according to embodiment 7a, wherein the endogenous gene encoding Protein S has been disrupted by gene knock-out of exon 1.

9a. The host cell according to any one of embodiments 1a-8a, wherein said cell has been modified by transfection with at least one transcription factor binding to a DNA element of the gene encoding said protein contaminant expressed endogenous by said host cell.

10a. The host cell according to embodiment 9a, wherein said transcription factor is a Zinc finger protein.

11a. The host cell according to embodiment 10a, wherein said Zinc finger protein binds a DNA element comprising the sequence of SEQ ID NO 35.

12a. The host cell according to any one of embodiments 1a-11a, wherein said cell has been modified by random mutagenesis for disruption of at least one endogenous gene encoding a protein contaminant expressed endogenous by said host cell.

13a. A method for producing a host cell according to any one of embodiments 1a-12a, said method comprising the following steps in any order:

a) optionally transfecting said cell with a polynucleotide construct encoding a Vitamin K-dependent protein of interest; and b) modifying said cell to express a substantially lower amount of at least one protein contaminant expressed endogenous by said host cell in the absence of said modification.

14a. The method according to embodiment 13a, wherein said Vitamin K-dependent protein of interest is selected from the group consisting of GAS-6, Protein S, Factor II (Prothrombin), Factor X, Factor IX, Protein C, Factor VII, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Bone Gla protein, Matrix Gla protein, and Osteocalcin.

15a. The method according to any one of embodiments 13a-14a, wherein said protein contaminants is a second vitamin K-dependent protein.

16a. The method according to any one of embodiments 13a-15a, wherein said protein contaminant is Protein S.

17a. The method according to any one of embodiments 13a-16a, wherein the host cell is selected from the group consisting of CHO cells, 293 (HEK293) cells, BKH cells, HKB11 cells, SP2/0 cells, and NS0 cells.

18a. The method according to any one of embodiments 13a-17a, wherein said cell has been modified by transfection with at least one siRNA polynucleotide construct targeting a mRNA encoding a protein contaminant expressed endogenous by said host cell.

19a. The method according to any one of embodiments 13a-18a, wherein said cell has been modified by disruption by gene knock-out of at least one endogenous gene encoding a protein contaminant expressed endogenous by said host cell.

20a. The method according to embodiment 19a, wherein the endogenous gene encoding Protein S has been disrupted by gene knock-out of exon 1.

21a. The method according to any one of embodiments 13a-20a, wherein said cell has been modified by transfection with at least one transcription factor binding to a DNA element of the gene encoding said protein contaminant expressed endogenous by said host cell.

22a. The method according to embodiment 21a, wherein said transcription factor is a Zinc finger protein.

23a. The method according to embodiment 22a, wherein said Zinc finger protein binds a DNA element comprising the sequence of SEQ ID NO 35.

24a. The method according to any one of embodiments 13a-23a, wherein said cell has been modified by random mutagenesis for disruption of at least one endogenous gene encoding a protein contaminant expressed endogenous by said host cell.

25a. A method for producing a composition comprising a Vitamin K-dependent protein of interest with a substantially lower amount of at least one protein contaminant expressed endogenous by said host cell in the absence of modification, said method comprising the steps of:

a) producing a host cell according to any one methods of embodiments 13a-24a; and b) growing said host cell in a growth medium and harvesting said growth medium comprising said Vitamin K-dependent protein of interest.

26a. A composition produced by the method according to embodiment 25a.

27a. A nucleic acid sequence comprising the sequence of SEQ ID NO 1.

28a. A nucleic acid sequence comprising the sequence of SEQ ID NO 2.

29a. An amino acid sequence comprising the sequence of SEQ ID NO 3.

EXAMPLES

Example 1

Cloning of CHO Protein S cDNA

The Chinese Hamster Ovary, CHO, Protein S cDNA sequence was not known from any nucleotide or protein database but was expected to have high identity to the nucleotide sequence of Protein S from other rodents.

CHO Protein S PCR fragments were generated from CHO cDNA using primers designed from alignment between mouse and rat Protein S cDNA sequences or genomic sequences. The cDNA fragments were sequenced and assembled to form a full-length coding sequence for the CHO Protein S gene. The full-length CHO Protein S cDNA was cloned by PCR using the primers "CHO ProtS forward" and "CHO ProtS reverse" and CHO K1 derived cDNA as template.

The predicted CHO Protein S amino acid sequence has 90.5% identity to mouse Protein S and 90.7% identity to rat Protein S.

```
CHO ProtS forward (SEQ ID NO 1):
5'-GCCCAGGCTCGCAGCTCCTCTGG-3'

CHO ProtS reverse (SEQ ID NO 2):
5'-CAGGTGACACCTGCCAGCTGGTG-3'

CHO Protein S cDNA sequence (SEQ ID NO 3):
gcccaggctcgcagctcctctgggcggagcgccggctcggtccccg
ctgcgccagccgtgatccccggcagcctgctcagcaatgagggtcc
tgagcgcgcgctgtcggctactgctggtatgcctagccctggtgct
gccagcctcggagacaaactttttgtcaaaagaacatgcctcgcaa
gtcctggtgaggaagcgccgcgcaaataccttgcttgaagaaacta
aaaagggcaatcttgaaagagaatgcatcgaagagctctgcaataa
agaggaagccagggaggtctttgaaaacaatcccgaaacggattat
ttttatccaaaatatttgggttgtctgggcatgttccgtgctggcc
tgttcagtgctgcgcggcagtctgttaatgcttaccccgacctcag
gagctgtgtcaatgccatcccagaccaatgtgatcctatgccatgc
aatgaagatgggtatctgagctgcaaagatggccaagctgctttca
catgcatctgcaaaccaggatggcaaggggacaaatgccagtttga
tgtaaatgaatgtaaagatcccttaaatgtaaatgggggctgcagc
cagatttgtgacaacactcctggaagttaccactgctcctgcagaa
gtggctttgctatgctttcaaacaaaaaagactgcaaagatgtgga
```

-continued

```
tgaatgctctatgaagcccagtgtttgtggctcagctgtgtgcaag
aacactccaggagactatgagtgtgaatgtcctgacggctacagat
atgatccctcatcgaagtcttgcaaagatgtggacgaatgctctga
gaacatgtgtgctcaattgtgtgtcaattaccctggaggctactct
tgttactgtgatggaaagaaaggattcaagcttgcccaagatcaga
agagttgtgagggtattccagtgtgccttcccttgaaccttgacaa
aaattatgaattattgtacttggctgagcagtttgtaggagttgtc
ttatatctgaaatttcgtttgccagaaattaccagattttcagctg
aatttgattttcggacatatgattcagagggcatcatcctgtatgc
agaatctcttgatcactcaaattggctcctgattgcacttcgtgat
ggaaaaattgaagttcagtttaagaatgagttttcaacccaaatca
caaccggaggcaatgttattaacaatggtaaatggaacatggtatc
cgtggaagaattagacgacagtgttagcattaaaatagctaaagaa
gctgtgatgaatataaataaatttgggagcctctttaaacctacag
atggatttctggacaccaaaatatactttgcaggattacctcgggt
agtggaaagtgcactcattaaaccgattaaccctcgtctggatgga
tgtatacgaggctggaacttgatgaaacaaggagctttaggtgcaa
aggaaattattcaaggaaaacaaaataagcattgcttcctcatggt
ggagaagggctcctactaccctggttctggaattgctcggttcagc
atagattacaataatgtaaccaatgcagagggctggcaaataaatg
tgaccttgaatattcgtccatccactggcactggaattatgcttgc
cttggtttctggagacaaagtgccctttgccttgtccttggtgggc
tccagctctgaaaattctcaggatattgtggtatttgttgaaaatt
cagtggtggctcgaatggaggccataactctgtgttctgaccagca
atcccaactgaaatgtaatgttaacagacatggcctagagctatgg
agcccactgaagaaagatgtcatctactctaaagatattcaaggac
aactagcagtcttggacaaagcaatgaaaggaaacgtggccactta
tctgggtggcattccagatctttccttcagtgccacgccagtgaat
gccttctacagtggctgcatggaagtgaacatcaacggggtgcagt
tggatctggatgaagccatttctaaacataatgacatcagagctca
ctcatgtccttcagttaagaaaatccagaagaacgtctaatgtctg
ttttctgtgcttataatgcccctttccttgtaattatgctcacgcc
cctatcaccagctggcaggtgtcacctgtgaagtgcaatgtttgaa
atgatgtggtactttgtccttcagattttgttatataaaccacgt
tttttttttttttttaaagtctttcttctattgctgtctagaaatt
aaataa
```

CHO Protein S coding sequence (SEQ ID NO 4):

```
atgagggtcctgagcgcgcgctgtcggctactgctggtatgcctag
ccctggtgctgccagcctcggagacaaacttttttgtcaaaagaaca
tgcctcgcaagtcctggtgaggaagcgccgcgcaaataccttgctt
gaagaaactaaaaagggcaatcttgaaagagaatgcatcgaagagc
tctgcaataaagaggaagccagggaggtctttgaaaacaatcccga
aacggattattttatccaaaaatatttgggttgtctgggcatgtt
ccgtgctggcctgttcagtgctgcgcggcagtctgttaatgcttac
cccgacctcaggagctgtgtcaatgccatcccagaccaatgtgatc
ctatgccatgcaatgaagatgggtatctgagctgcaaagatggcca
agctgctttcacatgcatctgcaaaccaggatggcaaggggacaaa
tgccagtttgatgtaaatgaatgtaaagatcccttaaatgtaaatg
gggctgcagccagatttgtgacaacactcctggaagttaccactg
ctcctgcagaagtggctttgctatgctttcaaacaaaaaagactgc
aaagatgtggatgaatgctctatgaagcccagtgtttgtggctcag
ctgtgtgcaagaacactccaggagactatgagtgtgaatgtcctga
cggctacagatatgatccctcatcgaagtcttgcaaagatgtggac
gaatgctctgagaacatgtgtgctcaattgtgtgtcaattaccctg
gaggctactcttgttactgtgatggaaagaaaggattcaagcttgc
ccaagatcagaagagttgtgagggtattccagtgtgccttcccttg
aaccttgacaaaaattatgaattattgtacttggctgagcagtttg
taggagttgtcttatatctgaaatttcgtttgccagaaattaccag
attttcagctgaatttgattttcggacatatgattcagagggcatc
atcctgtatgcagaatctcttgatcactcaaattggctcctgattg
cacttcgtgatggaaaaattgaagttcagtttaagaatgagttttc
aacccaaatcacaaccggaggcaatgttattaacaatggtaaatgg
aacatggtatccgtggaagaattagacgacagtgttagcattaaaa
tagctaaagaagctgtgatgaatataaataaatttgggagcctctt
taaacctacagatggatttctggacaccaaaatatactttgcagga
ttacctcgggtagtggaaagtgcactcattaaaccgattaaccctc
gtctggatggatgtatacgaggctggaacttgatgaaacaaggagc
tttaggtgcaaaggaaattattcaaggaaaacaaaataagcattgc
ttcctcatggtggagaagggctcctactaccctggttctggaattg
ctcggttcagcatagattacaataatgtaaccaatgcagagggctg
gcaaataaatgtgaccttgaatattcgtccatccactggcactgga
attatgcttgccttggtttctggagacaaagtgccctttgccttgt
ccttggtgggctccagctctgaaaattctcaggatattgtggtatt
tgttgaaaattcagtggtggctcgaatggaggccataactctgtgt
tctgaccagcaatcccaactgaaatgtaatgttaacagacatggcc
tagagctatggagcccactgaagaaagatgtcatctactctaaaga
tattcaaggacaactagcagtcttggacaaagcaatgaaaggaaac
gtggccacttatctgggtggcattccagatctttccttcagtgcca
cgccagtgaatgccttctacagtggctgcatggaagtgaacatcaa
cggggtgcagttggatctggatgaagccatttctaaacataatgac
```

-continued

```
atcagagctcactcatgtccttcagttaagaaaatccagaagaacg
tctaa
```

CHO Protein S amino acid sequence (SEQ ID NO 5):

```
mrvlsarcrlllvclalvlpasetnflskehasqvlvrkrrantll
eetkkgnlerecieelcnkeearevfennpetdyfypkylgclgmf
raglfsaarqsvnaypdlrscvnaipdqcdpmpcnedgylsckdgq
aaftcickpgwqgdkcqfdvneckdplnvnggcsqicdntpgsyhc
scrsgfamlsnkkdckdvdecsmkpsvcgsavckntpgdyececpd
gyrydpssksckdvdecsenmcaqlcvnypggyscycdgkkgfkla
qdqkscegipvclplnldknyellylaeqfvgvvlylkfrlpeitr
fsaefdfrtydsegiilyaesldhsnwllialrdgkievqfknefs
tqittggnvinngkwnmvsveelddsvsikiakeavmninkfgslf
kptdgfldtkiyfaglprvvesalikpinprldgcirgwnlmkqga
lgakeiiqgkqnkhcflmveksgsyypgsgiarfsidynnvtnaeg
wqinvtlnirpstgtgimialvsgdkvpfalslvgsssensqdivv
fvensvvarmeaitlcsdqqsqlkcnvnrhglelwsplkkdviysk
diqgqlavldkamkgnvatylggipdisfsatpvnafysgcmevni
ngvqldldeaiskhndirahscpsvkkiqknv
```

Example 2

CHO Protein S mRNA Degradation by Use of Small Interfering RNA

The mRNA of Protein S in Chinese Hamster Ovary (CHO) cells can be degraded by the introduction of small interfering RNA, siRNA, into the cells. siRNA is a short double-stranded RNA molecule that may separate inside the cell and the antisense part of the molecule may hybridize to a complementary mRNA and induce cleavage of this mRNA by a process in which the Dicer nuclease plays a key role. The effect of siRNA is described in Elbashir-S M et al., Nature 411 (2001) 494-498. siRNA may be synthesized as single-stranded RNA and subsequently annealed to form the double-stranded siRNA molecule. The siRNA molecule may subsequently be transiently transfected into cells and exert its function. Alternatively, siRNA may be expressed as a hairpin molecule under regulation of a Polymerase III promoter as described in Brummelkamp T R; Bernards R; Agami R, *Science* 296 (2002) 550-553.

A vector that permits the transcription of each of two complementary strands by individual promoters was developed in our laboratory. The vector is called RansiRNA because random DNA can be inserted into it and both strands of the insert can be transcribed. The RansiRNA vector contains the human H1 polymerase III promoter and the mouse U6 polymerase III promoter. The two promoters are pointed towards the siRNA template from each direction, transcribing the sense and antisense strand of the siRNA molecule, respectively. The vector also harbors the hygromycin drug resistance gene. The RansiRNA vector is similar, but not identical, to the pHippy vector described by Kaykas & Moon (Kaykas-A & Moon-R T, BMC Cell Biology Vol. 5 (1) pp. 16 (2004).

Several target siRNA sequences were selected from the CHO Protein S coding sequence, only targets containing the sequence $AGN_{17}CT$ (SEQ ID NO 6) were chosen. Each target sequence were purchased as two complementary DNA oligonucleotides extended with A's 5' to the target and T's 3' the target which serve as termination signal when transcribed in reverse and forward direction. The oligonucleotides also harbor a four base-pair 5'-overhang which is compatible with the Bgl II restriction site (GATC). The annealed oligonucleotides are cloned into the BglII-site of the RansiRNA-hygro vector.

The specified siRNA constructs were stably transfected into a CHO K1 cell line expressing a human FVII analogue. Cells were plated in 6-well plates at density of $2\times10^5$ c/well in complete medium (DMEM medium containing 10% FBS, non-essential amino acids and vitamin K). After two days the cells were transfected at 90% confluency. Transfection using Lipofectamine-2000 (Invitrogen) was performed according to recommendations from the manufacturer. After 48 hours the cells were transferred to selection medium, which was composed of complete medium additionally supplemented with 300 ug/ml hygromycin. After selection for 14 days, cells were cloned by limiting dilution. After clones had grown up the FBS containing complete medium was changed to serum free medium (PF CHO supplemented with vitamin K, Hyclone) in order to avoid detection of bovine protein S in the following ELISA. The supernatant from approximately 100 clones for each siRNA construct were screened by protein S ELISA using human protein S as standard. The same supernatant was also screened by a human FVII ELISA. The clones that had the lowest expression of protein S and that had not lost the expression of FVII were further characterized. Clones that had down regulated the expression of protein S to the level of only 10% of the expression level exhibited by the parental CHO K1 FVII expressing cell line were isolated.

sRNA Target Sequences

```
#821 siRNA1 target (SEQ ID NO 7):
5'-agtgtgaatgtcctgacggct-3'

#821 siRNA1 upper oligo (SEQ ID NO 8):
5'-gatctaaaaaagtgtgaatgtcctgacggctttttta-3'

#821 siRNA1 lower oligo (SEQ ID NO 9):
5'-gatctaaaaaagccgtcaggacattcacacttttta-3'

#822 siRNA2 target (SEQ ID NO 10):
5'-agctgcaaagatggccaagct-3'

#822 siRNA2 upper oligo (SEQ ID NO 11):
5'-gatctaaaaaagctgcaaagatggccaagctttttta-3'

#822 siRNA2 lower oligo (SEQ ID NO 12):
5'-gatctaaaaaagcttggccatctttgcagcttttta-3'

#835 siRNA4 target (SEQ ID NO 13):
5'-agaacatgcctcgcaagtcct-3'

#835 siRNA4 upper oligo (SEQ ID NO 14):
5'-gatctaaaaaagaacatgcctcgcaagtccttttta-3'

#835 siRNA4 lower oligo (SEQ ID NO 15):
5'-gatctaaaaaaggacttgcgaggcatgttcttttta-3'

#836 siRNA5 target (SEQ ID NO 16):
5'-agaaactaaaaagggcaatct-3'

#836 siRNA5 upper oligo (SEQ ID NO 17):
5'-gatctaaaaaagaaactaaaaagggcaatcttttta-3'

#836 siRNA5 lower oligo (SEQ ID NO 18):
5'-gatctaaaaaagattgccctttttagtttcttttta-3'

#837 siRNA6 target (SEQ ID NO 19):
5'-agccagatttgtgacaacact-3'

#837 siRNA6 upper oligo (SEQ ID NO 20):
5'-gatctaaaaaagccagatttgtgacaacactttttta-3'

#837 siRNA6 lower oligo (SEQ ID NO 21):
5'-gatctaaaaaagtgttgtcacaaatctggcttttta-3'
```

Example 3

Gene Targeting of CHO Protein S

A definitive way of abolishing protein expression of Protein S is to disrupt the gene. The technique of "gene targeting" or "gene knock-out" in mice has been known for many years. Gene targeting in cultured cells is also well established, and an example of a CHO knock-out cell was recently described in Yamane-Ohnuklet et al. Biotechnology and Bioengineering, 87(5): 614-622, 2004.

We predicted the exon structure of the CHO Protein S gene by an alignment of the CHO Protein S cDNA to the human gene. Primers designed to bind in exon 1 and exon 2 of CHO Protein S was used in a Polymerase Chain Reaction, PCR, the template was CHO genomic DNA. The amplified 4.4 kb product was sequenced, Primers binding exon 2 and exon 3 was used to PCR amplify intron 2. An amplified fragment of 3.5 kb harboring intron 2 was cloned and sequenced.

The regions upstream of exon 1 from mouse and rat Protein S were aligned and sequence stretches with high identity were used to design oligonucleotide primers for use in PCR. A 1650 bp 5'UT/promoter band was cloned and sequenced. The gene targeting construct will combine the "1.6 kb 5' UT/promoter fragment", "Plox-PGK-hygromycin resistance gene-Plox", "intron 1", "exon 2" and "PGK-TK". This construct is omitting the coding sequence from exon 1 in CHO Protein S, encoding the amino acids MRVLSVRCRLLLVCLALVL-PASETN (SEQ ID NO 22). A second construct containing the blasticidin drug resistance gene can be made in a similar way.

The "hygromycin"-gene targeting construct can electroporated into CHO cells and cells plated in dishes. The next days the cells are exposed to 600 microg/ml hygromycin and 1 micromolar ganciclovir. The clones are now selected for hygromycin resistance gene and against herpes simplex thymidine kinase gene. After colonies appeared they will be transferred to 96 wells plates. The cells grow to confluence and duplicates of the plates will be made. Genomic DNA is harvested from the cell clones and PCR-reactions using a hygromycin resistance gene specific primer and a primer 3' the promoter present in the construct are performed. Clones with a positive PCR-band are grown in flasks and a Southern blot will be made to verify the PCR result.

Second, the targeting construct harboring the blasticidin resistance gene are electroporated into the hemizygous CHO cells whereafter the cells are selected for the blasticidin resistance gene and against thymidine kinase gene using 10 microg/ml blasticidin and 1 micro-molar ganciclovir. Again, cell clones are PCR verified using a blasticidin resistance gene specific primer and a primer 3' to the promoter present in the construct. Positive clones are again tested by Southern blots.

Homozygous disruptants are transfected with a Cre recombinase expressing plasmid. Cre recombinase will recombine the lox sites and remove the drug-resistance genes.

```
Intron 1 primers:
CHO-protein-S-exon1-forw2 (SEQ ID NO 23):
5'-CTGCTGGTATGCCTAGCCCTGGTG-3'

CHO-protein-S-exon2-rev2 (SEQ ID NO 24):
5'-TGCAGAGCTCTTCGATGCATTCTC-3'

Intron 2 primers:
CHO-protein-S-exon2-forw2 (SEQ ID NO 25):
5'-AAGGGCAATCTTGAAAGAGAATGC-3'

CHO-protein-S-exon3rev (SEQ ID NO 26):
5'-CCAAATATTTTGGATAAAAATAATC-3'

5'UT/promoter primers:
PS-CHO promoter f2 (SEQ ID NO 27):
5'-AARCAACCCCTTTTGACCAT-3'

CHO-protein-S.promoterRev1 (SEQ ID NO 28):
5'-CCCAGAGGAGCTGCGAGCCTG-3'
```

-continued

5'UT/promoter (immediately 5' to coding sequence) (SEQ ID NO 29):
aarcaacccctttttgaccatacacatttctactctttgtgtttgct
ggagctgttttctccccacactcaaccccctttgctgaagcctgga
acttgctttccacagcttaagttgttataggtttcaatcatctgtc
cacctccctgactttcataattttgtgaaatacccttgcatatata
tatgggactaaatattatttttctcctggttgtccataatagattaa
tttaattcctaaacaaagaacagaacatagattggtatagtagaag
agtttcccttctccctactgcatgaatggaaattccccaaaccatc
cttatcagagaaattaactcacatactagtcacctttcattcagct
ggatgacaaaatcattttaaaaaaagagaataaagaaaacagataa
gaacaactagatctaggaataatacttaaaatatgattctgcttag
taggtttcattcacacacctagaaaaaaaaatcagtcaatgtttcc
tttgggcagaaaatgagcaataatgggtatgcattgaccactactg
ttggacatagccttattgcttcatatagcatctattcaaagtctca
gatcaacactatgaaaacctgtcatctctgtattagatgatgtgac
tggggctgtaaagggtaagctcttttcttacagctatacaacaacg
ctaagaccaagttctgtgctttgagcccaggcagtttagtttccca
ggagcaacctaaagcctgattcacaggcatatgtatgatccaaact
gaatggtagtacatcaataccaaaacaatctattggtggaaacaca
ccataggtgatcgaaatactccattttcttttcctctcatgacttc
tgttctgagcagtcctcttcctaaagtctacattgtcttctgagtt
caggctgacatcttgacatcctcctggctggcacagtctctggaca
aggagggaagaaggagagaaggggaaagggagaggaggggggggagg
gagagaaagaatgggaagaggaaggatatgaaagagagaagagagg
agggaaggcgggaggaagggagggagggagggagggagagagggag
agagaggagagagagagagagagagagagagagagagagagagaga
gagagagagagagagagggagagggagagagagacagagagagaga
gagggagagggagagagagagagagagagagagagagagagagaga
gagagagagtgaggagagagagagagagagttttcttcaccattggac
attcctaaagaaaagaagtaaatgcaggattggggacagtgacaga
ggacctctgataaactttctgaggcctctgacctcactctctcgga
gccctcctccaccacccacccccccccctccctagctgagaaaagct
tccaggaaatgtcccagtcatcgcttcccctcccgggctgggggct
gggagcgggcggtcccctcaggccagggctgctccggccgcgctcg
ggcagggccacaacagagctgggaaagctgagcccaggctcgcagc
tcctctgggcggagcgccggctcggtccccgctgcgccagccgtga
tccccggcagcctgctcagca exon1 (SEQ ID NO 30):
atgagggtcctgagcgtacgctgtcggctactgctggtatgcctag
ccctggtgctgccagcctcggagacaaac inton1 (SEQ ID NO 31):
tgtaagtaatccatacctcctggcttctccattccctatgtgcccc
ggcttgaagattttccactaggctgtttgctgcctcctaagtttcc
agtaagtccgccaccattcagagagtcgcggcagcctgggtctggt
gggcagtgtaaaggtgggacaggatcaaagcttgccttgctttgag
aaccattgtccacaggacttgattccagaacccgggtgacactaag
tgtcaaaggaattgcttgaacatagtcctaaatattgctaggaaag
ctaagtcaagcctgttgccctcctcccgtttacaagagtgccccag
cccgcaccctctcctgcggctaaccttccttttgcaatttctggac
tttgaacttgattgactggtctcacattgacaaactgtttggggac
tgctggggtgttacatatgattctctaaccttgatataagaaatag
ctgttggatgttaccttgtaccgaggatcattttctgagggttttg
actgttgccgctttgagatggcagcaagaattctgtacaacacaca
catttttgtgtttcttggtctttcctcttcccattctcagattccg
ggcagtatatcgagttttctcttagaaatataaaacgaaccacaag
gttttagtacattttaatggtcaattaaattgtttttagaagctta
aatatgttcataattaacactgctttcttttgctcttttgtagtcc
cagtcactggcatgggagcaataactgtataacaaataccacttag
gtcactgcgagcaccaaagaaacttttcaaagatggtaattaagta
ggagtttgctggaattgcaagtttttattaattagtaaggaatcta
gcctgatatttttaaatgtctaactaagttaaagaccagaatgaaa
ctggttcacttttttattgaggataaacaagttacagttataaagcc
tcaacaatcaaagccctacgatgaagcagcgtgtgactgtatgcac
atgatctatcttgttcagaggaacaatcaaacattttcagatagca
tcagggcggtggtggtactcgcctataatcctagcaaagtcagagg
caagcagatctctgtgttcaaggccagcctagtctacagagtgagt
tccaggacaactggggctacacagagaaacctgtctcagagaaaaa
caaaataaaaccaaattcagatagctggtgtttgggaaaagagcaa
aagacagcagtgctggcccacacagagagtagacaagttcattctac
aaggacatcacagaaagaatatgtgacccaatgacgaccataaact
ttcttgttcctgtgtcaaattatctccggtttattgatgaagaacc
agacactatgagctgcgtctcctccttaagattttgttttggtgtc
ttgtttttgtcaaggggtttcattgtggccctgagcattagatcca
gggctttgtgcatgctaggccagggagctatattcccgaactccag
aagactaggaatttgagatataaatagaatttgaattaccttctgt
acaattgattgtatggttctagaaatattgctatattaagggaagc
ctttgcagaagacagttattttgagatggtgcataacacaaaagaa
atgaactaaagcctgaggcctgctctgtagctctgccttgccctta
gcctacaataactttctttacctttcaagcatgtgccaccacgcct
gactttcaggcccttcattttaacaagaaagcaagtattcagttat
caactgactttccaaatgcatttgtatgaataaaaactacaaaaat
ataaaaataagaactatacacacaaaagccttgtatttaaaattta
cgctgtggacatattttgctcatcattcgtgagagcttgcggtaaa
aaggcaaaggggaagaggaggatatctattttgggtaggctaattt
ggccttatccagacttccctttttgggtggatgcagtctgcccagca
cactattggcccatttcttctacatggctttgtgctctgctctgcc
cttagctaattgtcccctttgacatgcttttgtctttccttaaagt
ttctatacttcaaaaaccatcccgctacactaatggagtgattttc
tcaagggttgctttatgtttggggtttgtactgcaagagttagttt
ctgatatagcaatggtgatagtatagtcttctaccatgaactctat
gccagcaagtacaggggtatatttcacatgggtgttttctgttcac
tgagtttcatgtcttctttgtatctttttgttttgttttgtgagac
agggtttctctgtagcttttgagtcagtcctggaacttgctggccg
gccttgaactcacagagattcacctgcctctgcctcccaagtgctg
ggatttaaggtgtgagtcaccactgccaggtttttttctttgtatct
tgagtgaactaaataggtaagctttaaataataatatgagcagtct
atttatatacattaaatattaaatgcattgtgagatgagcatagcc
tttgaggcccaggaacagaaagatttacttcacattgtaaatatac
tggtatacatacaaacgtacatacnnnnnngtgtgtgtgtgtgtgt
gtgtgtgtgtgtgcatgccatagcacacatgtgaagtccagagtac
agcattctctttttctacctttctgtagattcttgtggtcagagtc
aggtcaaatcaaatcagacagatgcatgtataaaatgctcttaccc
actgaaccatcttgctgcttggtccacaagcttagtggaagaatgc
tgggaagtgaatagtatgtttttaaatgtagttaaccttgactttt
tgttgttgttgctgttattgaggccacattttcattgttctgagaa
aatattactattttcctcagacagaattatatatttatttgaagtt
catgaattccatattattttcctgtatttattacaaatagcatgct
taaacacttccaagtagtgaaacagctgctcatgtaggacacggat
tattgacagtgctgccatttatcagccagtaatccacttggcaggt
agcacgctcatcgttatcctttatgcacacaaagccttgtttgaat
tttatcttttaatgagtgtcaatgaaatggaaagagataagagtta
aaaatacaacccaaactattgtatttacatttctcttttagaagaa
acctaaagcagcattacttcttgcccatatttaataaataacatca
tttacccttgttccctgcctccagactctcccatatactcctcttt
caattttattggcccctttaaatgacatatcattacatgtatatcc
ctacacataagtataaccagttcagtttgtataatgttacttgcat
gtgtgttttcaatgctgatcatttggtagtggataaccaatggtgt
gccctatgaaggggcagagtatttgtatcatgcttagcattccttt
gttgactgtaggattttgtttaaggttgaggtctcttggtctttcc
cctgtctgcttctgcatgtccatggccatccttgttcagctcatgt
ttatgtagtcatgctgatgaggctttatggatgtagcttctgacat
tgctaagcaacacagtctcagcaaactccccagtcctctggttctt
acaatctttccacactgtttcaccatgttgtctgagccttaggtgc
tgaagttgttttgtgtctgtatccattgggactaggctccacatgt
ctgcattttgattacttgtggttttctgtaacggtctctatgtgtt
gcaacgagaaggagtagttgctttgacgatgtgtaaagactatctt
gtgggtataaggacaaatatttgcatgaagctatggattatgctgg
tctcaagcatgaactggataaattgtacagctcacacaaaacagct
atagctagctgcacagtcaggcatgcactgatctgcttggggagtt
gttaaccaaagggcttacatagctatgtattttctaagctctagtt
ttactatcacaaagaaaattaattcacccttaattgtttaataaga
tgatatatcttagggaaaaaatgaaggtctttttttgacttatata
aaagcttatgttttctacagttt exon2 (SEQ ID NO 32):
tgtcaaaagaacatgcctcgcaagtcctggtgaggaagcgccgcgc
aaataccttgcttgaagaaactaaaaagggcaatcttgaaagagaa
tgcatcgaagagctctgcaataaagaggaagccagggaggtctttg
aaaacaatcccgaaacg intron2 (SEQ ID NO 33):
gtaagagttcgtggaaatgaccaagtccacactcggatatatattg
gcagtcagaacactgccagcttgagctaccttgcttctgtttgaaa
gctaatgacttaggagttcatttctcatgtgttaccactgacattt
caggcaggctgccaatgacaggcactccagccaaactccatttccc
ttaagtctcattactcgcaactagtatcgactttataatgtgtgac
tattttattatcctaaccaaatctggtagccttgagggtgcaagag
aagatgcgactgaagggtaagtgaccatatatgtacttgcattgtc
actgtgcttttgttttggttgattgtgtttgagacagtctcttact
ctgtagctccaactacaaggagctccctatccatctgctttggctt
cagcctcccaagtactgtgattatagactggtgtgtcttgccattt
atctttaagaggctctagatagaaatggggccacctaactgagatt
agtcattacagcattatgtatgctgactgtatactattctgtaacc
ttcatgaagtttcccgaggccactgataatcagcagtaatcattag
tgtctaaaaatttccaagttacccacccgccaaacataacataaag
acagcaacatgggactctttgtccattctgtgtttcaggagagggc
aatttatagtatgcttgtaactaacaggagtagcattaatatctcc
aaggagcactttgagcatgaccttgagagtctacatggaacactgt -continued

```
tcagggtctcctcagatgttctacctgagctgaattatacaatctg
gaggaaaagaaagagatgacatacacaaggctcctcctttgcctct
gccacagctcccagaaccatgacaacagctgagtgataaagagcaa
ggactctttgtccatacttagaaaatttgtccccaactgtagctac
ttgtggtctgtggttgttattgtagctctttttaatccctatgtg
ttctgataggttcaaagaagaaattttccccaaatatgcaacaatt
aaattttaatctacctagaattgagacaaaaatgtgacgaaatacc
ttgatcaaaaaaacaactcaggaggaaagggtttttttttttttt
ttggtttactaacctgaattgagggaagcaaaagtaggagctcaaa
ccaggtgggaacctggaggcaggagctgatgcagaggcatggagga
gtgctgcttactggtctgctcctcatggcttgctcagcttgttttc
ttatagaacccagggccaccgtcacaaaagtaccatcacctgcaat
gggttgggcccttccccagggatctctgattaagaaaattccctac
aggtctgtctacaattctttttgtttgtttgtttgtttgtttgtt
tgtttgttttcgagacagggtttgtctgtatagctttggagcctgt
cctggaactcactctgtagaccaggttggcctcgaagtcacaaaga
tccacctgcctttgcctccctagtgctgggattaaaggcttgtgtc
accactgccaggcctattttaaggaagcatttttctccttgagatt
ccttcctctcaaatgattctagcttgtatcaagttgacataaaatt
agccagcacagacaacaacaatagaaaatttctatcctacacaat
gtaataaatttattgggtaggatttaacatatgtattctatgtttt
acattctcattctaaaaggaatgtgtatgcactcttacaaacttc
cataatacaaaagaatacagtatgtattagatatgtgcatatattc
cttccctttatggaaagtttaaaaagtagaaagaatggtataataa
actgcaacacaacacgtccctctaataagatcaaggctttcatttg
attttgcctatccaccacatctaatcaatggttttgctttgagcaa
tcaagtcacatgattatattacccatacttgagttgtatatctgca
ttgtagatatgttctcaaagctcagcctttaaagagtagtagggag
ggaagatggaccacaggaagaaggggaggaaggtgaagaaggaaa
acacattcgtgtttctttaccttcactaatagttttgttgacagat
tccacctactccctgtccatatccctcatactcttaggccagtatt
cccagtgttattgaccctgatgtttacctgttcgcttgtcatcagc
atgtcaccaatctttaaatgccattgtttgtctccttattgtcttg
tctctgcttctgcagtaaacaacactgttgtctgaatgagtcagtg
tcaggcccctttcttataagccagtagaaacgtgcaagtttgtaca
tgataagaggaaagagtgtagattttgatgtagaaaaagccaagct
ccactctaagccagaattttgaatactttttatgcagaaattttgt
ttttgtatgaaatattcttgtgttatttatttacattatgagtgta
ctgtcagaagctcataaaaattaccctgttcataaaatacattcct
tcatccatatgtcatcattattttgctatccatcaatatataagga
aggtgtttcacatgcattagatgcaataaggtaagtggtcatttta
gttctctttaaatgatttcattgttgactccagtgtagatagtcat
catggcataagatgtatcaaatgaagactaggtgtggtggtgcata
ccttcagtcccagcacacagaggcagaggaacatggattgctgtga
gtttcaggtggacctggtctacatagtgagttccaaggtagataga
gggtgtctcgagagaccctgtaagaaaagtctatgtttaattgcca
tgaaaaaattagaggattataaaagagggaatatattgttatagtt
atcaactacaaccagttcaaatcagaagctttaaaatgttatttta
ttgttcagtagtgttttaagcatatatagtatacacacaaacatat
atgtgtttatatatatgtatatgtatactggtcaagtattggctat
ctattcttgaagtatttatagaaaaattagaaatgtgaaaacatac
aacatgtaggtcatttccatattcatataaaagcaaattagaaaaa
ttaatctttaactctgtagtgatatttgagtttgctaatatctatt
tttttattttctttctag

exon3 (SEQ ID NO 34):
gattatttttatccaaaatatttgg
```

Example 4

Transcription Factor Engineering

Expression of Protein S may be reduced or abolished by transcriptional down regulation of Protein S mRNA. Transcription factors can be designed to bind specific DNA elements in the promoter region of the CHO Protein S gene. Zinc finger proteins are ideal for such a manipulation and common procedures are reviewed by Wolfe-S A et al. Annu. Rev. Biophys. Struct. vol 3:183-212, 1999 and jamieson-A C et al. Nature Reviews, vol 2:361-368, 2003. Typically a single zinc finger binds three bases adjacent to each other on the same DNA strand and a forth base on the complementary strand. Thus, several zinc fingers can be combined in order to bind a desired DNA element. Recognition of a DNA element of 15-18 base pairs, which actually can be universal in the genome, needs a combination of 5-6 zinc fingers.

A DNA element having the sequence GGAGAGGAGGGGGGG (SEQ ID NO 35) from the CHO Protein S promoter are chosen and Zinc finger proteins binding the DNA element is predicted based on the publications by Liu-P Q et al., journal of Biological Chemistry, Vol. 276 (14), pp. 11323-11334, 2001 and Zhang-L et al, Journal of Biological Chemistry, Vol. 275 (43), pp. 33850-33860, 2000. A synthetic five zinc finger protein based on SP1 and BTEB4 is made by PCR from overlapping oligonucleotides as described in Zhang-L et al. Journal of Biological Chemistry, Vol. 275 (43), pp, 33850-33860, 2000: Zinc finger 5 CXXCXXXXXQSGHLQRHXXXH (SEQ ID NO 36) interacts with GGAg; zinc finger 4 CXXXXCXXXXXRSDNLARHXXXH (SEQ ID NO 37) interacts with GAGg; zinc finger 3 CXXCXXXXXRSDNLTRHXXXH (SEQ ID NO 38) interacts with GAGg; zinc finger 2 CXXXXCXXXXXRSDHLTRHXXXH (SEQ ID NO 39) interacts with GGGg; zinc finger 1 CXXXXCXXXXXRSDHLARHXXXH (SEQ ID NO 40) interacts with GGGa; and N-terminal to the zinc fingers the KRAB domain of KOX1 is inserted.

Upon binding of the engineered zinc finger protein to the GGAGAGGAGGGGGGG (SEQ ID NO 41) DNA element the CHO Protein S transcription was expected to be down-regulated.

The CHO Protein S promoter region (SEQ ID NO 29) was cloned into pGL3-basic (Promega, Madison) and was used as reporter construct in a luciferase reporter assay to determine the effect of ZNF-PS. The plasmid encoding the ZNF-PS gene and the CHO Protein S reporter plasmid were transfected into CHO K1 cells and luciferase activity was determined. ZNF-PS can downregulate Protein S transcription 50% in a dose-response independent manner. FIG. 3*a* illustrates ZNF-PS downregulation of Protein S. In a similar experiment the CHO K1 cells were transfected with ZNF-PS and pEGFP (Enhanced Green Flourescent Protein) and Protein Sand pEGFP mRNA were determined by real-time PCR. pEGFP served as transfection control. FIG. 3*b* shows a down-regulation of Protein S by 50%.

```
ZNF-PS
                                        (SEQ ID NO 42)
Mdaksltawsrtlvtfkdvfvdftreewklldtaqqivyrnvmlen

yknlvslgyqltkpdvilrlekgeepwlvereihqethpdsetafe

ikssvssrsifkdkqscdikmegmarndlwylsleevwkpgkkkqh

ichiqgcgkvygrsdhlarhlrwhtgerpfmctwsycgkrftrsdh

ltrhkrthgekkfacpecpkrfmrsdnltrhikthtgerpfacdwq

gcdkkfarsdnlarhhrthtgekrfscplcskrftqsghlqrharr

hpgfhpdllrrpgarstspsdslpcslagspapspapspapagl
```

Example 5

Determination of numbers of Protein S Alleles in the CHO K1 Genome

The CHO-K1 cell line has only 21 chromosomes, compared to the Chinese Hamster which has 2.2 chromosomes, and only 8 of these 2.1 are normal. In the 13 altered chromosomes translocations, deletions, and pericentric inversions have been detected (Deaven & Petersen, Chromosoma 1973; 41(2), 129-144). It is not known whether the Protein S gene is present on normal or altered chromosomes or how many alleles are present in the CHO-K1 genome.

The SeeDNA Biotech Inc. company performed a FISH (Flourescence In Situ Hybridization) analysis on the genome of CHO K1 cells (ATCC#CCL-61) using a plasmid containing the Protein S Intron 1 probe (SEQ ID NO 43) in pCR2.1 (Invitrogen, Carlsbad) cloned and supplied by us. The results of the FISH analysis is shown i FIG. 4, The Protein S gene is localized onto two different chromosomes in the same metaphase. The chromosome with locus A (shown by an arrow) is submetacentric and of smaller size. The chromosome with locus B (shown by an arrowhead) is metacentric and of bigger size. The banding pattern of these two chromosomes is also different.

```
The Protein S Intron 1 probe
                                              (SEQ ID NO 43)
ctgctggtatgcctagccctggtgctgccagcctcggagacaaact

gtaagtaatccatacctcctggcttctccattccctatgtgccccg

gcttgaagattttccactaggctgtttgctgcctcctaagtttcca

gtaagtccgccaccattcagagagtcgcggcagcctgggtctggtg

ggcagtgtaaaggtgggacaggatcaaagcttgccttgctttgaga

accattgtccacaggacttgattccagaacccgggtgacactaagt

gtcaaaggaattgcttgaacatagtcctaaatattgctaggaaagc

taagtcaagcctgttgccctcctcccgtttacaagagtgccccagc

ccgcaccctctcctgcggctaaccttccttttgcaatttctggact

ttgaacttgattgactggtctcacattgacaaactgtttggggact

gctggggtgttacatatgattctctaaccttgatataagaaatagc

tgttggatgttaccttgtaccgaggatcattttctgagggttttga

ctgttgccgctttgagatggcagcaagaattctgtacaacacacac

atttttgtgtttcttggtctttcctcttcccattctcagattccgg

gcagtatatcgagttttctcttagaaatataaaacgaaccacaagg

ttttagtacattttaatggtcaattaaattgtttttagaagcttaa

atatgttcataattaacactgctttcttttgctcttttgtagtccc

agtcactggcatgggagcaataactgtataacaaataccacttagg

tcactgcgagcaccaaagaaacttttcaaagatggtaattaagtag

gagtttgctggaattgcaagtttttattaattagtaaggaatctag

cctgatatttttaaatgtctaactaagttaaagaccagaatgaaac

tggttcactttttattgaggataaacaagttacagttataaagcct

caacaatcaaagccctacgatgaagcagcgtgtgactgtatgcaca

tgatctatcttgttcagaggaacaatcaaacattttcagatagcat

cagggcggtggtggtactcgcctataatcctagcaaagtcagaggc

aagcagatctctgtgttcaaggccagcctagtctacagagtgagtt

ccaggacaactggggctacacagagaaacctgtctcagagaaaaac

aaaataaaaccaaattcagatagctggtgtttgggaaaagagcaaa

agacagcagtgctggccacacagagagtagacaagttcattctaca

aggacatcacagaaagaatatgtgacccaatgacgaccataaactt

tcttgttcctgtgtcaaattatctccggtttattgatgaagaacca

gacactatgagctgcgtctcctccttaagattttgttttggtgtct
```

-continued

```
tgtttttgtcaaggggtttcattgtggccctgagcattagatccag

ggcttttgtgcatgctaggccagggagctatattcccgaactccag

aagactaggaatttgagatataaatagaatttgaattaccttctgt

acaattgattgtatggttctagaaatattgctatattaagggaagc

ctttgcagaagacagttattttgagatggtgcataacacaaaagaa

atgaactaaagcctgaggcctgctctgtagctctgccttgccctta

gcctacaataactttctttacctttcaagcatgtgccaccacgcct

gactttcaggcccttcattttaacaagaaagcaagtattcagttat

caactgactttccaaatgcatttgtatgaataaaaactacaaaaat

ataaaaataagaactatacacacaaaagccttgtatttaaaattta

cgctgtggacatattttgctcatcattcgtgagagcttgcggtaaa

aaggcaaaggggaagaggaggatatctattttgggtaggctaattt

ggccttatccagacttcccttttgggtggatgcagtctgcccagca

cactattggcccatttcttctacatggctttgtgctctgctctgcc

cttagctaattgtcccctttgacatgcttttgtctttccttaaagt

ttctatacttcaaaaaccatcccgctacactaatggagtgattttc

tcaagggttgctttatgtttggggtttgtactgcaagagttagttt

ctgatatagcaatggtgatagtatagtcttctaccatgaactctat

gccagcaagtacaggggtatatttcacatgggtgttttctgttcac

tgagtttcatgtcttctttgtatctttttgttttgttttgtgagac

agggtttctctgtagcttttgagtcagtcctggaacttgctggccg

gccttgaactcacagagattcacctgcctctgcctcccaagtgctg

ggatttaaggtgtgagtcaccactgccaggtttttctttgtatct

tgagtgaactaaataggtaagctttaaataataatatgagcagtct

atttatatacattaaatattaaatgcattgtgagatgagcatagcc

tttgaggcccaggaacagaaagatttacttcacattgtaaatatac

tggtatacatacaaacgtacatacnnnnnngtgtgtgtgtgtgtgt

gtgtgtgtgtgtgcatgccatagcacacatgtgaagtccagagtac

agcattctctttttctacctttctgtagattcttgtggtcagagtc

aggtcaaatcaaatcagacagatgcatgtataaaatgctcttaccc

actgaaccatcttgctgcttggtccacaagcttagtggaagaatgc

tgggaagtgaatagtatgtttttaaatgtagttaaccttgactttt

tgttgttgttgctgttattgaggccacattttcattgttctgagaa

aatattactattttcctcagacagaattatatatttatttgaagtt

catgaattccatattattttcctgtatttattacaaatagcatgct

taaacacttccaagtagtgaaacagctgctcatgtaggacacggat

tattgacagtgctgccatttatcagccagtaatccacttggcaggt

agcacgctcatcgttatcctttatgcacacaaagccttgtttgaat

tttatcttttaatgagtgtcaatgaaatggaaagagataagagtta

aaaatacaacccaaactattgtatttacatttctcttttagaagaa
```

-continued

```
acctaaagcagcattacttcttgcccatatttaataaataacatca

tttacccttgttccctgcctccagactctcccatatactcctcttt

caattttattggcccctttaaatgacatatcattacatgtatatcc

ctacacataagtataaccagttcagtttgtataatgttacttgcat

gtgtgttttcaatgctgatcatttggtagtggataaccaatggtgt

gccctatgaaggggcagagtatttgtatcatgcttagcattccttt

gttgactgtaggattttgtttaaggttgaggtctcttggtctttcc

cctgtctgcttctgcatgtccatggccatccttgttcagctcatgt

ttatgtagtcatgctgatgaggctttatggatgtagcttctgacat

tgctaagcaacacagtctcagcaaactccccagtcctctggttctt

acaatctttccacactgtttcaccatgttgtctgagccttaggtgc

tgaagttgttttgtgtctgtatccattgggactaggctccacatgt

ctgcattttgattacttgtggttttctgtaacggtctctatgtgtt

gcaacgagaaggagtagttgctttgacgatgtgtaaagactatctt

gtgggtataaggacaaatatttgcatgaagctatggattatgctgg

tctcaagcatgaactggataaattgtacagctcacacaaaacagct

atagctagctgcacagtcaggcatgcactgatctgcttggggagtt

gttaaccaaagggcttacatagctatgtattttctaagctctagtt

ttactatcacaaagaaaattaattcacccttaattgtttaataaga

tgatatatcttagggaaaaaatgaaggtctttttttgacttatata

aaagcttatgttttctacagttttgtcaaaagaacatgcctcgcaa

gtcctggtgaggaagcgccgcgcaaataccttgcttgaagaaacta

aaaagggcaatcttgaaagagaatgcatcgaagagctctgc
```

Example 6

Gene Targeting of CHO Protein S Enhanced by Zinc Finger-Nuclease Fusion Proteins Gene targeting by homologous recombination is hard and laborious work because the somatic recombinations that takes place in mammalian cells not very often are homologous. However, site-specific cleavage of the DNA strands can enhance homologous recombination. Engineering of DNA binding zinc fingers fused to endonucleases makes it possible to design almost exactly where the DNA cleavage should occur (Durai et al., Nucleic Acids Research, 2005; 33(18), 5970-5990 and Smith et al., Nucleic Acids Research, 2000; 28(17), 3361-3369). Two zinc finger proteins, designed to bind 5'-GTCCTGAGC-3' (right finger) and 5'-GCTGG-TATG-3' (left finger) elements, were made in the framework published by Mani et al. (Mani et al., Biochemical and Biophysical Research Communications 2005, 335; 447-457). Zinc finger DNA binding specificity of zinc finger has previously been described by (Rebar-E J, et al. Nature Medicine 8 (2002) 1427-1432; Liu-P Q, et al. Journal of Biological Chemistry 276 (2001) 11323-11334; Ren-D, et al. Genes & Development 16 (2002) 27-32; Mani-M, et al Biochemical and Biophysical Research Communications 335 (2005) 447-457).

The right and left zinc finger were both either fused to the nuclease domain of Fok I and Sts I restriction enzyme (SEQ ID NO 44-51). Fok I and Sts I restriction enzyme needs to homodimerize to be able to cleave DNA, which also increase the specificity of the zinc finger pair. The function of the engineered nucleases are illustrated in FIGS. 5 and 6. When the genomic DNA has been cleaved by the zinc finger nucleases the repair mechanism will seek to repair the gap, very likely by homologous recombination. The gene targeting construct (SEQ ID NO 52) devoid of the Protein S gene will be transfected along with the nucleases. In the place of Protein S exon 1 in the genome the EGFP gene will be inserted. FIG. 6 illustrates the flow scheme of the homologous recombination. The gene targeting construct was made by exchanging the luciferase gene in the Protein S reporter construct (example 4) by the EGFP-gene and further inserting Protein S intron 1 after the poly A signal. The construct consists of Protein S promoter, EGFP-gene, PolyA-signal and Protein S intron1, no exon1. The homozygous recombinant CHO cell line will express EGFP and not Protein S because the Protein S signal peptide has been deleted and the transcript will be truncated right after the EGFP coding sequence due to the PolyA signal. Heterozygous cell clones are expected to be most abundant and a PCR analysis will reveal whether we have succeeded to make a homozygous cell clone. A heterozygous cell clone can be treated a second time with a targeting vector containing an antibiotical resistance gene in place of the EGFP gene to facilitate selection. (SEQ ID NO 44) Left zinc finger-Fok I DNA sequence

The invention claimed is:

1. A method for producing a composition comprising a Vitamin K-dependent protein of interest having a substantially lower amount of protein contaminant Protein S expressed endogenously by a Chinese Ovary Hamster (CHO) host cell in the absence of modification, said method comprising the steps of:

a) producing said host cell expressing a Vitamin K-dependent protein of interest comprising the following steps in any order:

1) transfecting a cell with a polynucleotide construct encoding a Vitamin K-dependent protein of interest; and 2) modifying said cell to express a substantially lower amount of endogenous Protein S by any method selected from:

i) disruption by gene knock-out of the gene encoding endogenous Protein S;

ii) transfection with a siRNA polynucleotide construct targeting a mRNA encoding Protein S;

iii) transfection with a transcription factor being a Zinc finger protein binding to a DNA element of the gene encoding endogenous Protein S;

iv) random mutagenesis for disruption of the gene encoding endogenous Protein S; and b) growing said host cell in a growth medium and harvesting said growth medium comprising said Vitamin K-dependent protein of interest;

wherein said Vitamin K-dependent protein of interest is selected from the group consisting of: Protein S, GAS-6, Factor II (Prothrombin), Factor X, Factor IX, Protein C, Factor VII, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Bone Gla protein, Matrix Gla protein, and Osteocalcin.

* * * * *

SEQUENCE LISTING

```
<160> NUMBER OF SEQ ID NOS: 52

<210> SEQ ID NO 1
<211> LENGTH: 23
<212> TYPE: DNA
<213> ORGANISM: Artificial
<220> FEATURE:
<223> OTHER INFORMATION: Synthetic DNA primer

<400> SEQUENCE: 1

gcccaggctc gcagctcctc tgg                                              23


<210> SEQ ID NO 2
<211> LENGTH: 23
<212> TYPE: DNA
<213> ORGANISM: Artificial
<220> FEATURE:
```

```
<223> OTHER INFORMATION: Synthetic DNA primer

<400> SEQUENCE: 2

caggtgacac ctgccagctg gtg                                              23


<210> SEQ ID NO 3
<211> LENGTH: 2306
<212> TYPE: DNA
<213> ORGANISM: Artificial
<220> FEATURE:
<223> OTHER INFORMATION: CHO Protein S cDNA sequence

<400> SEQUENCE: 3

gcccaggctc gcagctcctc tgggcggagc gccggctcgg tccccgctgc gccagccgtg      60

atccccggca gcctgctcag caatgagggt cctgagcgcg cgctgtcggc tactgctggt     120

atgcctagcc ctggtgctgc cagcctcgga gacaaacttt ttgtcaaaag aacatgcctc     180

gcaagtcctg gtgaggaagc gccgcgcaaa taccttgctt gaagaaacta aaaagggcaa     240

tcttgaaaga gaatgcatcg aagagctctg caataaagag gaagccaggg aggtctttga     300

aaacaatccc gaaacggatt atttttatcc aaaatatttg ggttgtctgg gcatgttccg     360

tgctggcctg ttcagtgctg cgcggcagtc tgttaatgct taccccgacc tcaggagctg     420

tgtcaatgcc atcccagacc aatgtgatcc tatgccatgc aatgaagatg ggtatctgag     480

ctgcaaagat ggccaagctg ctttcacatg catctgcaaa ccaggatggc aaggggacaa     540

atgccagttt gatgtaaatg aatgtaaaga tcccttaaat gtaaatgggg gctgcagcca     600

gatttgtgac aacactcctg gaagttacca ctgctcctgc agaagtggct ttgctatgct     660

ttcaaacaaa aaagactgca aagatgtgga tgaatgctct atgaagccca gtgtttgtgg     720

ctcagctgtg tgcaagaaca ctccaggaga ctatgagtgt gaatgtcctg acggctacag     780

atatgatccc tcatcgaagt cttgcaaaga tgtggacgaa tgctctgaga acatgtgtgc     840

tcaattgtgt gtcaattacc ctggaggcta ctcttgttac tgtgatggaa agaaaggatt     900

caagcttgcc caagatcaga agagttgtga gggtattcca gtgtgccttc ccttgaacct     960

tgacaaaaat tatgaattat tgtacttggc tgagcagttt gtaggagttg tcttatatct    1020

gaaatttcgt ttgccagaaa ttaccagatt ttcagctgaa tttgattttc ggacatatga    1080

ttcagagggc atcatcctgt atgcagaatc tcttgatcac tcaaattggc tcctgattgc    1140

acttcgtgat ggaaaaattg aagttcagtt taagaatgag ttttcaaccc aaatcacaac    1200

cggaggcaat gttattaaca atggtaaatg gaacatggta tccgtggaag aattagacga    1260

cagtgttagc attaaaatag ctaaagaagc tgtgatgaat ataaataaat ttgggagcct    1320

ctttaaacct acagatggat ttctggacac caaaatatac tttgcaggat tacctcgggt    1380

agtggaaagt gcactcatta aaccgattaa ccctcgtctg gatggatgta tacgaggctg    1440

gaacttgatg aaacaaggag ctttaggtgc aaaggaaatt attcaaggaa aacaaaataa    1500

gcattgcttc ctcatggtgg agaagggctc ctactaccct ggttctggaa ttgctcggtt    1560

cagcatagat tacaataatg taaccaatgc agagggctgg caaataaatg tgaccttgaa    1620

tattcgtcca tccactggca ctggaattat gcttgccttg gtttctggag acaaagtgcc    1680

ctttgccttg tccttggtgg gctccagctc tgaaaattct caggatattg tggtatttgt    1740

tgaaaattca gtggtggctc gaatggaggc cataactctg tgttctgacc agcaatccca    1800

actgaaatgt aatgttaaca gacatggcct agagctatgg agcccactga agaaagatgt    1860

catctactct aaagatattc aaggacaact agcagtcttg gacaaagcaa tgaaaggaaa    1920
```

```
cgtggccact tatctgggtg gcattccaga tctttccttc agtgccacgc cagtgaatgc   1980

cttctacagt ggctgcatgg aagtgaacat caacggggtg cagttggatc tggatgaagc   2040

catttctaaa cataatgaca tcagagctca ctcatgtcct tcagttaaga aaatccagaa   2100

gaacgtctaa tgtctgtttt ctgtgcttat aatgcccctt tccttgtaat tatgctcacg   2160

cccctatcac cagctggcag gtgtcacctg tgaagtgcaa tgtttgaaat gatgtggtac   2220

tttgtccttc agatttttgt tatataaacc acgttttttt ttttttttta aagtctttct   2280

tctattgctg tctagaaatt aaataa                                        2306
```

<210> SEQ ID NO 4
<211> LENGTH: 2028
<212> TYPE: DNA
<213> ORGANISM: Artificial
<220> FEATURE:
<223> OTHER INFORMATION: CHO Protein S coding sequence

<400> SEQUENCE: 4

```
atgagggtcc tgagcgcgcg ctgtcggcta ctgctggtat gcctagccct ggtgctgcca     60

gcctcggaga caaacttttt gtcaaaagaa catgcctcgc aagtcctggt gaggaagcgc    120

cgcgcaaata ccttgcttga agaaactaaa aagggcaatc ttgaaagaga atgcatcgaa    180

gagctctgca ataaagagga agccagggag gtctttgaaa acaatcccga aacggattat    240

ttttatccaa aatatttggg ttgtctgggc atgttccgtg ctggcctgtt cagtgctgcg    300

cggcagtctg ttaatgctta ccccgacctc aggagctgtg tcaatgccat cccagaccaa    360

tgtgatccta tgccatgcaa tgaagatggg tatctgagct gcaaagatgg ccaagctgct    420

ttcacatgca tctgcaaacc aggatggcaa ggggacaaat gccagtttga tgtaaatgaa    480

tgtaaagatc ccttaaatgt aaatgggggc tgcagccaga tttgtgacaa cactcctgga    540

agttaccact gctcctgcag aagtggcttt gctatgcttt caaacaaaaa agactgcaaa    600

gatgtggatg aatgctctat gaagcccagt gtttgtggct cagctgtgtg caagaacact    660

ccaggagact atgagtgtga atgtcctgac ggctacagat atgatccctc atcgaagtct    720

tgcaaagatg tggacgaatg ctctgagaac atgtgtgctc aattgtgtgt caattaccct    780

ggaggctact cttgttactg tgatggaaag aaaggattca agcttgccca agatcagaag    840

agttgtgagg gtattccagt gtgccttccc ttgaaccttg acaaaaatta tgaattattg    900

tacttggctg agcagtttgt aggagttgtc ttatatctga aatttcgttt gccagaaatt    960

accagatttt cagctgaatt tgattttcgg acatatgatt cagagggcat catcctgtat   1020

gcagaatctc ttgatcactc aaattggctc ctgattgcac ttcgtgatgg aaaaattgaa   1080

gttcagttta agaatgagtt ttcaacccaa atcacaaccg gaggcaatgt tattaacaat   1140

ggtaaatgga acatggtatc cgtggaagaa ttagacgaca gtgttagcat taaaatagct   1200

aaagaagctg tgatgaatat aaataaattt gggagcctct ttaaacctac agatggattt   1260

ctggacacca aaatatactt tgcaggatta cctcgggtag tggaaagtgc actcattaaa   1320

ccgattaacc ctcgtctgga tggatgtata cgaggctgga acttgatgaa acaaggagct   1380

ttaggtgcaa aggaaattat tcaaggaaaa caaaataagc attgcttcct catggtggag   1440

aagggctcct actaccctgg ttctggaatt gctcggttca gcatagatta caataatgta   1500

accaatgcag agggctggca aataaatgtg accttgaata ttcgtccatc cactggcact   1560

ggaattatgc ttgccttggt ttctggagac aaagtgccct ttgccttgtc cttggtgggc   1620
```

```
tccagctctg aaaattctca ggatattgtg gtatttgttg aaaattcagt ggtggctcga   1680

atggaggcca taactctgtg ttctgaccag caatcccaac tgaaatgtaa tgttaacaga   1740

catggcctag agctatggag cccactgaag aaagatgtca tctactctaa agatattcaa   1800

ggacaactag cagtcttgga caaagcaatg aaaggaaacg tggccactta tctgggtggc   1860

attccagatc tttccttcag tgccacgcca gtgaatgcct tctacagtgg ctgcatggaa   1920

gtgaacatca acggggtgca gttggatctg gatgaagcca tttctaaaca taatgacatc   1980

agagctcact catgtccttc agttaagaaa atccagaaga acgtctaa                2028
```

<210> SEQ ID NO 5
<211> LENGTH: 675
<212> TYPE: PRT
<213> ORGANISM: Artificial
<220> FEATURE:
<223> OTHER INFORMATION: CHO Protein S amino acid sequence

<400> SEQUENCE: 5

```
Met Arg Val Leu Ser Ala Arg Cys Arg Leu Leu Leu Val Cys Leu Ala
1               5                   10                  15

Leu Val Leu Pro Ala Ser Glu Thr Asn Phe Leu Ser Lys Glu His Ala
            20                  25                  30

Ser Gln Val Leu Val Arg Lys Arg Arg Ala Asn Thr Leu Leu Glu Glu
        35                  40                  45

Thr Lys Lys Gly Asn Leu Glu Arg Glu Cys Ile Glu Glu Leu Cys Asn
    50                  55                  60

Lys Glu Glu Ala Arg Glu Val Phe Glu Asn Asn Pro Glu Thr Asp Tyr
65                  70                  75                  80

Phe Tyr Pro Lys Tyr Leu Gly Cys Leu Gly Met Phe Arg Ala Gly Leu
                85                  90                  95

Phe Ser Ala Ala Arg Gln Ser Val Asn Ala Tyr Pro Asp Leu Arg Ser
            100                 105                 110

Cys Val Asn Ala Ile Pro Asp Gln Cys Asp Pro Met Pro Cys Asn Glu
        115                 120                 125

Asp Gly Tyr Leu Ser Cys Lys Asp Gly Gln Ala Ala Phe Thr Cys Ile
    130                 135                 140

Cys Lys Pro Gly Trp Gln Gly Asp Lys Cys Gln Phe Asp Val Asn Glu
145                 150                 155                 160

Cys Lys Asp Pro Leu Asn Val Asn Gly Gly Cys Ser Gln Ile Cys Asp
                165                 170                 175

Asn Thr Pro Gly Ser Tyr His Cys Ser Cys Arg Ser Gly Phe Ala Met
            180                 185                 190

Leu Ser Asn Lys Lys Asp Cys Lys Asp Val Asp Glu Cys Ser Met Lys
        195                 200                 205

Pro Ser Val Cys Gly Ser Ala Val Cys Lys Asn Thr Pro Gly Asp Tyr
    210                 215                 220

Glu Cys Glu Cys Pro Asp Gly Tyr Arg Tyr Asp Pro Ser Ser Lys Ser
225                 230                 235                 240

Cys Lys Asp Val Asp Glu Cys Ser Glu Asn Met Cys Ala Gln Leu Cys
                245                 250                 255

Val Asn Tyr Pro Gly Gly Tyr Ser Cys Tyr Cys Asp Gly Lys Lys Gly
            260                 265                 270

Phe Lys Leu Ala Gln Asp Gln Lys Ser Cys Glu Gly Ile Pro Val Cys
        275                 280                 285
```

```
Leu Pro Leu Asn Leu Asp Lys Asn Tyr Glu Leu Leu Tyr Leu Ala Glu
    290                 295                 300

Gln Phe Val Gly Val Val Leu Tyr Leu Lys Phe Arg Leu Pro Glu Ile
305                 310                 315                 320

Thr Arg Phe Ser Ala Glu Phe Asp Phe Arg Thr Tyr Asp Ser Glu Gly
                325                 330                 335

Ile Ile Leu Tyr Ala Glu Ser Leu Asp His Ser Asn Trp Leu Leu Ile
            340                 345                 350

Ala Leu Arg Asp Gly Lys Ile Glu Val Gln Phe Lys Asn Glu Phe Ser
        355                 360                 365

Thr Gln Ile Thr Thr Gly Gly Asn Val Ile Asn Asn Gly Lys Trp Asn
    370                 375                 380

Met Val Ser Val Glu Glu Leu Asp Asp Ser Val Ser Ile Lys Ile Ala
385                 390                 395                 400

Lys Glu Ala Val Met Asn Ile Asn Lys Phe Gly Ser Leu Phe Lys Pro
                405                 410                 415

Thr Asp Gly Phe Leu Asp Thr Lys Ile Tyr Phe Ala Gly Leu Pro Arg
            420                 425                 430

Val Val Glu Ser Ala Leu Ile Lys Pro Ile Asn Pro Arg Leu Asp Gly
        435                 440                 445

Cys Ile Arg Gly Trp Asn Leu Met Lys Gln Gly Ala Leu Gly Ala Lys
    450                 455                 460

Glu Ile Ile Gln Gly Lys Gln Asn Lys His Cys Phe Leu Met Val Glu
465                 470                 475                 480

Lys Gly Ser Tyr Tyr Pro Gly Ser Gly Ile Ala Arg Phe Ser Ile Asp
                485                 490                 495

Tyr Asn Asn Val Thr Asn Ala Glu Gly Trp Gln Ile Asn Val Thr Leu
            500                 505                 510

Asn Ile Arg Pro Ser Thr Gly Thr Gly Ile Met Leu Ala Leu Val Ser
        515                 520                 525

Gly Asp Lys Val Pro Phe Ala Leu Ser Leu Val Gly Ser Ser Ser Glu
    530                 535                 540

Asn Ser Gln Asp Ile Val Val Phe Val Glu Asn Ser Val Val Ala Arg
545                 550                 555                 560

Met Glu Ala Ile Thr Leu Cys Ser Asp Gln Gln Ser Gln Leu Lys Cys
                565                 570                 575

Asn Val Asn Arg His Gly Leu Glu Leu Trp Ser Pro Leu Lys Lys Asp
            580                 585                 590

Val Ile Tyr Ser Lys Asp Ile Gln Gly Gln Leu Ala Val Leu Asp Lys
        595                 600                 605

Ala Met Lys Gly Asn Val Ala Thr Tyr Leu Gly Gly Ile Pro Asp Leu
    610                 615                 620

Ser Phe Ser Ala Thr Pro Val Asn Ala Phe Tyr Ser Gly Cys Met Glu
625                 630                 635                 640

Val Asn Ile Asn Gly Val Gln Leu Asp Leu Asp Glu Ala Ile Ser Lys
                645                 650                 655

His Asn Asp Ile Arg Ala His Ser Cys Pro Ser Val Lys Lys Ile Gln
            660                 665                 670

Lys Asn Val
        675
```

<210> SEQ ID NO 6
<211> LENGTH: 21
<212> TYPE: DNA

```
<213> ORGANISM: Artificial
<220> FEATURE:
<223> OTHER INFORMATION: SiRNA target sequence
<220> FEATURE:
<221> NAME/KEY: misc_feature
<222> LOCATION: (3)..(19)
<223> OTHER INFORMATION: n is a, c, g, or t

<400> SEQUENCE: 6

agnnnnnnnn nnnnnnnnnc t                                                21


<210> SEQ ID NO 7
<211> LENGTH: 21
<212> TYPE: DNA
<213> ORGANISM: Artificial
<220> FEATURE:
<223> OTHER INFORMATION: Synthetic DNA sequence

<400> SEQUENCE: 7

agtgtgaatg tcctgacggc t                                                21


<210> SEQ ID NO 8
<211> LENGTH: 37
<212> TYPE: DNA
<213> ORGANISM: Artificial
<220> FEATURE:
<223> OTHER INFORMATION: Synthetic DNA sequence

<400> SEQUENCE: 8

gatctaaaaa agtgtgaatg tcctgacggc tttttta                               37


<210> SEQ ID NO 9
<211> LENGTH: 37
<212> TYPE: DNA
<213> ORGANISM: Artificial
<220> FEATURE:
<223> OTHER INFORMATION: Synthetic DNA sequence

<400> SEQUENCE: 9

gatctaaaaa agccgtcagg acattcacac tttttta                               37


<210> SEQ ID NO 10
<211> LENGTH: 21
<212> TYPE: DNA
<213> ORGANISM: Artificial
<220> FEATURE:
<223> OTHER INFORMATION: Synthetic DNA sequence

<400> SEQUENCE: 10

agctgcaaag atggccaagc t                                                21


<210> SEQ ID NO 11
<211> LENGTH: 37
<212> TYPE: DNA
<213> ORGANISM: Artificial
<220> FEATURE:
<223> OTHER INFORMATION: Synthetic DNA sequence

<400> SEQUENCE: 11

gatctaaaaa agctgcaaag atggccaagc tttttta                               37


<210> SEQ ID NO 12
<211> LENGTH: 37
<212> TYPE: DNA
<213> ORGANISM: Artificial
<220> FEATURE:
<223> OTHER INFORMATION: Synthetic DNA sequence
```

<400> SEQUENCE: 12
gatctaaaaa agcttggcca tctttgcagc ttttta 37

<210> SEQ ID NO 13
<211> LENGTH: 21
<212> TYPE: DNA
<213> ORGANISM: Artificial
<220> FEATURE:
<223> OTHER INFORMATION: Synthetic DNA sequence

<400> SEQUENCE: 13
agaacatgcc tcgcaagtcc t 21

<210> SEQ ID NO 14
<211> LENGTH: 37
<212> TYPE: DNA
<213> ORGANISM: Artificial
<220> FEATURE:
<223> OTHER INFORMATION: Synthetic DNA sequece

<400> SEQUENCE: 14
gatctaaaaa agaacatgcc tcgcaagtcc ttttta 37

<210> SEQ ID NO 15
<211> LENGTH: 37
<212> TYPE: DNA
<213> ORGANISM: Artificial
<220> FEATURE:
<223> OTHER INFORMATION: Synthetic DNA sequence

<400> SEQUENCE: 15
gatctaaaaa aggacttgcg aggcatgttc ttttta 37

<210> SEQ ID NO 16
<211> LENGTH: 21
<212> TYPE: DNA
<213> ORGANISM: Artificial
<220> FEATURE:
<223> OTHER INFORMATION: Synthetic DNA sequence

<400> SEQUENCE: 16
agaaactaaa aagggcaatc t 21

<210> SEQ ID NO 17
<211> LENGTH: 37
<212> TYPE: DNA
<213> ORGANISM: Artificial
<220> FEATURE:
<223> OTHER INFORMATION: Synthetic DNA sequence

<400> SEQUENCE: 17
gatctaaaaa agaaactaaa aagggcaatc ttttta 37

<210> SEQ ID NO 18
<211> LENGTH: 37
<212> TYPE: DNA
<213> ORGANISM: Artificial
<220> FEATURE:
<223> OTHER INFORMATION: Synthetic DNA sequence

<400> SEQUENCE: 18
gatctaaaaa agattgccct ttttagtttc ttttta 37

<210> SEQ ID NO 19

```
<211> LENGTH: 21
<212> TYPE: DNA
<213> ORGANISM: Artificial
<220> FEATURE:
<223> OTHER INFORMATION: Synthetic DNA sequence

<400> SEQUENCE: 19

agccagattt gtgacaacac t                                                21


<210> SEQ ID NO 20
<211> LENGTH: 37
<212> TYPE: DNA
<213> ORGANISM: Artificial
<220> FEATURE:
<223> OTHER INFORMATION: Synthetic DNA sequence

<400> SEQUENCE: 20

gatctaaaaa agccagattt gtgacaacac tttttta                               37


<210> SEQ ID NO 21
<211> LENGTH: 37
<212> TYPE: DNA
<213> ORGANISM: Artificial
<220> FEATURE:
<223> OTHER INFORMATION: Synthetic DNA sequence

<400> SEQUENCE: 21

gatctaaaaa agtgttgtca caaatctggc tttttta                               37


<210> SEQ ID NO 22
<211> LENGTH: 25
<212> TYPE: PRT
<213> ORGANISM: Artificial
<220> FEATURE:
<223> OTHER INFORMATION: Artificial construct

<400> SEQUENCE: 22

Met Arg Val Leu Ser Val Arg Cys Arg Leu Leu Leu Val Cys Leu Ala
1               5                   10                  15

Leu Val Leu Pro Ala Ser Glu Thr Asn
            20                  25


<210> SEQ ID NO 23
<211> LENGTH: 24
<212> TYPE: DNA
<213> ORGANISM: Artificial
<220> FEATURE:
<223> OTHER INFORMATION: Synthetic DNA primer

<400> SEQUENCE: 23

ctgctggtat gcctagccct ggtg                                             24


<210> SEQ ID NO 24
<211> LENGTH: 24
<212> TYPE: DNA
<213> ORGANISM: Artificial
<220> FEATURE:
<223> OTHER INFORMATION: DNA primer

<400> SEQUENCE: 24

tgcagagctc ttcgatgcat tctc                                             24


<210> SEQ ID NO 25
<211> LENGTH: 24
<212> TYPE: DNA
<213> ORGANISM: Artificial
```

<220> FEATURE:
<223> OTHER INFORMATION: DNA primer

<400> SEQUENCE: 25
aagggcaatc ttgaaagaga atgc 24

<210> SEQ ID NO 26
<211> LENGTH: 25
<212> TYPE: DNA
<213> ORGANISM: Artificial
<220> FEATURE:
<223> OTHER INFORMATION: DNA primer

<400> SEQUENCE: 26
ccaaatattt tggataaaaa taatc 25

<210> SEQ ID NO 27
<211> LENGTH: 20
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (1)..(20)
<223> OTHER INFORMATION: n in position 3 is Adenosine or Guanosine

<400> SEQUENCE: 27
aancaacccc ttttgaccat 20

<210> SEQ ID NO 28
<211> LENGTH: 21
<212> TYPE: DNA
<213> ORGANISM: Artificial
<220> FEATURE:
<223> OTHER INFORMATION: DNA primer

<400> SEQUENCE: 28
cccagaggag ctgcgagcct g 21

<210> SEQ ID NO 29
<211> LENGTH: 1631
<212> TYPE: DNA
<213> ORGANISM: Artificial
<220> FEATURE:
<223> OTHER INFORMATION: immediately 5' to coding sequence

<400> SEQUENCE: 29
aarcaacccc ttttgaccat acacatttct actctttgtg tttgctggag ctgttttctc 60
cccacactca acccccttg ctgaagcctg gaacttgctt tccacagctt aagttgttat 120
aggtttcaat catctgtcca cctccctgac tttcataatt ttgtgaaata cccttgcata 180
tatatatggg actaaatatt attttctcct ggttgtccat aatagattaa tttaattcct 240
aaacaaagaa cagaacatag attggtatag tagaagagtt tcccttctcc ctactgcatg 300
aatggaaatt ccccaaacca tccttatcag agaaattaac tcacatacta gtcacctttc 360
attcagctgg atgacaaaat cattttaaaa aaagagaata aagaaaacag ataagaacaa 420
ctagatctag gaataatact taaaatatga ttctgcttag taggtttcat tcacacacct 480
agaaaaaaaa atcagtcaat gtttcctttg ggcagaaaat gagcaataat gggtatgcat 540
tgaccactac tgttggacat agccttattg cttcatatag catctattca aagtctcaga 600
tcaacactat gaaaacctgt catctctgta ttagatgatg tgactggggc tgtaaagggt 660

```
aagctctttt cttacagcta tacaacaacg ctaagaccaa gttctgtgct ttgagcccag    720

gcagtttagt ttcccaggag caacctaaag cctgattcac aggcatatgt atgatccaaa    780

ctgaatggta gtacatcaat accaaaacaa tctattggtg gaaacacacc ataggtgatc    840

gaaatactcc attttctttt cctctcatga cttctgttct gagcagtcct cttcctaaag    900

tctacattgt cttctgagtt caggctgaca tcttgacatc ctcctggctg gcacagtctc    960

tggacaagga gggaagaagg agagaagggg aaagggagag gagggggga gggagagaaa    1020

gaatgggaag aggaaggata tgaaagagag aagagaggag ggaaggcggg aggaagggag   1080

ggagggaggg agggagagag ggagagagag gagagagaga gagagagaga gagagagaga   1140

gagagagaga gagagagaga gagagaggga gagggagaga gagacagaga gagagagagg   1200

gagagggaga gagagagaga gagagagaga gagagagaga gagagagaga gtgaggagag   1260

agagagagag ttttcttcac cattggacat tcctaaagaa aagaagtaaa tgcaggattg   1320

gggacagtga cagaggacct ctgataaact ttctgaggcc tctgacctca ctctctcgga   1380

gccctcctcc accacccacc cccccctcc ctagctgaga aaagcttcca ggaaatgtcc    1440

cagtcatcgc ttcccctccc gggctggggg ctgggagcgg gcggtcccct caggccaggg   1500

ctgctccggc cgcgctcggg cagggccaca acagagctgg gaaagctgag cccaggctcg   1560

cagctcctct gggcggagcg ccggctcggt ccccgctgcg ccagccgtga tccccggcag   1620

cctgctcagc a                                                        1631
```

```
<210> SEQ ID NO 30
<211> LENGTH: 75
<212> TYPE: DNA
<213> ORGANISM: Artificial
<220> FEATURE:
<223> OTHER INFORMATION: exon 1 in CHO Protein S

<400> SEQUENCE: 30

atgagggtcc tgagcgtacg ctgtcggcta ctgctggtat gcctagccct ggtgctgcca     60

gcctcggaga caaac                                                      75
```

```
<210> SEQ ID NO 31
<211> LENGTH: 4209
<212> TYPE: DNA
<213> ORGANISM: Artificial
<220> FEATURE:
<223> OTHER INFORMATION: Intron 1 in CHO Protein S
<220> FEATURE:
<221> NAME/KEY: misc_feature
<222> LOCATION: (2647)..(2652)
<223> OTHER INFORMATION: n is a, c, g, or t

<400> SEQUENCE: 31

tgtaagtaat ccatacctcc tggcttctcc attccctatg tgccccggct tgaagatttt     60

ccactaggct gtttgctgcc tcctaagttt ccagtaagtc cgccaccatt cagagagtcg    120

cggcagcctg ggtctggtgg gcagtgtaaa ggtgggacag gatcaaagct tgccttgctt    180

tgagaaccat tgtccacagg acttgattcc agaacccggg tgacactaag tgtcaaagga    240

attgcttgaa catagtccta aatattgcta ggaaagctaa gtcaagcctg ttgccctcct    300

cccgtttaca agagtgcccc agcccgcacc ctctcctgcg gctaaccttc cttttgcaat    360

ttctggactt tgaacttgat tgactggtct cacattgaca aactgtttgg ggactgctgg    420

ggtgttacat atgattctct aaccttgata taagaaatag ctgttggatg ttaccttgta    480

ccgaggatca ttttctgagg gttttgactg ttgccgcttt gagatggcag caagaattct    540
```

```
gtacaacaca cacatttttg tgtttcttgg tctttcctct tcccattctc agattccggg    600
cagtatatcg agttttctct tagaaatata aaacgaacca caaggtttta gtacatttta    660
atggtcaatt aaattgtttt tagaagctta aatatgttca taattaacac tgctttcttt    720
tgctcttttg tagtcccagt cactggcatg ggagcaataa ctgtataaca aataccactt    780
aggtcactgc gagcaccaaa gaaacttttc aaagatggta attaagtagg agtttgctgg    840
aattgcaagt ttttattaat tagtaaggaa tctagcctga tatttttaaa tgtctaacta    900
agttaaagac cagaatgaaa ctggttcact ttttattgag gataaacaag ttacagttat    960
aaagcctcaa caatcaaagc cctacgatga agcagcgtgt gactgtatgc acatgatcta   1020
tcttgttcag aggaacaatc aaacattttc agatagcatc agggcggtgg tggtactcgc   1080
ctataatcct agcaaagtca gaggcaagca gatctctgtg ttcaaggcca gcctagtcta   1140
cagagtgagt tccaggacaa ctggggctac acagagaaac ctgtctcaga gaaaaacaaa   1200
ataaaaccaa attcagatag ctggtgtttg ggaaaagagc aaaagacagc agtgctggcc   1260
acacagagag tagacaagtt cattctacaa ggacatcaca gaaagaatat gtgacccaat   1320
gacgaccata aactttcttg ttcctgtgtc aaattatctc cggtttattg atgaagaacc   1380
agacactatg agctgcgtct cctccttaag attttgtttt ggtgtcttgt ttttgtcaag   1440
gggtttcatt gtggccctga gcattagatc cagggctttg tgcatgctag gccagggagc   1500
tatattcccg aactccagaa gactaggaat ttgagatata aatagaattt gaattacctt   1560
ctgtacaatt gattgtatgg ttctagaaat attgctatat taagggaagc ctttgcagaa   1620
gacagttatt ttgagatggt gcataacaca aaagaaatga actaaagcct gaggcctgct   1680
ctgtagctct gccttgccct tagcctacaa taactttctt tacctttcaa gcatgtgcca   1740
ccacgcctga ctttcaggcc cttcatttta acaagaaagc aagtattcag ttatcaactg   1800
actttccaaa tgcatttgta tgaataaaaa ctacaaaaat ataaaaataa gaactataca   1860
cacaaaagcc ttgtatttaa aatttacgct gtggacatat tttgctcatc attcgtgaga   1920
gcttgcggta aaaaggcaaa ggggaagagg aggatatcta ttttgggtag gctaatttgg   1980
ccttatccag acttcccttt tgggtggatg cagtctgccc agcacactat tggcccattt   2040
cttctacatg gctttgtgct ctgctctgcc cttagctaat tgtccccttt gacatgcttt   2100
tgtctttcct taaagtttct atacttcaaa aaccatcccg ctacactaat ggagtgattt   2160
tctcaagggt tgctttatgt ttggggtttg tactgcaaga gttagtttct gatatagcaa   2220
tggtgatagt atagtcttct accatgaact ctatgccagc aagtacaggg gtatatttca   2280
catgggtgtt ttctgttcac tgagtttcat gtcttctttg tatctttttg ttttgttttg   2340
tgagacaggg tttctctgta gcttttgagt cagtcctgga acttgctggc cggccttgaa   2400
ctcacagaga ttcacctgcc tctgcctccc aagtgctggg atttaaggtg tgagtcacca   2460
ctgccaggtt ttttctttgt atcttgagtg aactaaatag gtaagcttta aataataata   2520
tgagcagtct atttatatac attaaatatt aaatgcattg tgagatgagc atagcctttg   2580
aggcccagga acagaaagat ttacttcaca ttgtaaatat actggtatac atacaaacgt   2640
acatacnnnn nngtgtgtgt gtgtgtgtgt gtgtgtgtgt gcatgccata gcacacatgt   2700
gaagtccaga gtacagcatt ctctttttct acctttctgt agattcttgt ggtcagagtc   2760
aggtcaaatc aaatcagaca gatgcatgta taaaatgctc ttacccactg aaccatcttg   2820
ctgcttggtc cacaagctta gtggaagaat gctgggaagt gaatagtatg tttttaaatg   2880
```

```
tagttaacct tgacttttttg ttgttgttgc tgttattgag gccacatttt cattgttctg   2940

agaaaatatt actattttcc tcagacagaa ttatatattt atttgaagtt catgaattcc   3000

atattatttt cctgtattta ttacaaatag catgcttaaa cacttccaag tagtgaaaca   3060

gctgctcatg taggacacgg attattgaca gtgctgccat ttatcagcca gtaatccact   3120

tggcaggtag cacgctcatc gttatccttt atgcacacaa agccttgttt gaattttatc   3180

ttttaatgag tgtcaatgaa atggaaagag ataagagtta aaaatacaac ccaaactatt   3240

gtatttacat ttctctttta gaagaaacct aaagcagcat tacttcttgc ccatatttaa   3300

taaataacat catttaccct tgttccctgc ctccagactc tcccatatac tcctctttca   3360

attttattgg ccccttttaaa tgacatatca ttacatgtat atccctacac ataagtataa   3420

ccagttcagt ttgtataatg ttacttgcat gtgtgttttc aatgctgatc atttggtagt   3480

ggataaccaa tggtgtgccc tatgaagggg cagagtattt gtatcatgct tagcattcct   3540

ttgttgactg taggattttg tttaaggttg aggtctcttg gtctttcccc tgtctgcttc   3600

tgcatgtcca tggccatcct tgttcagctc atgtttatgt agtcatgctg atgaggcttt   3660

atggatgtag cttctgacat tgctaagcaa cacagtctca gcaaactccc cagtcctctg   3720

gttcttacaa tctttccaca ctgtttcacc atgttgtctg agccttaggt gctgaagttg   3780

ttttgtgtct gtatccattg ggactaggct ccacatgtct gcattttgat tacttgtggt   3840

tttctgtaac ggtctctatg tgttgcaacg agaaggagta gttgctttga cgatgtgtaa   3900

agactatctt gtgggtataa ggacaaatat ttgcatgaag ctatggatta tgctggtctc   3960

aagcatgaac tggataaatt gtacagctca cacaaaacag ctatagctag ctgcacagtc   4020

aggcatgcac tgatctgctt ggggagttgt taaccaaagg gcttacatag ctatgtattt   4080

tctaagctct agttttacta tcacaaagaa aattaattca cccttaattg tttaataaga   4140

tgatatatct tagggaaaaa atgaaggtct ttttttgact tatataaaag cttatgtttt   4200

ctacagttt                                                            4209
```

<210> SEQ ID NO 32
<211> LENGTH: 155
<212> TYPE: DNA
<213> ORGANISM: Artificial
<220> FEATURE:
<223> OTHER INFORMATION: Exon 2 in CHO Protein S

<400> SEQUENCE: 32

```
tgtcaaaaga acatgcctcg caagtcctgg tgaggaagcg ccgcgcaaat accttgcttg     60

aagaaactaa aaagggcaat cttgaaagag aatgcatcga agagctctgc aataaagagg    120

aagccaggga ggtctttgaa aacaatcccg aaacg                               155
```

<210> SEQ ID NO 33
<211> LENGTH: 3239
<212> TYPE: DNA
<213> ORGANISM: Artificial
<220> FEATURE:
<223> OTHER INFORMATION: Intron 2 in CHO Protein S

<400> SEQUENCE: 33

```
gtaagagttc gtggaaatga ccaagtccac actcggatat atattggcag tcagaacact     60

gccagcttga gctaccttgc ttctgtttga aagctaatga cttaggagtt catttctcat    120

gtgttaccac tgacatttca ggcaggctgc caatgacagg cactccagcc aaactccatt    180

tcccttaagt ctcattactc gcaactagta tcgactttat aatgtgtgac tattttatta    240
```

```
tcctaaccaa atctggtagc cttgagggtg caagagaaga tgcgactgaa gggtaagtga    300
ccatatatgt acttgcattg tcactgtgct tttgttttgg ttgattgtgt ttgagacagt    360
ctcttactct gtagctccaa ctacaaggag ctccctatcc atctgctttg gcttcagcct    420
cccaagtact gtgattatag actggtgtgt cttgccattt atctttaaga ggctctagat    480
agaaatgggg ccacctaact gagattagtc attacagcat tatgtatgct gactgtatac    540
tattctgtaa ccttcatgaa gtttcccgag gccactgata atcagcagta atcattagtg    600
tctaaaaatt tccaagttac ccacccgcca aacataacat aaagacagca acatgggact    660
ctttgtccat tctgtgtttc aggagagggc aatttatagt atgcttgtaa ctaacaggag    720
tagcattaat atctccaagg agcactttga gcatgacctt gagagtctac atggaacact    780
gttcagggtc tcctcagatg ttctacctga gctgaattat acaatctgga ggaaaagaaa    840
gagatgacat acacaaggct cctcctttgc ctctgccaca gctcccagaa ccatgacaac    900
agctgagtga taaagagcaa ggactctttg tccatactta gaaaatttgt ccccaactgt    960
agctacttgt ggtctgtggt tgttattgta gctctttttt aatccctatg tgttctgata   1020
ggttcaaaga agaaattttc cccaaatatg caacaattaa attttaatct acctagaatt   1080
gagacaaaaa tgtgacgaaa taccttgatc aaaaaaacaa ctcaggagga aagggttttt   1140
tttttttttt ttggtttact aacctgaatt gagggaagca aaagtaggag ctcaaaccag   1200
gtgggaacct ggaggcagga gctgatgcag aggcatggag gagtgctgct tactggtctg   1260
ctcctcatgg cttgctcagc ttgttttctt atagaaccca gggccaccgt cacaaaagta   1320
ccatcacctg caatgggttg ggcccttccc cagggatctc tgattaagaa aattccctac   1380
aggtctgtct acaattcttt tttgtttgtt tgtttgtttg tttgtttgtt tgttttcgag   1440
acagggtttg tctgtatagc tttggagcct gtcctggaac tcactctgta gaccaggttg   1500
gcctcgaagt cacaaagatc cacctgcctt tgcctcccta gtgctgggat taaaggcttg   1560
tgtcaccact gccaggccta ttttaaggaa gcatttttct ccttgagatt ccttcctctc   1620
aaatgattct agcttgtatc aagttgacat aaaattagcc agcacagaca acaacaatag   1680
aaaatttttct atcctacaca atgtaataaa tttattgggt aggatttaac atatgtattc   1740
tatgttttac attctcattc taaaaaggaa tgtgtatgca ctcttacaaa cttccataat   1800
acaaaagaat acagtatgta ttagatatgt gcatatattc cttccccttta tggaaagttt   1860
aaaaagtaga aagaatggta taataaactg caacacaaca cgtccctcta ataagatcaa   1920
ggctttcatt tgattttgcc tatccaccac atctaatcaa tggttttgct ttgagcaatc   1980
aagtcacatg attatattac ccatacttga gttgtatatc tgcattgtag atatgttctc   2040
aaagctcagc ctttaaagag tagtagggag ggaagatgga ccacaggaag aagggggagg   2100
aaggtgaaga aggaaaacac attcgtgttt ctttaccttc actaatagtt ttgttgacag   2160
attccaccta ctccctgtcc atatccctca tactcttagg ccagtattcc cagtgttatt   2220
gaccctgatg tttacctgtt cgcttgtcat cagcatgtca ccaatcttta aatgccattg   2280
tttgtctcct tattgtcttg tctctgcttc tgcagtaaac aacactgttg tctgaatgag   2340
tcagtgtcag gcccctttct tataagccag tagaaacgtg caagtttgta catgataaga   2400
ggaaagagtg tagattttga tgtagaaaaa gccaagctcc actctaagcc agaattttga   2460
atacttttta tgcagaaatt ttgtttttgt atgaaatatt cttgtgttat ttatttacat   2520
tatgagtgta ctgtcagaag ctcataaaaa ttaccctgtt cataaaatac attccttcat   2580
```

```
ccatatgtca tcattatttt gctatccatc aatatataag gaaggtgttt cacatgcatt   2640

agatgcaata aggtaagtgg tcattttagt tctctttaaa tgatttcatt gttgactcca   2700

gtgtagatag tcatcatggc ataagatgta tcaaatgaag actaggtgtg gtggtgcata   2760

ccttcagtcc cagcacacag aggcagagga acatggattg ctgtgagttt caggtggacc   2820

tggtctacat agtgagttcc aaggtagata gagggtgtct cgagagaccc tgtaagaaaa   2880

gtctatgttt aattgccatg aaaaaattag aggattataa aagagggaat atattgttat   2940

agttatcaac tacaaccagt tcaaatcaga agctttaaaa tgttatttta ttgttcagta   3000

gtgttttaag catatatatg tatacacaca aacatatatg tgtttatata tatgtatatg   3060

tatactggtc aagtattggc tatctattct tgaagtattt atagaaaaat tagaaatgtg   3120

aaaacataca acatgtaggt catttccata ttcatataaa agcaaattag aaaaattaat   3180

ctttaactct gtagtgatat ttgagtttgc taatatctat tttttattt tctttctag    3239
```

<210> SEQ ID NO 34
<211> LENGTH: 25
<212> TYPE: DNA
<213> ORGANISM: Artificial
<220> FEATURE:
<223> OTHER INFORMATION: exon3 in CHO Protein S

<400> SEQUENCE: 34

```
gattatttt atccaaaata tttgg                                          25
```

<210> SEQ ID NO 35
<211> LENGTH: 15
<212> TYPE: DNA
<213> ORGANISM: Artificial
<220> FEATURE:
<223> OTHER INFORMATION: DNA element from the CHO Protein S promoter

<400> SEQUENCE: 35

```
ggagaggagg ggggg                                                    15
```

<210> SEQ ID NO 36
<211> LENGTH: 21
<212> TYPE: PRT
<213> ORGANISM: Artificial
<220> FEATURE:
<223> OTHER INFORMATION: Zinc finger motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(9)
<223> OTHER INFORMATION: Xaa can be any naturally occurring amino acid
<220> FEATURE:
<221> NAME/KEY: misc_feature
<222> LOCATION: (18)..(20)
<223> OTHER INFORMATION: Xaa can be any naturally occurring amino acid

<400> SEQUENCE: 36

```
Cys Xaa Xaa Cys Xaa Xaa Xaa Xaa Xaa Gln Ser Gly His Leu Gln Arg
1               5                   10                  15

His Xaa Xaa Xaa His
            20
```

<210> SEQ ID NO 37
<211> LENGTH: 23
<212> TYPE: PRT
<213> ORGANISM: Artificial

<220> FEATURE:
<223> OTHER INFORMATION: Zinc finger motif
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(11)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid

<400> SEQUENCE: 37

Cys Xaa Xaa Xaa Xaa Cys Xaa Xaa Xaa Xaa Xaa Arg Ser Asp Asn Leu
1 5 10 15

Ala Arg His Xaa Xaa Xaa His
20

<210> SEQ ID NO 38
<211> LENGTH: 21
<212> TYPE: PRT
<213> ORGANISM: Artificial
<220> FEATURE:
<223> OTHER INFORMATION: Zinc finger motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(9)
<223> OTHER INFORMATION: Xaa can be any naturally occurring amino acid
<220> FEATURE:
<221> NAME/KEY: misc_feature
<222> LOCATION: (18)..(20)
<223> OTHER INFORMATION: Xaa can be any naturally occurring amino acid

<400> SEQUENCE: 38

Cys Xaa Xaa Cys Xaa Xaa Xaa Xaa Xaa Arg Ser Asp Asn Leu Thr Arg
1 5 10 15

His Xaa Xaa Xaa His
20

<210> SEQ ID NO 39
<211> LENGTH: 23
<212> TYPE: PRT
<213> ORGANISM: Artificial
<220> FEATURE:
<223> OTHER INFORMATION: Zinc finger motif
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(11)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid

<400> SEQUENCE: 39

Cys Xaa Xaa Xaa Xaa Cys Xaa Xaa Xaa Xaa Xaa Arg Ser Asp His Leu
1 5 10 15

Thr Arg His Xaa Xaa Xaa His
20

<210> SEQ ID NO 40
<211> LENGTH: 23
<212> TYPE: PRT
<213> ORGANISM: Artificial
<220> FEATURE:
<223> OTHER INFORMATION: Zinc finger motif
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(11)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid

<400> SEQUENCE: 40

```
Cys Xaa Xaa Xaa Xaa Cys Xaa Xaa Xaa Xaa Xaa Arg Ser Asp His Leu
1               5                   10                  15

Ala Arg His Xaa Xaa Xaa His
            20
```

<210> SEQ ID NO 41
<211> LENGTH: 15
<212> TYPE: PRT
<213> ORGANISM: Artificial
<220> FEATURE:
<223> OTHER INFORMATION: Protein sequence target

<400> SEQUENCE: 41

```
Gly Gly Ala Gly Ala Gly Gly Ala Gly Gly Gly Gly Gly Gly Gly
1               5                   10                  15
```

<210> SEQ ID NO 42
<211> LENGTH: 321
<212> TYPE: PRT
<213> ORGANISM: Artificial
<220> FEATURE:
<223> OTHER INFORMATION: ZNF-PS protein sequence

<400> SEQUENCE: 42

```
Met Asp Ala Lys Ser Leu Thr Ala Trp Ser Arg Thr Leu Val Thr Phe
1               5                   10                  15

Lys Asp Val Phe Val Asp Phe Thr Arg Glu Glu Trp Lys Leu Leu Asp
            20                  25                  30

Thr Ala Gln Gln Ile Val Tyr Arg Asn Val Met Leu Glu Asn Tyr Lys
        35                  40                  45

Asn Leu Val Ser Leu Gly Tyr Gln Leu Thr Lys Pro Asp Val Ile Leu
    50                  55                  60

Arg Leu Glu Lys Gly Glu Glu Pro Trp Leu Val Glu Arg Glu Ile His
65                  70                  75                  80

Gln Glu Thr His Pro Asp Ser Glu Thr Ala Phe Glu Ile Lys Ser Ser
                85                  90                  95

Val Ser Ser Arg Ser Ile Phe Lys Asp Lys Gln Ser Cys Asp Ile Lys
            100                 105                 110

Met Glu Gly Met Ala Arg Asn Asp Leu Trp Tyr Leu Ser Leu Glu Glu
        115                 120                 125

Val Trp Lys Pro Gly Lys Lys Lys Gln His Ile Cys His Ile Gln Gly
    130                 135                 140
```

```
Cys Gly Lys Val Tyr Gly Arg Ser Asp His Leu Ala Arg His Leu Arg
145                 150                 155                 160

Trp His Thr Gly Glu Arg Pro Phe Met Cys Thr Trp Ser Tyr Cys Gly
                165                 170                 175

Lys Arg Phe Thr Arg Ser Asp His Leu Thr Arg His Lys Arg Thr His
            180                 185                 190

Thr Gly Glu Lys Lys Phe Ala Cys Pro Glu Cys Pro Lys Arg Phe Met
        195                 200                 205

Arg Ser Asp Asn Leu Thr Arg His Ile Lys Thr His Thr Gly Glu Arg
    210                 215                 220

Pro Phe Ala Cys Asp Trp Gln Gly Cys Asp Lys Lys Phe Ala Arg Ser
225                 230                 235                 240

Asp Asn Leu Ala Arg His His Arg Thr His Thr Gly Glu Lys Arg Phe
                245                 250                 255

Ser Cys Pro Leu Cys Ser Lys Arg Phe Thr Gln Ser Gly His Leu Gln
            260                 265                 270

Arg His Ala Arg Arg His Pro Gly Phe His Pro Asp Leu Leu Arg Arg
        275                 280                 285

Pro Gly Ala Arg Ser Thr Ser Pro Ser Asp Ser Leu Pro Cys Ser Leu
    290                 295                 300

Ala Gly Ser Pro Ala Pro Ser Pro Ala Pro Ser Pro Ala Pro Ala Gly
305                 310                 315                 320

Leu


<210> SEQ ID NO 43
<211> LENGTH: 4364
<212> TYPE: DNA
<213> ORGANISM: Artificial
<220> FEATURE:
<223> OTHER INFORMATION: DNA Probe
<220> FEATURE:
<221> NAME/KEY: misc_feature
<222> LOCATION: (2692)..(2697)
<223> OTHER INFORMATION: n is a, c, g, or t

<400> SEQUENCE: 43

ctgctggtat gcctagccct ggtgctgcca gcctcggaga caaactgtaa gtaatccata     60

cctcctggct tctccattcc ctatgtgccc cggcttgaag attttccact aggctgtttg    120

ctgcctccta agtttccagt aagtccgcca ccattcagag agtcgcggca gcctgggtct    180

ggtgggcagt gtaaaggtgg gacaggatca aagcttgcct tgctttgaga accattgtcc    240

acaggacttg attccagaac ccgggtgaca ctaagtgtca aaggaattgc ttgaacatag    300

tcctaaatat tgctaggaaa gctaagtcaa gcctgttgcc ctcctcccgt ttacaagagt    360

gccccagccc gcaccctctc ctgcggctaa ccttcctttt gcaatttctg gactttgaac    420

ttgattgact ggtctcacat tgacaaactg tttggggact gctggggtgt tacatatgat    480

tctctaacct tgatataaga aatagctgtt ggatgttacc ttgtaccgag gatcattttc    540

tgagggtttt gactgttgcc gctttgagat ggcagcaaga attctgtaca acacacacat    600

ttttgtgttt cttggtcttt cctcttccca ttctcagatt ccgggcagta tatcgagttt    660

tctcttagaa atataaaacg aaccacaagg ttttagtaca ttttaatggt caattaaatt    720

gtttttagaa gcttaaatat gttcataatt aacactgctt tcttttgctc ttttgtagtc    780

ccagtcactg gcatgggagc aataactgta taacaaatac cacttaggtc actgcgagca    840

ccaaagaaac ttttcaaaga tggtaattaa gtaggagttt gctggaattg caagttttta    900
```

-continued

```
ttaattagta aggaatctag cctgatattt ttaaatgtct aactaagtta aagaccagaa    960
tgaaactggt tcacttttta ttgaggataa acaagttaca gttataaagc ctcaacaatc   1020
aaagccctac gatgaagcag cgtgtgactg tatgcacatg atctatcttg ttcagaggaa   1080
caatcaaaca ttttcagata gcatcagggc ggtggtggta ctcgcctata atcctagcaa   1140
agtcagaggc aagcagatct ctgtgttcaa ggccagccta gtctacagag tgagttccag   1200
gacaactggg gctacacaga gaaacctgtc tcagagaaaa acaaaataaa accaaattca   1260
gatagctggt gtttgggaaa agagcaaaag acagcagtgc tggccacaca gagagtagac   1320
aagttcattc tacaaggaca tcacagaaag aatatgtgac ccaatgacga ccataaactt   1380
tcttgttcct gtgtcaaatt atctccggtt tattgatgaa gaaccagaca ctatgagctg   1440
cgtctcctcc ttaagatttt gttttggtgt cttgtttttg tcaaggggtt tcattgtggc   1500
cctgagcatt agatccaggg ctttgtgcat gctaggccag ggagctatat tcccgaactc   1560
cagaagacta ggaatttgag atataaatag aatttgaatt accttctgta caattgattg   1620
tatggttcta gaaatattgc tatattaagg gaagcctttg cagaagacag ttattttgag   1680
atggtgcata acacaaaaga aatgaactaa agcctgaggc ctgctctgta gctctgcctt   1740
gcccttagcc tacaataact ttctttacct ttcaagcatg tgccaccacg cctgactttc   1800
aggcccttca ttttaacaag aaagcaagta ttcagttatc aactgacttt ccaaatgcat   1860
ttgtatgaat aaaaactaca aaaatataaa aataagaact atacacacaa aagccttgta   1920
tttaaaattt acgctgtgga catattttgc tcatcattcg tgagagcttg cggtaaaaag   1980
gcaaagggga agaggaggat atctattttg ggtaggctaa tttggcctta tccagacttc   2040
ccttttgggt ggatgcagtc tgcccagcac actattggcc catttcttct acatggcttt   2100
gtgctctgct ctgcccttag ctaattgtcc cctttgacat gcttttgtct ttccttaaag   2160
tttctatact tcaaaaacca tcccgctaca ctaatggagt gattttctca agggttgctt   2220
tatgtttggg gtttgtactg caagagttag tttctgatat agcaatggtg atagtatagt   2280
cttctaccat gaactctatg ccagcaagta caggggtata tttcacatgg gtgttttctg   2340
ttcactgagt ttcatgtctt ctttgtatct ttttgttttg ttttgtgaga cagggtttct   2400
ctgtagcttt tgagtcagtc ctggaacttg ctggccggcc ttgaactcac agagattcac   2460
ctgcctctgc ctcccaagtg ctgggattta aggtgtgagt caccactgcc aggtttttttc   2520
tttgtatctt gagtgaacta aataggtaag ctttaaataa taatatgagc agtctattta   2580
tatacattaa atattaaatg cattgtgaga tgagcatagc ctttgaggcc caggaacaga   2640
aagatttact tcacattgta aatatactgg tatacataca aacgtacata cnnnnnnngtg   2700
tgtgtgtgtg tgtgtgtgtg tgtgtgcatg ccatagcaca catgtgaagt ccagagtaca   2760
gcattctctt tttctacctt tctgtagatt cttgtggtca gagtcaggtc aaatcaaatc   2820
agacagatgc atgtataaaa tgctcttacc cactgaacca tcttgctgct tggtccacaa   2880
gcttagtgga agaatgctgg gaagtgaata gtatgttttt aaatgtagtt aaccttgact   2940
ttttgttgtt gttgctgtta ttgaggccac attttcattg ttctgagaaa atattactat   3000
tttcctcaga cagaattata tatttatttg aagttcatga attccatatt attttcctgt   3060
atttattaca aatagcatgc ttaaacactt ccaagtagtg aaacagctgc tcatgtagga   3120
cacggattat tgacagtgct gccatttatc agccagtaat ccacttggca ggtagcacgc   3180
tcatcgttat cctttatgca cacaaagcct tgtttgaatt ttatctttta atgagtgtca   3240
atgaaatgga aagagataag agttaaaaat acaacccaaa ctattgtatt tacatttctc   3300
```

```
ttttagaaga aacctaaagc agcattactt cttgcccata tttaataaat aacatcattt   3360

acccttgttc cctgcctcca gactctccca tatactcctc tttcaatttt attggcccct   3420

ttaaatgaca tatcattaca tgtatatccc tacacataag tataaccagt tcagtttgta   3480

taatgttact tgcatgtgtg ttttcaatgc tgatcatttg gtagtggata accaatggtg   3540

tgccctatga aggggcagag tatttgtatc atgcttagca ttcctttgtt gactgtagga   3600

ttttgtttaa ggttgaggtc tcttggtctt tcccctgtct gcttctgcat gtccatggcc   3660

atccttgttc agctcatgtt tatgtagtca tgctgatgag gctttatgga tgtagcttct   3720

gacattgcta agcaacacag tctcagcaaa ctccccagtc ctctggttct tacaatcttt   3780

ccacactgtt tcaccatgtt gtctgagcct taggtgctga agttgttttg tgtctgtatc   3840

cattgggact aggctccaca tgtctgcatt ttgattactt gtggttttct gtaacggtct   3900

ctatgtgttg caacgagaag gagtagttgc tttgacgatg tgtaaagact atcttgtggg   3960

tataaggaca aatatttgca tgaagctatg gattatgctg gtctcaagca tgaactggat   4020

aaattgtaca gctcacacaa aacagctata gctagctgca cagtcaggca tgcactgatc   4080

tgcttgggga gttgttaacc aaagggctta catagctatg tattttctaa gctctagttt   4140

tactatcaca aagaaaatta attcaccctt aattgtttaa taagatgata tatcttaggg   4200

aaaaaatgaa ggtctttttt tgacttatat aaaagcttat gttttctaca gttttgtcaa   4260

aagaacatgc ctcgcaagtc ctggtgagga agcgccgcgc aaataccttg cttgaagaaa   4320

ctaaaaaggg caatcttgaa agagaatgca tcgaagagct ctgc                    4364
```

```
<210> SEQ ID NO 44
<211> LENGTH: 948
<212> TYPE: DNA
<213> ORGANISM: Artificial
<220> FEATURE:
<223> OTHER INFORMATION: DNA Probe

<400> SEQUENCE: 44

atgaagctac tgtcttctat cgaacaagca tgcccaaaaa agaagagaaa ggtagatgaa     60

aaaccttaca agtgtccgga atgtgggaag tcctttagtc ggagcgacaa cctggcccgg    120

caccagcgga cgcataccgg tgagaagccc tacaaatgcc cagaatgcgg aaaatcattt    180

tcgcggagca gcaacctgcg ggagcaccaa cgaacccaca caggcgagaa accatttaaa    240

tgtcctgagt gtggtaagag ctttagccgg agcgacaacc tgacccggca tcaagctact    300

catacgggcg gcggtggcag cggtggcggt agcggcggtg gcagcggtgg cggatcccaa    360

ctagtcaaaa gtgaactgga ggagaagaaa tctgaacttc gtcataaatt gaaatatgtg    420

cctcatgaat atattgaatt aattgaaatt gccagaaatt ccactcagga tagaattctt    480

gaaatgaagg taatggaatt ttttatgaaa gtttatggat atagaggtaa acatttgggt    540

ggatcaagga aaccggacgg agcaatttat actgtcggat ctcctattga ttacggtgtg    600

atcgtggata ctaaagctta tagcggaggt tataatctgc caattggcca agcagatgaa    660

atgcaacgat atgtcgaaga aaatcaaaca cgaaacaaac atatcaaccc taatgaatgg    720

tggaaagtct atccatcttc tgtaacggaa tttaagtttt tatttgtgag tggtcacttt    780

aaaggaaact acaaagctca gcttacacga ttaaatcata tcactaattg taatggagct    840

gttcttagtg tagaagagct tttaattggt ggagaaatga ttaaagccgg cacattaacc    900

ttagaggaag tgagacggaa atttaataac ggcgagataa acttttag                 948
```

<210> SEQ ID NO 45
<211> LENGTH: 978
<212> TYPE: DNA
<213> ORGANISM: Artificial
<220> FEATURE:
<223> OTHER INFORMATION: DNA Probe

<400> SEQUENCE: 45

```
atgaagctac tgtcttctat cgaacaagca tgcccaaaaa agaagagaaa ggtagatgaa      60

aaaccttaca agtgtccgga atgtgggaag tcctttagtc ggagcgacaa cctggcccgg     120

caccagcgga cgcataccgg tgagaagccc tacaaatgcc cagaatgcgg aaaatcattt     180

tcgcggagca gcaacctgcg ggagcaccaa cgaacccaca caggcgagaa accatttaaa     240

tgtcctgagt gtggtaagag ctttagccgg agcgacaacc tgacccggca tcaagctact     300

catacgggcg gcggtggcag cggtggcggt agcggcggtg gcagcggtgg cggatccgta     360

ttagaaaaaa gtgatattga aaaatttaag aatcaattgc gtacggaact aaccaatatt     420

gaccattctt atcttaaagg aattgatata gctagtaaaa agaaaaccag taatgttgaa     480

aatacggaat ttgaagcaat atcaaccaag atttttacgg atgagttggg tttttcaggc     540

aaacatctag gaggaagcaa caaaccagat ggactcctgt gggatgatga ttgtgcaatt     600

attcttgatt caaaagctta ctcagaaggc tttccactca ctgcctccca cacagatgct     660

atgggaagat atttgaggca atttacagag cgaaaagaag aaataaagcc aacgtggtgg     720

gatattgctc cagaacattt agacaataca tatttcgctt acgtttctgg gagtttttcg     780

ggtaattata aggaacagtt acaaaaattt aggcaagata caaaccattt aggtggggca     840

ctagagtttg ttaaattgtt attactagca aataattata aaactcaaaa aatgagtaaa     900

aaagaagtta agaaaagtat tcttgattat aatatttcat atgaagaata tgctccatta     960

cttgcagaaa tagagtaa                                                   978
```

<210> SEQ ID NO 46
<211> LENGTH: 948
<212> TYPE: DNA
<213> ORGANISM: Artificial
<220> FEATURE:
<223> OTHER INFORMATION: DNA Probe

<400> SEQUENCE: 46

```
atgaagctac tgtcttctat cgaacaagca tgcccaaaaa agaagagaaa ggtagatgaa      60

aaaccttaca agtgtccgga atgtgggaag tcctttagtc ggagcgacgc cctgacccag     120

caccagcgga cgcataccgg tgagaagccc tacaaatgcc cagaatgcgg aaaatcattt     180

tcgcagagca gccacctggc ccggcaccaa cgaacccaca caggcgagaa accatttaaa     240

tgtcctgagt gtggtaagag ctttagccag agcagccacc tgacccggca tcaagctact     300

catacgggcg gcggtggcag cggtggcggt agcggcggtg gcagcggtgg cggatcccaa     360

ctagtcaaaa gtgaactgga ggagaagaaa tctgaacttc gtcataaatt gaaatatgtg     420

cctcatgaat atattgaatt aattgaaatt gccagaaatt ccactcagga tagaattctt     480

gaaatgaagg taatggaatt ttttatgaaa gtttatggat atagaggtaa acatttgggt     540

ggatcaagga aaccggacgg agcaatttat actgtcggat ctcctattga ttacggtgtg     600

atcgtggata ctaaagctta tagcggaggt tataatctgc caattggcca agcagatgaa     660

atgcaacgat atgtcgaaga aaatcaaaca cgaaacaaac atatcaaccc taatgaatgg     720

tggaaagtct atccatcttc tgtaacggaa tttaagtttt tatttgtgag tggtcacttt     780
```

```
aaaggaaact acaaagctca gcttacacga ttaaatcata tcactaattg taatggagct    840

gttcttagtg tagaagagct tttaattggt ggagaaatga ttaaagccgg cacattaacc    900

ttagaggaag tgagacggaa atttaataac ggcgagataa acttttag                 948
```

```
<210> SEQ ID NO 47
<211> LENGTH: 978
<212> TYPE: DNA
<213> ORGANISM: Artificial
<220> FEATURE:
<223> OTHER INFORMATION: DNA Probe

<400> SEQUENCE: 47

atgaagctac tgtcttctat cgaacaagca tgcccaaaaa agaagagaaa ggtagatgaa     60

aaaccttaca agtgtccgga atgtgggaag tcctttagtc ggagcgacgc cctgacccag    120

caccagcgga cgcataccgg tgagaagccc tacaaatgcc cagaatgcgg aaaatcattt    180

tcgcagagca gccacctggc ccggcaccaa cgaacccaca caggcgagaa accatttaaa    240

tgtcctgagt gtggtaagag ctttagccag agcagccacc tgacccggca tcaagctact    300

catacgggcg gcggtggcag cggtggcggt agcggcggtg gcagcggtgg cggatccgta    360

ttagaaaaaa gtgatattga aaaatttaag aatcaattgc gtacggaact aaccaatatt    420

gaccattctt atcttaaagg aattgatata gctagtaaaa agaaaaccag taatgttgaa    480

aatacggaat ttgaagcaat atcaaccaag atttttacgg atgagttggg tttttcaggc    540

aaacatctag gaggaagcaa caaaccagat ggactcctgt gggatgatga ttgtgcaatt    600

attcttgatt caaaagctta ctcagaaggc tttccactca ctgcctccca cacagatgct    660

atgggaagat atttgaggca atttacagag cgaaaagaag aaataaagcc aacgtggtgg    720

gatattgctc cagaacattt agacaataca tatttcgctt acgtttctgg gagtttttcg    780

ggtaattata aggaacagtt acaaaaattt aggcaagata caaaccattt aggtggggca    840

ctagagtttg ttaaattgtt attactagca aataattata aaactcaaaa aatgagtaaa    900

aaagaagtta agaaaagtat tcttgattat aatatttcat atgaagaata tgctccatta    960

cttgcagaaa tagagtaa                                                  978
```

```
<210> SEQ ID NO 48
<211> LENGTH: 315
<212> TYPE: PRT
<213> ORGANISM: Artificial
<220> FEATURE:
<223> OTHER INFORMATION: Left zinc finger-Fok I protein sequence

<400> SEQUENCE: 48

Met Lys Leu Leu Ser Ser Ile Glu Gln Ala Cys Pro Lys Lys Lys Arg
1               5                   10                  15

Lys Val Asp Glu Lys Pro Tyr Lys Cys Pro Glu Cys Gly Lys Ser Phe
            20                  25                  30

Ser Arg Ser Asp Asn Leu Ala Arg His Gln Arg Thr His Thr Gly Glu
        35                  40                  45

Lys Pro Tyr Lys Cys Pro Glu Cys Gly Lys Ser Phe Ser Arg Ser Ser
    50                  55                  60

Asn Leu Arg Glu His Gln Arg Thr His Thr Gly Glu Lys Pro Phe Lys
65                  70                  75                  80

Cys Pro Glu Cys Gly Lys Ser Phe Ser Arg Ser Asp Asn Leu Thr Arg
                85                  90                  95
```

```
His Gln Ala Thr His Thr Gly Gly Gly Gly Ser Gly Gly Gly Ser Gly
            100                 105                 110

Gly Gly Ser Gly Gly Gly Ser Gln Leu Val Lys Ser Glu Leu Glu Glu
        115                 120                 125

Lys Lys Ser Glu Leu Arg His Lys Leu Lys Tyr Val Pro His Glu Tyr
    130                 135                 140

Ile Glu Leu Ile Glu Ile Ala Arg Asn Ser Thr Gln Asp Arg Ile Leu
145                 150                 155                 160

Glu Met Lys Val Met Glu Phe Phe Met Lys Val Tyr Gly Tyr Arg Gly
                165                 170                 175

Lys His Leu Gly Gly Ser Arg Lys Pro Asp Gly Ala Ile Tyr Thr Val
            180                 185                 190

Gly Ser Pro Ile Asp Tyr Gly Val Ile Val Asp Thr Lys Ala Tyr Ser
        195                 200                 205

Gly Gly Tyr Asn Leu Pro Ile Gly Gln Ala Asp Glu Met Gln Arg Tyr
    210                 215                 220

Val Glu Glu Asn Gln Thr Arg Asn Lys His Ile Asn Pro Asn Glu Trp
225                 230                 235                 240

Trp Lys Val Tyr Pro Ser Ser Val Thr Glu Phe Lys Phe Leu Phe Val
                245                 250                 255

Ser Gly His Phe Lys Gly Asn Tyr Lys Ala Gln Leu Thr Arg Leu Asn
            260                 265                 270

His Ile Thr Asn Cys Asn Gly Ala Val Leu Ser Val Glu Glu Leu Leu
        275                 280                 285

Ile Gly Gly Glu Met Ile Lys Ala Gly Thr Leu Thr Leu Glu Glu Val
    290                 295                 300

Arg Arg Lys Phe Asn Asn Gly Glu Ile Asn Phe
305                 310                 315
```

<210> SEQ ID NO 49
<211> LENGTH: 325
<212> TYPE: PRT
<213> ORGANISM: Artificial
<220> FEATURE:
<223> OTHER INFORMATION: Left zinc finger-Sts I protein sequence

<400> SEQUENCE: 49

```
Met Lys Leu Leu Ser Ser Ile Glu Gln Ala Cys Pro Lys Lys Lys Arg
1               5                   10                  15

Lys Val Asp Glu Lys Pro Tyr Lys Cys Pro Glu Cys Gly Lys Ser Phe
            20                  25                  30

Ser Arg Ser Asp Asn Leu Ala Arg His Gln Arg Thr His Thr Gly Glu
        35                  40                  45

Lys Pro Tyr Lys Cys Pro Glu Cys Gly Lys Ser Phe Ser Arg Ser Ser
    50                  55                  60

Asn Leu Arg Glu His Gln Arg Thr His Thr Gly Glu Lys Pro Phe Lys
65                  70                  75                  80

Cys Pro Glu Cys Gly Lys Ser Phe Ser Arg Ser Asp Asn Leu Thr Arg
                85                  90                  95

His Gln Ala Thr His Thr Gly Gly Gly Gly Ser Gly Gly Gly Ser Gly
            100                 105                 110

Gly Gly Ser Gly Gly Gly Ser Val Leu Glu Lys Ser Asp Ile Glu Lys
        115                 120                 125

Phe Lys Asn Gln Leu Arg Thr Glu Leu Thr Asn Ile Asp His Ser Tyr
    130                 135                 140
```

```
Leu Lys Gly Ile Asp Ile Ala Ser Lys Lys Lys Thr Ser Asn Val Glu
145                 150                 155                 160

Asn Thr Glu Phe Glu Ala Ile Ser Thr Lys Ile Phe Thr Asp Glu Leu
                165                 170                 175

Gly Phe Ser Gly Lys His Leu Gly Gly Ser Asn Lys Pro Asp Gly Leu
            180                 185                 190

Leu Trp Asp Asp Asp Cys Ala Ile Ile Leu Asp Ser Lys Ala Tyr Ser
        195                 200                 205

Glu Gly Phe Pro Leu Thr Ala Ser His Thr Asp Ala Met Gly Arg Tyr
    210                 215                 220

Leu Arg Gln Phe Thr Glu Arg Lys Glu Glu Ile Lys Pro Thr Trp Trp
225                 230                 235                 240

Asp Ile Ala Pro Glu His Leu Asp Asn Thr Tyr Phe Ala Tyr Val Ser
                245                 250                 255

Gly Ser Phe Ser Gly Asn Tyr Lys Glu Gln Leu Gln Lys Phe Arg Gln
            260                 265                 270

Asp Thr Asn His Leu Gly Gly Ala Leu Glu Phe Val Lys Leu Leu Leu
        275                 280                 285

Leu Ala Asn Asn Tyr Lys Thr Gln Lys Met Ser Lys Lys Glu Val Lys
    290                 295                 300

Lys Ser Ile Leu Asp Tyr Asn Ile Ser Tyr Glu Glu Tyr Ala Pro Leu
305                 310                 315                 320

Leu Ala Glu Ile Glu
                325
```

<210> SEQ ID NO 50
<211> LENGTH: 315
<212> TYPE: PRT
<213> ORGANISM: Artificial
<220> FEATURE:
<223> OTHER INFORMATION: Right zinc finger-Fok I protein sequence

<400> SEQUENCE: 50

```
Met Lys Leu Leu Ser Ser Ile Glu Gln Ala Cys Pro Lys Lys Lys Arg
1               5                   10                  15

Lys Val Asp Glu Lys Pro Tyr Lys Cys Pro Glu Cys Gly Lys Ser Phe
            20                  25                  30

Ser Arg Ser Asp Ala Leu Thr Gln His Gln Arg Thr His Thr Gly Glu
        35                  40                  45

Lys Pro Tyr Lys Cys Pro Glu Cys Gly Lys Ser Phe Ser Gln Ser Ser
    50                  55                  60

His Leu Ala Arg His Gln Arg Thr His Thr Gly Glu Lys Pro Phe Lys
65                  70                  75                  80

Cys Pro Glu Cys Gly Lys Ser Phe Ser Gln Ser Ser His Leu Thr Arg
                85                  90                  95

His Gln Ala Thr His Thr Gly Gly Gly Gly Ser Gly Gly Gly Ser Gly
            100                 105                 110

Gly Gly Ser Gly Gly Gly Ser Gln Leu Val Lys Ser Glu Leu Glu Glu
        115                 120                 125

Lys Lys Ser Glu Leu Arg His Lys Leu Lys Tyr Val Pro His Glu Tyr
    130                 135                 140

Ile Glu Leu Ile Glu Ile Ala Arg Asn Ser Thr Gln Asp Arg Ile Leu
145                 150                 155                 160

Glu Met Lys Val Met Glu Phe Phe Met Lys Val Tyr Gly Tyr Arg Gly
                165                 170                 175
```

```
Lys His Leu Gly Gly Ser Arg Lys Pro Asp Gly Ala Ile Tyr Thr Val
            180                 185                 190

Gly Ser Pro Ile Asp Tyr Gly Val Ile Val Asp Thr Lys Ala Tyr Ser
        195                 200                 205

Gly Gly Tyr Asn Leu Pro Ile Gly Gln Ala Asp Glu Met Gln Arg Tyr
    210                 215                 220

Val Glu Glu Asn Gln Thr Arg Asn Lys His Ile Asn Pro Asn Glu Trp
225                 230                 235                 240

Trp Lys Val Tyr Pro Ser Ser Val Thr Glu Phe Lys Phe Leu Phe Val
                245                 250                 255

Ser Gly His Phe Lys Gly Asn Tyr Lys Ala Gln Leu Thr Arg Leu Asn
            260                 265                 270

His Ile Thr Asn Cys Asn Gly Ala Val Leu Ser Val Glu Glu Leu Leu
        275                 280                 285

Ile Gly Gly Glu Met Ile Lys Ala Gly Thr Leu Thr Leu Glu Glu Val
    290                 295                 300

Arg Arg Lys Phe Asn Asn Gly Glu Ile Asn Phe
305                 310                 315


<210> SEQ ID NO 51
<211> LENGTH: 325
<212> TYPE: PRT
<213> ORGANISM: Artificial
<220> FEATURE:
<223> OTHER INFORMATION: Right zinc finger-Sts I protein sequence

<400> SEQUENCE: 51

Met Lys Leu Leu Ser Ser Ile Glu Gln Ala Cys Pro Lys Lys Lys Arg
1               5                   10                  15

Lys Val Asp Glu Lys Pro Tyr Lys Cys Pro Glu Cys Gly Lys Ser Phe
            20                  25                  30

Ser Arg Ser Asp Ala Leu Thr Gln His Gln Arg Thr His Thr Gly Glu
        35                  40                  45

Lys Pro Tyr Lys Cys Pro Glu Cys Gly Lys Ser Phe Ser Gln Ser Ser
    50                  55                  60

His Leu Ala Arg His Gln Arg Thr His Thr Gly Glu Lys Pro Phe Lys
65                  70                  75                  80

Cys Pro Glu Cys Gly Lys Ser Phe Ser Gln Ser Ser His Leu Thr Arg
                85                  90                  95

His Gln Ala Thr His Thr Gly Gly Gly Gly Ser Gly Gly Gly Ser Gly
            100                 105                 110

Gly Gly Ser Gly Gly Gly Ser Val Leu Glu Lys Ser Asp Ile Glu Lys
        115                 120                 125

Phe Lys Asn Gln Leu Arg Thr Glu Leu Thr Asn Ile Asp His Ser Tyr
    130                 135                 140

Leu Lys Gly Ile Asp Ile Ala Ser Lys Lys Lys Thr Ser Asn Val Glu
145                 150                 155                 160

Asn Thr Glu Phe Glu Ala Ile Ser Thr Lys Ile Phe Thr Asp Glu Leu
                165                 170                 175

Gly Phe Ser Gly Lys His Leu Gly Gly Ser Asn Lys Pro Asp Gly Leu
            180                 185                 190

Leu Trp Asp Asp Asp Cys Ala Ile Ile Leu Asp Ser Lys Ala Tyr Ser
        195                 200                 205

Glu Gly Phe Pro Leu Thr Ala Ser His Thr Asp Ala Met Gly Arg Tyr
    210                 215                 220
```

```
Leu Arg Gln Phe Thr Glu Arg Lys Glu Glu Ile Lys Pro Thr Trp Trp
225                 230                 235                 240

Asp Ile Ala Pro Glu His Leu Asp Asn Thr Tyr Phe Ala Tyr Val Ser
                245                 250                 255

Gly Ser Phe Ser Gly Asn Tyr Lys Glu Gln Leu Gln Lys Phe Arg Gln
            260                 265                 270

Asp Thr Asn His Leu Gly Gly Ala Leu Glu Phe Val Lys Leu Leu Leu
        275                 280                 285

Leu Ala Asn Asn Tyr Lys Thr Gln Lys Met Ser Lys Lys Glu Val Lys
    290                 295                 300

Lys Ser Ile Leu Asp Tyr Asn Ile Ser Tyr Glu Glu Tyr Ala Pro Leu
305                 310                 315                 320

Leu Ala Glu Ile Glu
                325


<210> SEQ ID NO 52
<211> LENGTH: 9064
<212> TYPE: DNA
<213> ORGANISM: Artificial
<220> FEATURE:
<223> OTHER INFORMATION: Protein S promoter-EGFP-Protein S intron 1
      targeting construct
<220> FEATURE:
<221> NAME/KEY: misc_feature
<222> LOCATION: (5360)..(5365)
<223> OTHER INFORMATION: n is a, c, g, or t

<400> SEQUENCE: 52

ggtaccgagc tcttacgcgt gctagcccgg gctcgagatc tcaacccctt ttgaccatac     60

acatttctac tctttgtgtt tgctggagct gttttctccc cacactcaac cccctttgct    120

gaagcctgga acttgctttc cacagcttaa gttgttatag gtttcaatca tctgtccacc    180

tccctgactt tcataatttt gtgaaatacc cttgcatata tatatgggac taaatattat    240

tttctcctgg ttgtccataa tagattaatt taattcctaa acaaagaaca gaacatagat    300

tggtatagta gaagagtttc ccttctccct actgcatgaa tggaaattcc ccaaaccatc    360

cttatcagag aaattaactc acatactagt cacctttcat tcagctggat gacaaaatca    420

ttttaaaaaa agagaataaa gaaaacagat aagaacaact agatctagga ataatactta    480

aaatatgatt ctgcttagta ggtttcattc acacacctag aaaaaaaaat cagtcaatgt    540

ttcctttggg cagaaaatga gcaataatgg gtatgcattg accactactg ttggacatag    600

ccttattgct tcatatagca tctattcaaa gtctcagatc aacactatga aaacctgtca    660

tctctgtatt agatgatgtg actggggctg taaagggtaa gctcttttct tacagctata    720

caacaacgct aagaccaagt tctgtgcttt gagcccaggc agtttagttt cccaggagca    780

acctaaagcc tgattcacag gcatatgtat gatccaaact gaatggtagt acatcaatac    840

caaaacaatc tattggtgga aacacaccat aggtgatcga aatactccat tttcttttcc    900

tctcatgact tctgttctga gcagtcctct tcctaaagtc tacattgtct tctgagttca    960

ggctgacatc ttgacatcct cctggctggc acagtctctg gacaaggagg gaagaaggag   1020

agaaggggaa agggagagga gggggggagg gagagaaaga atgggaagag gaaggatatg   1080

aaagagagaa gagaggaggg aaggcgggag gaagggaggg agggagggag ggagagaggg   1140

agagagagga gagagagaga gagagagaga gagagagaga gagagagaga gagagagaga   1200

gagagggaga gggagagaga gacagagaga gagagaggga gagggagaga gagagagaga   1260

gagagagaga gagagagaga gagagagagt gaggagagag agagagagtt ttcttcacca   1320
```

-continued

```
ttggacattc ctaaagaaaa gaagtaaatg caggattggg gacagtgaca gaggacctct   1380
gataaacttt ctgaggcctc tgacctcact ctctcggagc cctcctccac cacccacccc   1440
ccccctccct agctgagaaa agcttccagg aaatgtccca gtcatcgctt cccctcccgg   1500
gctgggggct gggagcgggc ggtcccctca ggccagggct gctccggccg cgctcgggca   1560
gggccacaac agagctggga aagctgagcc caggctcgca gctcctctgg gcggagcgcc   1620
ggctcggtcc ccgctgcgcc agccgtgatc cccggcagcc tgctcagcca tggtgagcaa   1680
gggcgaggag ctgttcaccg gggtggtgcc catcctggtc gagctggacg gcgacgtaaa   1740
cggccacaag ttcagcgtgt ccggcgaggg cgagggcgat gccacctacg gcaagctgac   1800
cctgaagttc atctgcacca ccggcaagct gcccgtgccc tggcccaccc tcgtgaccac   1860
cctgacctac ggcgtgcagt gcttcagccg ctaccccgac cacatgaagc agcacgactt   1920
cttcaagtcc gccatgcccg aaggctacgt ccaggagcgc accatcttct tcaaggacga   1980
cggcaactac aagacccgcg ccgaggtgaa gttcgagggc gacaccctgg tgaaccgcat   2040
cgagctgaag ggcatcgact tcaaggagga cggcaacatc ctggggcaca agctggagta   2100
caactacaac agccacaacg tctatatcat ggccgacaag cagaagaacg gcatcaaggt   2160
gaacttcaag atccgccaca acatcgagga cggcagcgtg cagctcgccg accactacca   2220
gcagaacacc cccatcggcg acggccccgt gctgctgccc gacaaccact acctgagcac   2280
ccagtccgcc ctgagcaaag accccaacga gaagcgcgat cacatggtcc tgctggagtt   2340
cgtgaccgcc gccgggatca ctctcggcat ggacgagctg tacaagtaaa gcggccgcga   2400
ctctagagtc ggggcggccg gccgcttcga gcagacatga taagatacat tgatgagttt   2460
ggacaaacca caactagaat gcagtgaaaa aaatgcttta tttgtgaaat ttgtgatgct   2520
attgctttat ttgtaaccat tataagctgc aataaacaag ttaacaacaa caattgcatt   2580
cattttatgt ttcaggttca gggggaggtg tgggaggttt tttaaagcaa gtaaaacctc   2640
tacaaatgtg gtaaaatcga taaggatcct gctggtatgc ctagccctgg tgctgccagc   2700
ctcggagaca aactgtaagt aatccatacc tcctggcttc tccattccct atgtgccccg   2760
gcttgaagat tttccactag gctgtttgct gcctcctaag tttccagtaa gtccgccacc   2820
attcagagag tcgcggcagc ctgggtctgg tgggcagtgt aaaggtggga caggatcaaa   2880
gcttgccttg ctttgagaac cattgtccac aggacttgat tccagaaccc gggtgacact   2940
aagtgtcaaa ggaattgctt gaacatagtc ctaaatattg ctaggaaagc taagtcaagc   3000
ctgttgccct cctcccgttt acaagagtgc cccagcccgc accctctcct gcggctaacc   3060
ttccttttgc aatttctgga ctttgaactt gattgactgg tctcacattg acaaactgtt   3120
tggggactgc tggggtgtta catatgattc tctaaccttg atataagaaa tagctgttgg   3180
atgttacctt gtaccgagga tcattttctg agggttttga ctgttgccgc tttgagatgg   3240
cagcaagaat tctgtacaac acacacattt ttgtgtttct tggtctttcc tcttcccatt   3300
ctcagattcc gggcagtata tcgagttttc tcttagaaat ataaaacgaa ccacaaggtt   3360
ttagtacatt ttaatggtca attaaattgt ttttagaagc ttaaatatgt tcataattaa   3420
cactgctttc ttttgctctt ttgtagtccc agtcactggc atgggagcaa taactgtata   3480
acaaatacca cttaggtcac tgcgagcacc aaagaaactt ttcaaagatg gtaattaagt   3540
aggagtttgc tggaattgca agtttttatt aattagtaag gaatctagcc tgatattttt   3600
aaatgtctaa ctaagttaaa gaccagaatg aaactggttc actttttatt gaggataaac   3660
```

```
aagttacagt tataaagcct caacaatcaa agccctacga tgaagcagcg tgtgactgta   3720
tgcacatgat ctatcttgtt cagaggaaca atcaaacatt ttcagatagc atcagggcgg   3780
tggtggtact cgcctataat cctagcaaag tcagaggcaa gcagatctct gtgttcaagg   3840
ccagcctagt ctacagagtg agttccagga caactggggc tacacagaga aacctgtctc   3900
agagaaaaac aaaataaaac caaattcaga tagctggtgt ttgggaaaag agcaaaagac   3960
agcagtgctg gccacacaga gagtagacaa gttcattcta caaggacatc acagaaagaa   4020
tatgtgaccc aatgacgacc ataaactttc ttgttcctgt gtcaaattat ctccggttta   4080
ttgatgaaga accagacact atgagctgcg tctcctcctt aagattttgt tttggtgtct   4140
tgtttttgtc aaggggtttc attgtggccc tgagcattag atccagggct ttgtgcatgc   4200
taggccaggg agctatattc ccgaactcca gaagactagg aatttgagat ataaatagaa   4260
tttgaattac cttctgtaca attgattgta tggttctaga aatattgcta tattaaggga   4320
agcctttgca gaagacagtt attttgagat ggtgcataac acaaaagaaa tgaactaaag   4380
cctgaggcct gctctgtagc tctgccttgc ccttagccta caataacttt ctttaccttt   4440
caagcatgtg ccaccacgcc tgactttcag gcccttcatt ttaacaagaa agcaagtatt   4500
cagttatcaa ctgactttcc aaatgcattt gtatgaataa aaactacaaa aatataaaaa   4560
taagaactat acacacaaaa gccttgtatt taaaatttac gctgtggaca tattttgctc   4620
atcattcgtg agagcttgcg gtaaaaaggc aaaggggaag aggaggatat ctattttggg   4680
taggctaatt tggccttatc cagacttccc ttttgggtgg atgcagtctg cccagcacac   4740
tattggccca tttcttctac atggctttgt gctctgctct gcccttagct aattgtcccc   4800
tttgacatgc ttttgtcttt ccttaaagtt tctatacttc aaaaaccatc ccgctacact   4860
aatggagtga ttttctcaag ggttgcttta tgtttggggt ttgtactgca agagttagtt   4920
tctgatatag caatggtgat agtatagtct tctaccatga actctatgcc agcaagtaca   4980
ggggtatatt tcacatgggt gttttctgtt cactgagttt catgtcttct ttgtatcttt   5040
ttgttttgtt ttgtgagaca gggtttctct gtagcttttg agtcagtcct ggaacttgct   5100
ggccggcctt gaactcacag agattcacct gcctctgcct cccaagtgct gggatttaag   5160
gtgtgagtca ccactgccag gttttttctt tgtatcttga gtgaactaaa taggtaagct   5220
ttaaataata atatgagcag tctatttata tacattaaat attaaatgca ttgtgagatg   5280
agcatagcct ttgaggccca ggaacagaaa gatttacttc acattgtaaa tatactggta   5340
tacatacaaa cgtacatacn nnnnngtgtg tgtgtgtgtg tgtgtgtgtg tgtgcatgcc   5400
atagcacaca tgtgaagtcc agagtacagc attctctttt tctacctttc tgtagattct   5460
tgtggtcaga gtcaggtcaa atcaaatcag acagatgcat gtataaaatg ctcttaccca   5520
ctgaaccatc ttgctgcttg gtccacaagc ttagtggaag aatgctggga agtgaatagt   5580
atgtttttaa atgtagttaa ccttgacttt ttgttgttgt tgctgttatt gaggccacat   5640
tttcattgtt ctgagaaaat attactattt tcctcagaca gaattatata tttatttgaa   5700
gttcatgaat tccatattat tttcctgtat ttattacaaa tagcatgctt aaacacttcc   5760
aagtagtgaa acagctgctc atgtaggaca cggattattg acagtgctgc catttatcag   5820
ccagtaatcc acttggcagg tagcacgctc atcgttatcc tttatgcaca caaagccttg   5880
tttgaatttt atcttttaat gagtgtcaat gaaatggaaa gagataagag ttaaaaatac   5940
aacccaaact attgtattta catttctctt ttagaagaaa cctaaagcag cattacttct   6000
tgcccatatt taataaataa catcatttac ccttgttccc tgcctccaga ctctcccata   6060
```

```
tactcctctt tcaattttat tggccccttt aaatgacata tcattacatg tatatcccta   6120

cacataagta taaccagttc agtttgtata atgttacttg catgtgtgtt ttcaatgctg   6180

atcatttggt agtggataac caatggtgtg ccctatgaag ggcagagta tttgtatcat   6240

gcttagcatt cctttgtcga ccgatgccct tgagagcctt caacccagtc agctccttcc   6300

ggtgggcgcg gggcatgact atcgtcgccg cacttatgac tgtcttcttt atcatgcaac   6360

tcgtaggaca ggtgccggca gcgctcttcc gcttcctcgc tcactgactc gctgcgctcg   6420

gtcgttcggc tgcggcgagc ggtatcagct cactcaaagg cggtaatacg gttatccaca   6480

gaatcagggg ataacgcagg aaagaacatg tgagcaaaag gccagcaaaa ggccaggaac   6540

cgtaaaaagg ccgcgttgct ggcgtttttc cataggctcc gcccccctga cgagcatcac   6600

aaaaatcgac gctcaagtca gaggtggcga aacccgacag gactataaag ataccaggcg   6660

tttccccctg gaagctccct cgtgcgctct cctgttccga ccctgccgct taccggatac   6720

ctgtccgcct ttctcccttc gggaagcgtg gcgctttctc atagctcacg ctgtaggtat   6780

ctcagttcgg tgtaggtcgt tcgctccaag ctgggctgtg tgcacgaacc ccccgttcag   6840

cccgaccgct gcgccttatc cggtaactat cgtcttgagt ccaacccggt aagacacgac   6900

ttatcgccac tggcagcagc cactggtaac aggattagca gagcgaggta tgtaggcggt   6960

gctacagagt tcttgaagtg gtggcctaac tacggctaca ctagaagaac agtatttggt   7020

atctgcgctc tgctgaagcc agttaccttc ggaaaaagag ttggtagctc ttgatccggc   7080

aaacaaacca ccgctggtag cggtggtttt tttgtttgca agcagcagat tacgcgcaga   7140

aaaaaaggat ctcaagaaga tcctttgatc ttttctacgg ggtctgacgc tcagtggaac   7200

gaaaactcac gttaagggat tttggtcatg agattatcaa aaaggatctt cacctagatc   7260

cttttaaatt aaaaatgaag ttttaaatca atctaaagta tatatgagta aacttggtct   7320

gacagttacc aatgcttaat cagtgaggca cctatctcag cgatctgtct atttcgttca   7380

tccatagttg cctgactccc cgtcgtgtag ataactacga tacgggaggg cttaccatct   7440

ggccccagtg ctgcaatgat accgcgagac ccacgctcac cggctccaga tttatcagca   7500

ataaaccagc cagccggaag ggccgagcgc agaagtggtc ctgcaacttt atccgcctcc   7560

atccagtcta ttaattgttg ccgggaagct agagtaagta gttcgccagt taatagtttg   7620

cgcaacgttg ttgccattgc tacaggcatc gtggtgtcac gctcgtcgtt tggtatggct   7680

tcattcagct ccggttccca acgatcaagg cgagttacat gatcccccat gttgtgcaaa   7740

aaagcggtta gctccttcgg tcctccgatc gttgtcagaa gtaagttggc cgcagtgtta   7800

tcactcatgg ttatggcagc actgcataat tctcttactg tcatgccatc cgtaagatgc   7860

ttttctgtga ctggtgagta ctcaaccaag tcattctgag aatagtgtat gcggcgaccg   7920

agttgctctt gcccggcgtc aatacgggat aataccgcgc cacatagcag aactttaaaa   7980

gtgctcatca ttggaaaacg ttcttcgggg cgaaaactct caaggatctt accgctgttg   8040

agatccagtt cgatgtaacc cactcgtgca cccaactgat cttcagcatc ttttactttc   8100

accagcgttt ctgggtgagc aaaaacagga aggcaaaatg ccgcaaaaaa gggaataagg   8160

gcgacacgga aatgttgaat actcatactc ttcctttttc aatattattg aagcatttat   8220

cagggttatt gtctcatgag cggatacata tttgaatgta tttagaaaaa taaacaaata   8280

ggggttccgc gcacatttcc ccgaaaagtg ccacctgacg cgccctgtag cggcgcatta   8340

agcgcggcgg gtgtggtggt tacgcgcagc gtgaccgcta cacttgccag cgccctagcg   8400
```

-continued

```
cccgctcctt tcgctttctt cccttccttt ctcgccacgt tcgccggctt tccccgtcaa   8460

gctctaaatc gggggctccc tttagggttc cgatttagtg ctttacggca cctcgacccc   8520

aaaaaacttg attagggtga tggttcacgt agtgggccat cgccctgata gacggttttt   8580

cgccctttga cgttggagtc cacgttcttt aatagtggac tcttgttcca aactggaaca   8640

acactcaacc ctatctcggt ctattctttt gatttataag ggattttgcc gatttcggcc   8700

tattggttaa aaaatgagct gatttaacaa aaatttaacg cgaattttaa caaaatatta   8760

acgcttacaa tttgccattc gccattcagg ctgcgcaact gttgggaagg gcgatcggtg   8820

cgggcctctt cgctattacg ccagcccaag ctaccatgat aagtaagtaa tattaaggta   8880

cgggaggtac ttggagcggc cgcaataaaa tatctttatt ttcattacat ctgtgtgttg   8940

gtttttttgtg tgaatcgata gtactaacat acgctctcca tcaaaacaaa acgaaacaaa   9000

acaaactagc aaaataggct gtccccagtg caagtgcagg tgccagaaca tttctctatc   9060

gata                                                                9064
```